United States Patent
Maffioli et al.

(10) Patent No.: US 9,975,930 B2
(45) Date of Patent: May 22, 2018

(54) LANTIBIOTIC DERIVATIVES AND PROCESS FOR THEIR PREPARATION

(71) Applicant: NAICONS S.r.l., Milan (IT)

(72) Inventors: Sonia I. Maffioli, Milan (IT); Paolo Monciardini, Cislago (IL); Bruno Catacchio, Locarno (CH); Mariacristina Brunati, Monza (IT); Carlo Mazzetti, Milan (IL)

(73) Assignee: NAICONS S.R.L., Milan (IT)

( * ) Notice: Subject to any disclaimer, the term of this patent is extended or adjusted under 35 U.S.C. 154(b) by 0 days. days.

(21) Appl. No.: 14/648,696

(22) PCT Filed: Nov. 27, 2013

(86) PCT No.: PCT/US2013/072307
§ 371 (c)(1),
(2) Date: May 29, 2015

(87) PCT Pub. No.: WO2014/085637
PCT Pub. Date: Jun. 5, 2014

(65) Prior Publication Data
US 2015/0274788 A1    Oct. 1, 2015

Related U.S. Application Data

(60) Provisional application No. 61/731,881, filed on Nov. 30, 2012.

(51) Int. Cl.
*A01N 37/18*    (2006.01)
*A61K 38/00*    (2006.01)
*A61P 31/04*    (2006.01)
*C07K 14/36*    (2006.01)

(52) U.S. Cl.
CPC ............. *C07K 14/36* (2013.01); *A61K 38/00* (2013.01)

(58) Field of Classification Search
CPC ................................ A61K 38/00; C07K 14/36
See application file for complete search history.

(56) References Cited

U.S. PATENT DOCUMENTS

| | | | |
|---|---|---|---|
| 7,989,416 B2 | 8/2011 | Boakes et al. | |
| 8,329,644 B2 | 12/2012 | Wadman | |
| 8,465,947 B2 | 6/2013 | Boakes et al. | |
| 2010/0048459 A1 | 2/2010 | Boakes et al. | |
| 2010/0261638 A1 | 10/2010 | Wadman | |
| 2011/0306091 A1 | 12/2011 | Boakes et al. | |
| 2014/0094402 A1 | 4/2014 | Maffioli et al. | |

FOREIGN PATENT DOCUMENTS

| | | | |
|---|---|---|---|
| WO | 2005014628 | 2/2005 | |
| WO | 2009/010765 | 1/2009 | |
| WO | WO2010/05238 | * 5/2010 | ............ C07K 14/36 |
| WO | 2012/135636 | 10/2012 | |

OTHER PUBLICATIONS

Chater. *Streptomyces* inside-out: a new perspective on the bacteria that provide us with antibiotics. Philosophical Transactions of the Royal Society B. vol. 361, No. 1469, pp. 761-786.*
Plat et al. Activity and Export of Engineered Nisin-(1-22) Analogs. Polymers 2011. vol. 3, pp. 1282-1296.*
International Search Report for PCT/US2013/072307, five pages, (dated Feb. 2014).
Written Opinion of ISA for PCT/US2013/072307, eight pages, (dated Feb. 2014).
Cooper et al. "Biosynthesis and mode of action of lantibiotics" *Comprehensive Natural Products II*, chapter 5.08, pp. 217-220 (2010).
Field et al. "The generation of nisin variants with enhanced activity against specific Gram-positive pathogens" *Molecular Microbiology*, vol. 69, No. 1, pp. 218-230 (May 2008).
Field et al. "Bioengineered nisin A derivatives with enhanced activity against both Gram positive and Gram negative pathogens" *PLOS One*, vol. 7, No. 10, e46884, 12 pages (Oct. 2012).
Knerr & Van Der Donk "Chemical synthesis and biological activity of analogues of the lantibiotic epilancin 15X" *Journal of the American Chemical Society*, vol. 134, No. 18, pp. 7648-7651 (Apr. 2012).
Mota-Meira et al. "Purification and structure of mutacin B-Ny266: A new lantibiotic produced by *Streptoccocus mutans*" *FEBS Letters*, vol. 410, Nos. 2-3, pp. 275-279 (Jun. 2007).
Ou et al. "GrpE protein [*Streptomyces cattleya* NRRL 8057=DSM 46488]" GenBank Accession No. AEW97476.1, one page (Dec. 2011).
International Preliminary Report on Patentability for PCT/US2013/072307, nine pages (dated Jun. 2015).
European Search Report of EP application 13858221.8 dated Jun. 8, 2016.
Champak Chatterjee et al., Biosynthesis and Mode of Action of Lantibiotics, Chem. rev. 2005, 105, 633-683 published on web on Feb. 9, 2005 American Chemical Society.
Gunter Jung, Lantibiotics—Ribosomally Synthesized Biologically Active Polypeptides containing sulfide bridges and Alpha, Beta- (Continued)

*Primary Examiner* — Marcela M Cordero Garcia

(57) ABSTRACT

The present invention concerns novel antibiotic compounds, which are lantibiotics, the processes for their preparation, their pharmaceutically acceptable salts, pharmaceutical compositions containing the lantibiotics, and their use as antibacterial agents. Compounds designated as lantibiotics, such as those of the present invention, are peptides belonging to the general class of antibiotic compounds, and are further generally characterized by the presence of the amino acids lanthionine and/or 3-methyllanthionine. The novel lantibiotic compounds are active against bacterial infections caused by *Clostridium difficile, Staphylococcus* spp., *Streptococcus* spp, *Enterococcus* spp., and other bacteria.

34 Claims, 25 Drawing Sheets

(56) References Cited

OTHER PUBLICATIONS

Didehydroamino Acids, Angewandte Chemie, vol. 30, No. 09 pp. 1051-1192.

* cited by examiner

SEQUENCE LISTING

<160> NUMBER OF SEQ ID NOS: 5

<210> SEQ ID NO 1
<211> LENGTH: 644
<212> TYPE: DNA
<213> ORGANISM: Streptomyces sp. DSM 24069

<400> SEQUENCE: 1

```
atggctcagg acgaacgctg gcggcgtgct taacacatgc aagtcgaacg atgaaccact    60
tcggtgggga ttagtggcga acgggtgagt aacacgtggg caatctgccc tgcactctgg   120
gacaagccct ggaaacgggg tctaataccg gatacaacca ctagggcat  ccctcggtgg   180 tggaaagctc cggcggtgca ggatgagccc gcggcctatc agcttgttgg tgaggtaacg   240
gctcaccaag gcgacgacgg gtagccggcc tgagagggcg accggccaca ctgggactga   300
gacacggccc agactcctac gggaggcagc agtggggaat attgcacaat gggcgaaagc   360
ctgatgcagc gacgccgcgt gagggatgac ggccttcggg ttgtaaacct ctttcagcag   420
ggaagaagcg aaagtgacgg tacctgcaga agaagcgccg gctaactacg tgccagcagc   480
cgcggtaata cgtagggcgc aagcgttgtc cggaattatt gggcgtaaag agctcgtagg   540
cggcttgtcg cgtcggttgt gaaagcccgg ggcttaaccc cgggtctgca gtcgatacgg   600
gcaggctaga gtcggtaagg ggagatcgga attcctggtg taac                     644
```

<210> SEQ ID NO 2
<211> LENGTH: 1342

<212> TYPE: DNA
<213> ORGANISM: Streptomyces sp. DSM 24058

<400> SEQUENCE: 2

```
atcatggctc aggacgaacg ctggcggcgt gcttaacaca tgcaagtcga acgatgaacc      60
acttcggtgg ggattagtgg cgaacgggtg agtaacacgt gggcaatctg ccctgcactc     120
tgggacaagc cctggaaacg gggtctaata ccggatacaa ccactgaccg catggtcggg     180
tggtggaaag ctccggcggt gcaggatgag cccgcggcct atcagcttgt tggtgaggta     240
atggctcacc aaggcgacga cgggtagccg gcctgagagg gcgaccggcc acactgggac     300
tgagacacgc cccagactcc tacgggaggc agcagtgggg aatattgcac aatgggcgca     360
agcctgatgc agcgacgccg cgtgagggat gacggccttc gggttgtaaa cctctttcag     420
cagggaagaa gcgaaagtga cggtacctgc agaagaagcg ccggctaact acgtgccagc     480
agccgcggta atacgtaggg cgcaagcgtt gtccggaatt attgggcgta agagctcgt     540
aggcggcttg tcgcgtcggt tgtgaaagcc cggggcttaa ccccgggtct gcagtcgata     600
cgggcaggct agagttcggt aggggagatc ggaattcctg gtgtagcggt gaaatgcgca     660
gatatcagga ggaacaccgg tggcgaaggc ggatctctgg gccgatactg acgctgagga     720
gcgaaagcgt ggggagcgaa caggattaga taccctggta gtccacgccg taaacggtgg     780
gcactaggtg tgggcgacat tccacgtcgt ccgtgccgca gctaacgcat taagtgcccc     840
gcctggggag tacggccgca aggctaaaac tcaaaggaat tgacggggc cgcacaagc     900
ggcggagcat gtggcttaat tcgacgcaac gcgaagaacc ttaccaaggc ttgacataca     960
ccggaaacgt ctggagacag gcgccccctt gtggtcggtg tacaggtggt gcatggctgt    1020
cgtcagctcg tgtcgtgaga tgttgggtta agtcccgcaa cgagcgcaac ccttgtcccg    1080
tgttgccagc aggcccttgt ggtgctgggg actcacggga gaccgccggg gtcaactcgg    1140
aggaaggtgg ggacgacgtc aagtcatcat gccccttatg tcttgggctg cacacgtgct    1200
acaatggccg gtacaatgag ctgcgatacc gcgaggtgga gcgaatctca aaaagccggt    1260
ctcagttcgg attggggtct gcaactcgac cccatgaagt cggagtcgct agtaatcgca    1320
gatcagcatt gctgcggtga at                                              1342
```

<210> SEQ ID NO 3
<211> LENGTH: 1425
<212> TYPE: DNA
<213> ORGANISM: Streptosporangium sp. DSM 24060

<400> SEQUENCE: 3

```
cggcgtgctt aacacatgca agtcgagcgg aaaggcccct cggggtactc gagcggcgaa      60
cgggtgagta acacgtgagt aacctgcccc tgactctggg ataagcccgg gaaactgggt     120
ctaataccgg atacgaccac ttcccgcatg ggatggtggt ggaaagttt tcggtcgggg     180
atgggctcgc ggcctatcag cttgttggtg ggtagtggc ctaccaaggc gacgacgggt     240
agccggcctg agagggcgac cggccacact gggactgaga cacggcccag actcctacgg     300
gaggcagcag tggggaatat tgcgcaatgg gcgaaagcct gacgcagcga cgccgcgtgg     360
gggatgacgg ccttcgggtt gtaaacctct ttcagcaggg acgaagttga cgtgtacctg     420
cagaagaagc gccggctaac tacgtgccag cagccgcggt aatacgtagg gcgcaagcgt     480
tgtccggaat tattgggcgt aaagagctcg taggtggctt gtcgcgtcgg tgtgaaagc     540
ttggggctta actccaggtc tgcattcgat acgggctggc tagaggtagg taggggagaa     600
```

| | |
|---|---|
| cggaattcct ggtgtagcgg tgaaatgcgc agatatcagg aggaacaccg gtggcgaagg | 660 |
| cggttctctg ggccttacct gacgctgagg agcgaaagcg tggggagcga acaggattag | 720 |
| ataccctggt agtccacgct gtaaacgttg ggcgctaggt gtggggacct tccacggttt | 780 |
| ccgcgccgta gctaacgcat taagcgcccc gcctggggag tacggccgca aggctaaaac | 840 |
| tcaaaggaat tgacggggc cgcacaagc ggcggagcat gttgcttaat tcgacgcaac | 900 |
| gcgaagaacc ttaccaaggc ttgacatcgc cggaaagct tcagagatgg agccctcttc | 960 |
| ggactgggtg acaggtggtg catggctgtc gtcagctcgt gtcgtgagat gttgggttaa | 1020 |
| gtcccgcaac gagcgcaacc cttgttccat gttgccagca cgccccttg ggggtggtgg | 1080 |
| ggactcatgg gagactgccg gggtcaactc ggaggaaggt ggggatgacg tcaagtcatc | 1140 |
| atgccctta tgtcttgggc tgcaaacatg ctacaatggc cggtacagag ggttgcgata | 1200 |
| ccgtgaggtg gagcgaatcc ctaaaagccg gtctcagttc ggattggggt ctgcaactcg | 1260 |
| accccatgaa gtcggagtcg ctagtaatcg cagatcagca acgctgcggt gaatacgttc | 1320 |
| ccgggccttg tacacaccgc ccgtcacgtc acgaaagtcg caacacccg aagcccgtgg | 1380 |
| cccaaccagc ttgctggggg gagcggtcga aggtggggct ggcga | 1425 |

<210> SEQ ID NO 4
<211> LENGTH: 1448
<212> TYPE: DNA
<213> ORGANISM: Streptomyces sp. DSM 24056

<400> SEQUENCE: 4

| | |
|---|---|
| gacgaacgct ggcggcgtgc ttaacacatg caagtcgaac gatgaagccc tttcggggt | 60 |
| ggattagtgg cgaacgggtg agtaacacgt gggcaatctg ccctgcactt cgggacaagc | 120 |
| cctggaaacg gggtctaata ccggatacaa ctcccttggg catccttggg ggtggaaagc | 180 |
| ttcggcggtg caggatgagc ccgcggccta tcagcttgtt ggtggggtga tggcctacca | 240 |
| aggcgacgac gggtagccgg cctgagaggg cgaccggcca cactgggact gagacacggc | 300 |
| ccagactcct acgggaggca gcagtgggga atattgcaca atgggcgaaa gcctgatgca | 360 |
| gcgacgccgc gtgagggatg acggccttcg ggttgtaaac ctctttcagc agggaagaag | 420 |
| cgagagtgac ggtacctgca gaagaagcac cggctaacta cgtgccagca gccgcggtaa | 480 |
| tacgtagggt gcgagcgttg tccggaatta ttgggcgtaa agagctcgta ggcggcctgt | 540 |
| cacgtcggat gtgaaagccc ggggcttaac cctgggtctg cattcgatac gggcaggcta | 600 |
| gagttcggta ggggagatcg gaattcctgg tgtagcggtg aaatgcgcag atatcaggag | 660 |
| gaacaccggt ggcgaaggcg gatctctggg ccgatactga cgctgaggag cgaaagcatg | 720 |
| gggagcgaac aggattagat accctggtag tccatgccgt aaacgttggg cactaggtgt | 780 |
| gggcgacatt ccacgttgtc cgtgccgcag ctaacgcatt aagtgccccg cctggggagt | 840 |
| acggccgcaa ggctaaaact caaaggaatt gacggggcc cgcacaagcg gcggagcatg | 900 |
| tggcttaatt cgacgcaacg cgaagaacct taccaaggct tgacatacac cagaaagctg | 960 |
| tggagacaca gccccccttg tggttggtgt acaggtggtg catggctgtc gtcagctcgt | 1020 |
| gtcgtgagat gttgggttaa gtcccgcaac gagcgcaacc cttatcctgt gttgccagca | 1080 |
| actcttcgga ggttggggac tcacgggaga ctgccgggt caactcggag gaaggtgggg | 1140 |
| acgacgtcaa gtcatcatgc ccttatgtc ttgggctgca cacgtgctac aatggccggt | 1200 |
| acaatgagtt gcgatgccgt gaggtggagc gaatctcaaa aagccggtct cagttcggat | 1260 |
| tggggtctgc aactcgaccc catgaagtcg gagtcgctag taatcgcaga tcagcattgc | 1320 | tgcggtgaat acgttcccgg gccttgtaca caccgcccgt cacgtcacga aagtcggtaa    1380 cacccgaagc cggtggccca acccctcgtg ggagggagcc gtcgaaggtg ggactggcga    1440 ttgggacg                                                             1448

<210> SEQ ID NO 5
<211> LENGTH: 24
<212> TYPE: PRT
<213> ORGANISM: Streptomyces sp. DSM 24069, Streptomyces sp. DSM 24058,
      Streptosporangium sp. DSM 24060, Streptomyces sp. DSM 24056
<220> FEATURE:
<221> NAME/KEY: MOD_RES
<222> LOCATION: (2)..(2)
<223> OTHER INFORMATION: Amino acid in position 2 is Dehydrobutyrine
      (Dhb) an unusual Amino Acid.
<220> FEATURE:
<221> NAME/KEY: THIOETH
<222> LOCATION: (3)..(7)
<223> OTHER INFORMATION: thioether bond between amino acid in position 3
      (Ala) and amino acid in position 7 (Ala)
<220> FEATURE:
<221> NAME/KEY: MISC_FEATURE
<222> LOCATION: (4)..(4)
<223> OTHER INFORMATION: Amino acid in position 4 (represented as "X"
      in the description) is an amino acid chosen among Ala, Val, Leu
      or Ile.
<220> FEATURE:
<221> NAME/KEY: MOD_RES
<222> LOCATION: (5)..(5)
<223> OTHER INFORMATION: Amino acid in position 5 is dehydroalanine
      (Dha), an unusual amino acid.
<220> FEATURE:
<221> NAME/KEY: MISC_FEATURE
<222> LOCATION: (6)..(6)
<223> OTHER INFORMATION: Amino acid in position 6 (represented as "Y"
      in the description) is an amino acid chosen among Phe, Tyr, Trp or
      His.
<220> FEATURE:
<221> NAME/KEY: MOD_RES
<222> LOCATION: (8)..(8)
<223> OTHER INFORMATION: Amino Acid in position 8 is 2-Aminobutyric Acid
      (Abu), an unusual amino acid.
<220> FEATURE:
<221> NAME/KEY: THIOETH
<222> LOCATION: (8)..(11)
<223> OTHER INFORMATION: thioether bond between amino acid in position
      8 (Abu) and amino acid in position 11 (Ala)
<220> FEATURE:
<221> NAME/KEY: THIOETH
<222> LOCATION: (13)..(20)
<223> OTHER INFORMATION: thioether bond between amino acid in position
      13 (Ala) and amino acid in position 20 (Ala)
<220> FEATURE:
<221> NAME/KEY: MOD_RES
<222> LOCATION: (14)..(14)
<223> OTHER INFORMATION: Amino Acid in position 14 is a gly modified to
      have side chain -(CH2)n-CO-R1 (instead of H), wherein n is 1 or 2,
      and R1 is as defined in the application as filed, from page 4 line
      3 to page 7 line 16.
<220> FEATURE:
<221> NAME/KEY: THIOETH
<222> LOCATION: (18)..(23)
<223> OTHER INFORMATION: thioether bond between amino acid in position
      18 (Ala) and amino acid in position 23 (Ala)
<220> FEATURE:
<221> NAME/KEY: THIOETH
<222> LOCATION: (21)..(24)
<223> OTHER INFORMATION: thioether bond between amino acid in position
      21 (Ala) and amino acid in position 24 (modified cys) via the
      thiol side chain of the modified cys in position 24
<220> FEATURE:
<221> NAME/KEY: MOD_RES
<222> LOCATION: (24)..(24)
<223> OTHER INFORMATION: Amino Acid in position 24 is a cys modified to
      have substituent R2 instead of the -OH portion of its carboxy
      funtional group, wherein R2 is as defined in the application as -continued

```
            filed, from page 4 line 3 to page 7 line 16.

<400> SEQUENCE: 5

Ile Xaa Ala Xaa Xaa Xaa Ala Xaa Pro Gly Ala Thr Ala Gly Gly Gly
1               5                   10                  15

Gly Ala Gly Ala Ala His Ala Cys
            20
```

LANTIBIOTIC DERIVATIVES AND PROCESS FOR THEIR PREPARATION

RELATED APPLICATIONS

This application is the U.S. national phase of International Application No. PCT/US2013/072307, filed 27 Nov. 2013, which designated the U.S. and claims the benefit of U.S. Provisional Application No. 61/731,881, filed 30 Nov. 2012; the entire contents of each of which are hereby incorporated by reference.

INCORPORATION BY REFERENCE

Incorporated by reference herein is the TXT file named 15435NeSseqListingWithSeqFormula1ST25.txt created on 20 Apr. 2017 and containing 9722 bytes of information.

FIELD OF THE INVENTION

The present invention concerns novel lantibiotic compounds having general formula (I), the processes for their preparation, their pharmaceutical acceptable salts and the pharmaceutical compositions containing them as well as their use as antibacterial agents.

BACKGROUND

The compounds designated as lantibiotics are peptides belonging to the general definition of antibiotic compounds, characterized by the presence of the amino acids lanthionine and/or 3-methyllanthionine. The term lantibiotic thus defines a structural feature of these compounds and not necessarily a common possible pharmacological activity. In fact, some lantibiotics possess antibacterial activity while others are totally devoid of it. Among the lantibiotics possessing antibacterial activity, of particular relevance are those active against methicillin-resistant *Staphylococcus aureus* (MRSA), which can be of considerable interest in medicine. All the lantibiotics endowed with antibacterial activity described so far, exert their action by interfering with cell wall biosynthesis, through sequestration of a key intermediate in peptidoglycan formation.

The antibacterial lantibiotics can be broadly divided into two groups on the basis of their structures: type-A lantibiotics are typically elongated, amphiphilic peptides, while type-B lantibiotics are compact and globular. Nisin is the typical representative of type A lantibiotic, whereas actagardine and mersacidin belong to the type B lantibiotic subclass. Remarkably, despite differences in shape and primary structure, both nisin-type and mersacidin-type lantibiotics interact with the membrane-bound peptidoglycan precursor lipid II. Furthermore, while the spectrum of antibacterial activity is generally restricted to Gram-positive bacteria, individual members of subclasses A and B greatly vary in their potency. Overall, the structural elements responsible for increased target binding and/or enhanced antibacterial activity in lantibiotics are poorly understood.

Traditionally, lantibiotics have been isolated mostly from the order Firmicutes (low G-C Gram-positive bacteria) and relatively few have been described from the Actinomycetales, the order best known for the ability to produce a large variety of other antibacterial agents. Actagardine and the recently described 107891 (International Publication Number WO2005/014628) are representative lantibiotics produced by the Actinomycetales.

These lantibiotics are active in vitro against Methicillin-Resistant *Staphylococcus aureus* (MRSA), streptococci and enterococci. *S. aureus* can cause life-threatening infections and MRSA is of particular clinical significance because it is resistant to all penicillins and cephalosporins and also to multiple other antibiotics; in addition it easily spreads from patient to patient causing outbreaks of infection with important implications for healthcare facilities. Vancomycin resistant enterococci (VRE) are emerging as important hospital-acquired pathogens responsible for severe human infections (such as endocarditis, meningitis and septicemia) posing an increasing therapeutic challenge. *Streptococcus pneumoniae* and *Moraxella catarrhalis* are recognized important human pathogens. They are a common cause of respiratory tract infections, particularly otitis media in children and lower respiratory tract infections in the eldery. *M. catarrhalis* and *S. pneumoniae* have been recently accepted as the commonest pathogens of the respiratory tract.

Variants and/or derivatives of naturally occurring antibiotics have been long sought after and can be useful in medicine. They can be produced by chemical synthesis or by modification of a natural product, but most structural variations in naturally occurring antibiotics tend to abolish or severely impair their antibacterial activity. This is particularly true in the field of lantibiotics, where structure-activity relationships (SAR) are poorly defined, in the absence of molecular details about antibiotic-target interactions. Furthermore, other factors likely to contribute to antibacterial potency are the diffusion rate of the compound to the target, after crossing the thick peptidoglycan layer, and possible interactions with polar, charged and hydrophobic moieties present on the protective external surfaces of the bacterial cell. An additional element rendering unpredictable the outcome of lantibiotic modifications is the existence of unrelated compounds possessing a similar mechanism of action, preventing conclusions drawn from SAR studies on one subtype to be applied to the other.

DETAILED DESCRIPTION

The disclosure herein encompasses novel lantibiotic compounds, processes for their preparation and their use in therapy, including for treating conditions requiring antibacterial therapy. These and other aspects of the present disclosure are described herein.

The present disclosure encompasses novel antibiotic compounds, which are lantibiotics, having the general formula (I), the processes for their preparation, and the pharmaceutical compositions containing them, their pharmaceutical acceptable salts and their use as antibacterial agents.

The present disclosure encompasses lantibiotic substances of microbial origin of general formula (I), their pharmaceutical acceptable salts, pharmaceutical compositions and their use as antibacterial agents.

The present disclosure encompasses a process for preparing lantibiotic derivatives according to formula (I), which comprises culturing one of the following strains: *Streptomyces* sp. ID105857 hereinafter identified as *Streptomyces* sp. DSM 24069 (deposited on 29 Sep. 2010 with the Deutsche Sammlung von Mikroorganismen und Zellkulturen GmbH (DSMZ) with accession number DSM 24069), or *Streptomyces* sp. ID106130 hereinafter identified as *Streptomyces* sp. DSM 24058 (deposited on 29 Sep. 2010 with the Deutsche Sammlung von Mikroorganismen und Zellkulturen GmbH (DSMZ) with accession number DSM 24058), or *Streptosporangium* sp. ID114623 hereinafter identified as *Streptosporangium* sp. DSM 24060 (deposited on 29 Sep. 2010 with the Deutsche Sammlung von Mikroorganismen und Zellkulturen GmbH (DSMZ) with accession number DSM 24060), or *Streptomyces* sp. ID99438 hereinafter identified as *Streptomyces* sp. DSM 24056 (deposited on 29 Sep. 2010 with the Deutsche Sammlung von Mikroorganismen und Zellkulturen GmbH (DSMZ) with accession number DSM 24056) or a variant or mutant of each one, still maintaining the ability to produce lantibiotics belonging to those of general formula (I), recovering the lantibiotic according to the present disclosure from the mycelium and/or from the fermentation broth and isolating the pure substance by chromatographic means. The present disclosure also encompasses a process for the preparation of lantibiotics derivatives according to formula (I) comprising modifications through chemical reactions of the lantibiotics directly obtained from culturing different strains of *Streptomyces* sp. according to the above.

According to the disclosure encompassed herein, compounds of formula (I) (SEQ ID No. 5) have the following general formula:

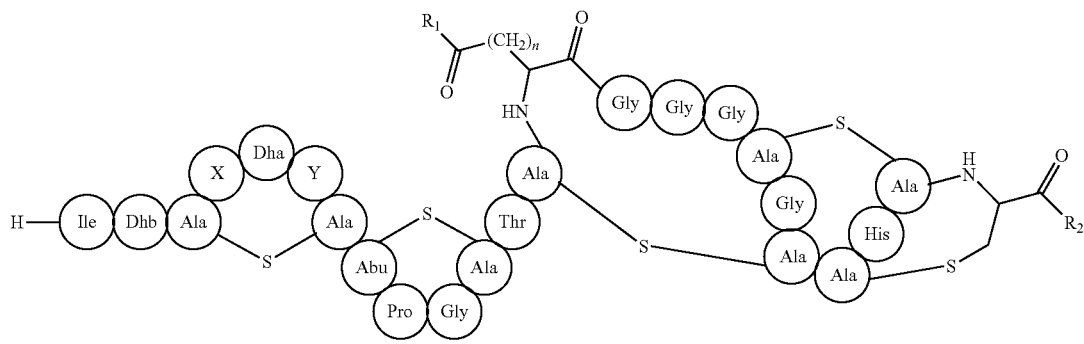

FORMULA (I)

wherein X represents an amino acid chosen among Ala, Val, Leu or Ile; Y represents an amino acid chosen among Phe, Tyr, Trp or His; n is 1 or 2
and $R_1$ and $R_2$ independently represent OH or $NR_3R_4$ wherein $R_3$ and $R_4$ independently represent:
  hydrogen or
  an alkyl of 1 to 20 carbon atoms;
  an alkenyl of 2 to 20 carbon atoms;
  an alkynyl of 2 to 20 carbon atoms;
  a cycloalkyl of 3 to 8 carbon atoms optionally substituted by one or two substituents independently selected from halo, cyano, (C1-C4)alkyl optionally substituted by 1 to 3 halogen atoms, (C1-C4)alkoxy optionally substituted by 1 to 3 halogen atoms, phenyl, phenyl-(C1-C4)alkyl, phenoxy, phenoxy-(C1-C4)alkyl wherein each of phenyl, phenyl portion of the phenyl (C1-C4), alkoxy, phenoxy, phenoxy portion of the phenoxy-(C1-C4)alkyl group is optionally substituted by 1 to 3 halogen atoms, and (C1-C4)alkoxy optionally substituted by 1 to 3 halogen atoms;
  a phenyl radical optionally substituted by one or two substituents independently selected from halo, cyano, (C1-C4)alkyl optionally substituted by 1 to 3 halogen atoms, (C1-C4)alkoxy optionally substituted by 1 to 3 halogen atoms, phenyl, phenyl-(C1-C4)alkyl, phenoxy, phenoxy-(C1-C4)alkyl wherein each of phenyl, phenyl portion of the phenyl (C1-C4), alkoxy, phenoxy, phenoxy portion of the phenoxy-(C1-C4)alkyl group is optionally substituted by 1 to 3 halogen atoms, and (C1-C4)alkoxy optionally substituted by 1 to 3 halogen atoms
  a benzyl radical optionally substituted on the phenyl ring by one or two substituents independently selected from halo, cyano, (C1-C4)alkyl optionally substituted by 1 to 3 halogen atoms, (C1-C4)alkoxy optionally substituted by 1 to 3 halogen atoms, phenyl, phenyl-(C1-C4)alkyl, phenoxy, phenoxy-(C1-C4)alkyl wherein each of phenyl, phenyl portion of the phenyl (C1-C4), alkoxy, phenoxy, phenoxy portion of the phenoxy-(C1-C4)alkyl group is optionally substituted by one or two substituents selected from halo, cyano, (C1-C4)alkyl optionally substituted by 1 to 3 halogen atoms, and (C1-C4)alkoxy optionally substituted by 1 to 3 halogen atoms
  a naphthyl radical optionally substituted by one or two substituents selected from halo, (C1-C4)alkyl optionally substituted by 1 to 3 halogen atoms, and (C1-C4) alkoxy optionally substituted by 1 to 3 halogen atoms
  a group of formula $-(CH_2)_pOR_5$ in which p represents an integer from 2 to 8 and $R_5$ represents
  hydrogen or
  $(C_1-C_4)$ alkyl or
  a cycloalkyl of 3 to 8 carbon atom optionally substituted by one or two substituents independently selected from halo, cyano, (C1-C4)alkyl optionally substituted by 1 to 3 halogen atoms, (C1-C4)alkoxy optionally substituted by 1 to 3 halogen atoms, phenyl, phenyl-(C1-C4)alkyl, phenoxy, phenoxy-(C1-C4)alkyl wherein each of phenyl, phenyl portion of the phenyl (C1-C4), alkoxy, phenoxy, phenoxy portion of the phenoxy(C1-C4)alkyl group is optionally substituted by one or two substituents selected from halo, cyano, (C1-C4)alkyl optionally substituted by 1 to 3 halogen atoms, and (C1-C4)alkoxy optionally substituted by 1 to 3 halogen atoms
  a phenyl radical optionally substituted by one or two substituents independently selected from halo, cyano, (C1-C4)alkyl optionally substituted by 1 to 3 halogen atoms, (C1-C4)alkoxy optionally substituted by 1 to 3 halogen atoms, phenyl, phenyl-(C1-C4)alkyl, phenoxy, phenoxy-(C1-C4)alkyl wherein each of phenyl, phenyl portion of the phenyl (C1-C4), alkoxy, phenoxy, phenoxy portion of the phenoxy-(C1-C4)alkyl group is optionally substituted by one or two substituents selected from halo, cyano, (C1-C4)alkyl optionally substituted by 1 to 3 halogen atoms, and (C1-C4)alkoxy optionally substituted by 1 to 3 halogen atoms a group of formula $$—(CH_2)q NR_6R_7$$

in which q represents an integer from 2 to 8 and $R_6$ and $R_7$ independently represent hydrogen or $(C_1-C_4)$ alkyl or a cycloalkyl of 3 to 8 carbon atom optionally substituted by one or two substituents independently selected from halo, cyano, (C1-C4)alkyl optionally substituted by 1 to 3 halogen atoms, (C1-C4)alkoxy optionally substituted by 1 to 3 halogen atoms, phenyl, phenyl-(C1-C4)alkyl, phenoxy, phenoxy-(C1-C4)alkyl wherein each of phenyl, phenyl portion of the phenyl (C1-C4), alkoxy, phenoxy, phenoxy portion of the phenoxy-(C1-C4)alkyl group is optionally substituted by one or two substituents selected from halo, cyano, (C1-C4)alkyl optionally substituted by 1 to 3 halogen atoms, and (C1-C4) alkoxy optionally substituted by 1 to 3 halogen atoms a phenyl radical optionally substituted by one or two substituents independently selected from halo, cyano, (C1-C4)alkyl optionally substituted by 1 to 3 halogen atoms, (C1-C4)alkoxy optionally substituted by 1 to 3 halogen atoms, phenyl, phenyl-(C1-C4)alkyl, phenoxy, phenoxy-(C1-C4)alkyl wherein each of phenyl, phenyl portion of the phenyl (C1-C4), alkoxy, phenoxy, phenoxy portion of the phenoxy-(C1-C4)alkyl group is optionally substituted by 1 to 3 halogen atoms, and (C1-C4)alkoxy optionally substituted by 1 to 3 halogen atoms a benzyl radical optionally substituted on the phenyl ring by one or two substituents independently selected from halo, cyano, (C1-C4)alkyl optionally substituted by 1 to 3 halogen atoms, (C1-C4)alkoxy optionally substituted by 1 to 3 halogen atoms, phenyl, phenyl-(C1-C4)alkyl, phenoxy, phenoxy-(C1-C4)alkyl wherein each of phenyl, phenyl portion of the phenyl (C1-C4), alkoxy, phenoxy, phenoxy portion of the phenoxy-(C1-C4)alkyl group is optionally substituted by one or two substituents selected from halo, cyano, (C1-C4)alkyl optionally substituted by 1 to 3 halogen atoms, and (C1-C4) alkoxy optionally substituted by 1 to 3 halogen atoms $R_6$ and $R_7$ taken together represent a $—(CH_2)_3$, $—(CH_2)_4—$, $—(CH_2)_2—O—(CH_2)_2$, $—(CH_2)_2—S—(CH_2)_2$ or $R_6$ and $R_7$ taken together with the adjacent nitrogen atom represent: a piperazine moiety which may be substituted in position 4 with a substituent selected from $(C_1-C_4)$ alkyl, $(C_3-C_8)$ cycloalkyl, pyridyl, benzyl and substituted benzyl wherein the phenyl moiety bears 1 or 2 substituents selected from chloro, bromo, nitro, $(C_1-C_4)$ alkyl and $(C_1-C_4)$ alkoxy provided that when n=2, X is never selected as Val and Y is never selected as Trp.

In particular embodiments are featured lantibiotic compounds of formula (I) herewith arbitrarily named NAI-857, NAI-130, NAI-114 and NAI-438.

In an embodiment, the terms "antibiotic NAI-857", "lantibiotic NAI-857", or simply "NAI-857" are referred, unless otherwise specified, to the novel lantibiotic compound of general formula (I), wherein X is Ile, Y is Tyr, n is 1 and $R_1$ and $R_2$ are OH.

In an embodiment, the terms "antibiotic NAI-130", "lantibiotic NAI-130", or simply "NAI-130" are referred, unless otherwise specified, to the novel lantibiotic compound of general formula (I), wherein X is Val, Y is Tyr, n is 1 and $R_1$ and $R_2$ are OH.

In an embodiment, the terms "antibiotic NAI-114", "lantibiotic NAI-114", or simply "NAI-114" are referred, unless otherwise specified, to the novel lantibiotic compound of general formula (I), wherein X is Ile, Y is Trp, n is 2 and $R_1$ and $R_2$ are OH.

In an embodiment, the terms "antibiotic NAI-438", "lantibiotic NAI-438", or simply "NAI-438" are referred, unless otherwise specified, to the novel lantibiotic compound of general formula (I), wherein X is Ile, Y is Tyr, n is 2 and R1 and R2 are OH.

Generally lantibiotics are known for their conservative and complex structure, lantibiotics of the present disclosure overcome the limits of prior art. In fact the disclosure encompasses novel lantibiotics wherein specific and conservative amino acids, in a polypeptide chain, are substituted and replaced on the basis of chemical and functional similarity. In an embodiment, substitution and/or replacement are predetermined. In another embodiment, substitution and/or replacement are determined using experimental testing to identify the most suitable amino acid to use in a particular position, based on the desired use and/or function of the resultant lantibiotic.

The term "$(C_1-C_4)$ alkyl" represents straight or branched alkyl chains of from 1 to 4 carbon atoms such as, but not limited to: methyl, ethyl, propyl, 1-methylethyl, butyl, 1-methylpropyl or 1,1-dimethylethyl. The term "$(C_3-C_8)$ cycloalkyl" represents a cycloalkyl group selected from cyclopropyl, cyclobutyl, cyclopentyl, cyclohexyl and cycloheptyl, ciclooctyl. The term "$(C_1-C_4)$ alkoxy" represents a straight or branched alkoxy chain of 1 to 4 carbon atoms such as, but not limited to, methoxy, ethoxy, propoxy, 1-methylethoxy, butoxy, 1-methylpropoxy and 1,1-dimethylethoxy.

According to another embodiment, when X is Ile, Y is Trp, n is 2 and $R_1$ and $R_2$ is $NR_3R_4$ where $R_3$ (or $R_4$) is H and $R_4$ (or $R_3$) is $(CH_2)qNR_6R_7$ with q=2 and $R_6$ and $R_7$ are H, the compound is called NAI-114 derivative.

According to still another embodiment, when X is Ile, Y is Tyr, n is 1 and $R_1$ and $R_2$ is $NR_3R_4$ where $R_3$ (or $R_4$) is H and $R_4$ (or $R_3$) is $(CH_2)qNR_6R_7$ with q=2 and $R_6$ and $R_7$ are H, the compound is called NAI-857 derivative.

In another preferred embodiment, the present disclosure encompasses novel compounds of general formula (I) wherein X represents an amino acid chosen among Ala, Val, Leu or Ileu; Y represents an amino acid chosen among Phe, Tyr, Trp or His; n is 1 or 2 and $R_1$ and $R_2$ are independently chosen among $NR_3R_4$ wherein the group $—NR_3R_4$ has the following formula:

$$—NH—(CH_2)_2—NH_2; \quad —NH(CH_2)_3NH_2$$

$$—NH—(CH_2)_4—NH_2; \quad —NH(CH_2)_3NHCH_3$$

$$—NH—(CH_2)_3—N(CH_3)_2; \quad —NH—(CH_2)_3N(C_2H_5)_2$$

$$—NH—(CH_2)_3N(C_3H_7)_2; \quad —NH—(CH_2)_3N(C_4H_9)_2$$

$$—NH—(CH_2)_5N(CH_3)_2; \quad —NH(CH_2)_6N(CH_3)_2$$

—NH(CH₂)₆NHCH₃;  —N[(CH₂)₂NH₂]₂

—N[(CH₂)₃NH₂]₂;  —N[(CH₂)₂N(CH₃)₂]₂

—N[(CH₂)₃N(CH₃)₂]₂;  —N[(CH₂)₄NH₂]₂

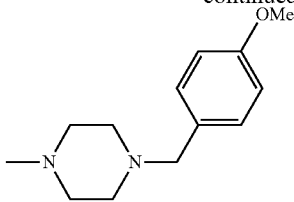

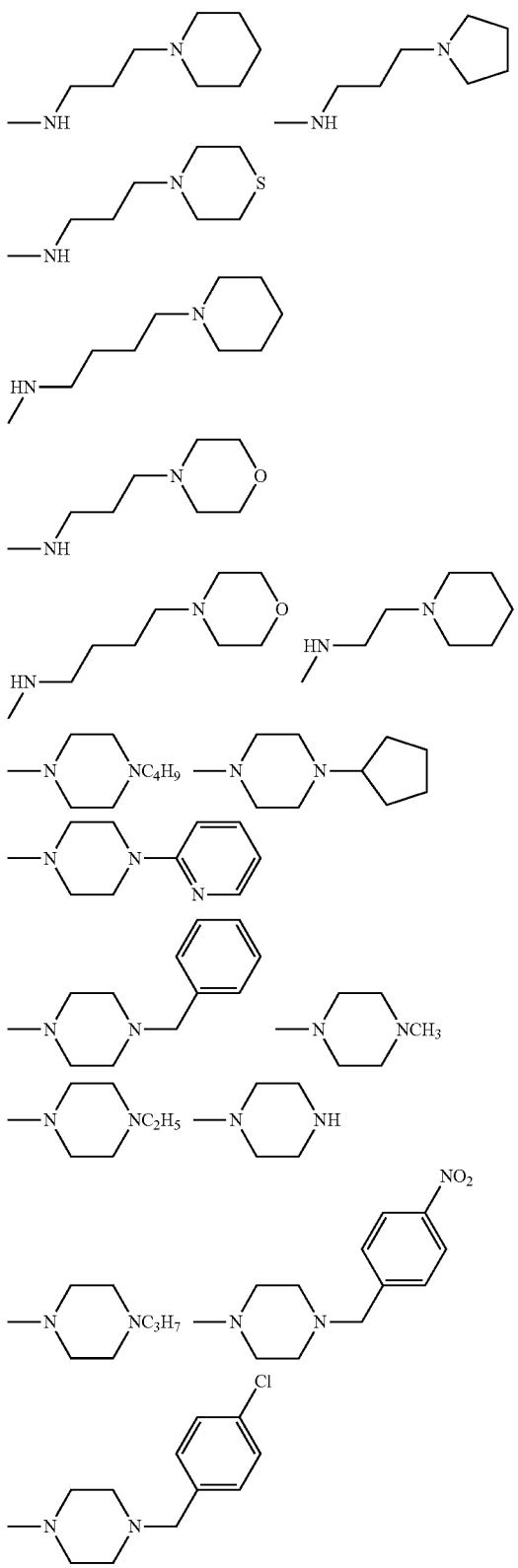

The present disclosure also encompasses a process for the preparation of the novel compounds having the general formula (I) wherein X is chosen among Ala, Leu, Val or Ile; Y is chosen among Phe, His, Tyr or Trp; n is 1 or 2 and and $R_1$ and $R_2$ represent OH or $NR_3R_4$ wherein $R_3$ and $R_4$ are defined as above.

In an embodiment, compounds of general formula (I) wherein and $R_1$ and $R_2$ represent $NR_3R_4$ can be obtained and prepared by reacting corresponding compounds of formula (I) wherein $R_1$ and $R_2$ are chosen as OH, with a selected amine of formula $HNR_3R_4$, wherein $R_3$ and $R_4$ are defined as above.

In an embodiment, the reaction is carried out in the presence of a condensing agent, i.e. in the presence of a solvent. Preferred inert organic aprotic solvents useful for the condensation reaction are those solvents which do not unfavorably interfere with the reaction course and are capable of at least partially solubilizing the starting material, for example compounds chosen among those previously indicated as NAI-857, NAI-130, NAI-114 or NAI-438. Solvents can be chosen among organic amides, ethers of glycols and polyols, phosphoramide derivatives, sulfoxides. Preferably solvents are chosen among, but not limited to: dimethylformamide, dimethoxyethane, hexamethyl phosphoroamide, dimethylsulphoxide, dioxane, N-15 methylpyrrolidone and mixtures thereof. Preferably, dimethylformamide (DMF) is employed. The condensing agent according to the present disclosure is one suitable for forming amide bonds in organic compounds and, in particular, in peptide synthesis. Representative examples of condensing agents are diisopropylcarbodiimide (DIC), dicyclohexylcarbodiimide (DCC) without or in the presence of hydroxybenzotriazole (HOBT), N,N,N',N'-tetramethyl-O-(benzotriazol-1-yl)uronium tetrafluoroborate. (TBTU), N,N,N',N'-tetramethyl-O-(7oxabenzotriazol-1-yl)uranium hexafluorophosphate (HATU), benzotriazolyl-oxy-tris-(dimethylamino)phosphonium hexafluorophosphate (HBTU), benzotriazolyloxy-tris-(pyrrolidino)phosphonium hexafluorophosphate (PyBOP) and (C1-C4) alkyl, phenyl or heterocyclic phosphorazidates such as diphenylphosphorazidate, dimorpholyl-phosphorazidate. The preferred condensing agent is PyBOP. The condensing agent is generally employed in a slight molar excess, such as from 2.2 to 5; preferably the molar excess of condensing agent is about 2.5 times the molar amount of lantibiotic starting compound, for example chosen among NAI-857, NAI-130, NAI-114 or NAI-438. According to one embodiment, the amine is used in slight molar excess with respect to the starting compound. In general, a 3 to 10 fold molar excess of the selected amine is used, while a 4-5 fold molar excess is preferred. In an embodiment, when the amine $HNR_3R_4$ is reacted as a corresponding salt, for example the hydrochloride salt, it is necessary to add a suitable base in at least a molar proportion to obtain the free base of the amine $HNR_3R_4$ which reacts with compounds for example chosen among those indicated as NAI-857, NAI-130, NAI-114 or NAI-438. In this case, an excess of the base is generally preferred. It is convenient to add a salt-forming base to the reaction mixture in an at least equimolecular amount, and preferably in about 2.2 fold molar excess with respect to the amine $HNR_3R_4$. Examples of said salt-forming bases include, but are not limited to, tertiary organic aliphatic or alicyclic amines such as trimethylamine, triethylamine (TEA), N-methylpyrrolidine or heterocyclic bases such as picoline and the like, alkali metals (e.g. sodium and potassium) hydrogen carbonates and carbonates. The reaction temperature will vary considerably depending on the specific starting materials and reaction conditions. In general, it is preferred to conduct the amidation reaction at temperature from about 0° C. to about 50° C., and in an embodiment, preferably at room temperature. Also the reaction time varies considerably, depending on the other reaction parameters; in general the condensation is completed in about 2-4 h. In an embodiment, the condensation is completed in less than 2 hours. In an embodiment, the condensation is completed in more than 4 hours. When the amine $HNR_3R_4$ contains a further primary amino group it might be protected, if necessary, as known in the art, in order to get the desired product. Any typical protecting group of the amino rest, which is resistant to the conditions applied during the process of this disclosure and may be readily removed under conditions which do not affect the stability of the compounds for example chosen among NAI-857, NAI-130, NAI-114 or NAI-438 core portion can be utilized here. In an embodiment, suitable protecting groups of the amino function can be selected, for instance, from the groups described in: T. W. Greene, "Protective Groups in Organic Synthesis", J. Wiley, N. Y., 1981. In an embodiment, in this case, those protecting groups, which are formed by acylating the amino moiety, are preferred. The protecting groups employed in the process herein described are those generally employed in peptides synthesis. A deprotection step is then necessary to obtain the desired final product. Generally, the reaction course is monitored by HPLC according to methods known in the art. On the basis of the results of this assays it will be possible to evaluate the reaction course and decide when to stop the reaction and start working up the reaction mass according to per se known techniques which include, for instance, precipitation by addition of non-solvents, extraction with solvents, in conjunction with further common separation operations and purification, e.g. by column chromatography.

Encompassed herein are a series of compounds can be prepared, as summarized in Table 1.

TABLE 1

| | $-NR_3R_4$ |
|---|---|
| 1. | —NH—cyclohexyl |
| 2. | —N(CH₃)₂ |
| 3. | —NH—CH₂CH₂CH₂—N(CH₃)₂ |
| 4. | —NH—CH₂—N(CH₃)₂ |
| 5. | —NH—CH₂—CH=CH₂ |
| 6. | —NH—CH₂—(3-methoxyphenyl) |
| 7. | —NH—CH₂CH₂—NH₂ |
| 8. | —NH—(long alkyl chain) |
| 9. | —NH—(1-naphthyl) |
| 10. | —NH—CH₂CH₂—OH |
| 11. | —NH—CH₂CH₂—OMe |
| 12. | —NH—CH₂CH₂CH₂CH₂—N(CH₃)₂ |
| 13. | —NH—CH₂—phenyl |
| 14. | —N(CH₂CH₂CH₂NH₂)₂ |
| 15. | —N—CH₂CH₂CH₂—morpholine |
| 16. | —N—CH₂CH₂CH₂—piperidine |
| 17. | —N—piperazine—NH |

TABLE 1-continued

—NR₃R₄

18. —N(piperazinyl)N—

19. —N(piperazinyl)N—cyclopentyl

20. —N(piperazinyl)N—phenyl

21. —N(piperazinyl)N—CH₂—phenyl

In an embodiment, a compound is characterized in that X is Ile, Y is Trp, n=2, $R_1$ or $R_2$ is —NHCH$_2$CH$_2$NH$_2$. The disclosure herein also encompasses a compound where X is Ile, Y is Tyr, n=1, $R_1$ or $R_2$ is —NHCH$_2$CH$_2$NH$_2$.

Compounds of general formula (I) possess acid and/or basic functions, they are capable of forming salts with suitable bases or acids according to known procedures and it may exist also in the form of inner salt. In an embodiment, the lantibiotics, when obtained in the acid form or in the form of inner salt, may be converted into a corresponding non-toxic pharmaceutically acceptable salt with bases. Suitable salts include the alkali and alkaline earth metal salts, typically the sodium, potassium, calcium and magnesium salts, and the ammonium and substituted ammonium salts. Representative, non-limiting, substituted ammonium salts include primary, secondary or tertiary (C1-C4) alkylammonium and hydroxy (C1-C4) alkylammonium salts and, according to an embodiment of the present disclosure, the benzathine, procaine, hydrabamine and similar water insoluble, non-toxic, pharmaceutically acceptable salts. Another preferred class of salts of the compound of the present disclosure is represented by the basic addition salts with basic amino acids such as arginine or lysine, or aminosugars such as glucosamine and the like.

The alkali and alkaline earth metal salts are prepared according to the usual procedures commonly employed for preparing metal salts. As an example, lantibiotics according to the present disclosure, in the acid form or in the inner salt form, are dissolved into the minimum amount of a suitable solvent, typically a lower alkanol, or a lower alkanol water mixture, the stoichiometric amount of a suitable selected base is gradually added to the obtained solution and the obtained salt is precipitated by the addition of a non-solvent. The alkali or alkaline earth metal salt, which forms are then recovered by filtration or evaporation of the solvents.

Alternatively, these salts can be prepared in a substantially anhydrous form through lyophilization; in this case aqueous solutions containing the desired salts, resulting from the salification of the compounds according to the disclosure with a suitably selected alkali or alkaline earth metal carbonate or hydroxide in such a quantity as to obtain a pH comprised between and are filtered from any non soluble and lyophilized.

The organic ammonium salts can be prepared according to the above procedure by adding the properly selected amine to a solution of compounds in a suitable solvent and then evaporating off the solvent and the excess of the amine reagent or by lyophilizing the concentrate solution.

The addition salts of compounds encompassed herein with acids can be also prepared. Representative and suitable acid addition salts of the compounds of the disclosure include those salts formed by standard reaction with both organic and inorganic acids such as, for example, hydrochloric, hydrobromic, sulfuric, phosphoric, acetic, trifluoroacetic, trichloroacetic, succinic, citric, ascorbic, lactic, maleic, fumaric, palmitic, cholic, pamoic, mucic, glutamic, camphoric, glutaric, glycolic, phthalic, tartaric, lauric, stearic, salicylic, methanesulfonic, benzenesulfonic, sorbic, picric, benzoic, cinnamic and the like acids. The addition salts of the above mentioned compounds with acids can be prepared in a substantially analogues manner as that employed for the preparation of the salts with bases but using the appropriately selected acid as reagent in the place of the base.

As known in the art, the salt formation with either pharmaceutically or non-pharmaceutically acceptable acids may be used as a convenient purification technique. After formation and isolation, the salt form of a compound of formula (I) can be transformed into the corresponding non-salt or into a pharmaceutically acceptable salt. In some instances the acid addition salt of a compound of formula (I) is more soluble in water and hydrophilic solvents and has an increased chemical stability. Good solubility and stability in water or hydrophilic solvents of an active compound are in general appreciated in the art, for the preparation of suitable pharmaceutical compositions for the administration of the medicament. However, in view of the similarity of the properties of the compounds of formula (I) with their salts, what is said in the present application when dealing with the biological activities of the non-salt compounds of formula (I) applies also to their pharmaceutically acceptable salts, and vice versa.

The compounds encompassed herein can be administered orally, topically or parenterally, the preferred route of administration depending on the treatment to be carried out. Depending on the route of administration, these compounds can be formulated into various dosage forms. Preparations for oral administration may be in the form of capsules, tablets, liquid solutions or suspensions. As known in the art, the capsules and tablets may contain in addition to the active ingredient conventional excipients such as diluents e.g. lactose, calcium phosphate, sorbitol and the like lubricants e.g. magnesium stearate, talc, polyethylene glycol, binding agents, e.g. polyvinylpyrrolidone, gelatin, sorbitol, tragacanth, acacia, flavoring agents, and acceptable disintegrating and wetting agents. The liquid preparations generally in the form of aqueous or oily solutions or suspensions may contain conventional additives such as suspending agents. For topical use, the compounds of formula (I) of the present disclosure may also be prepared in suitable forms for absorption through the mucous membranes of the nose and throat or bronchial tissues and may conveniently take the form of liquid sprays or inhalants lozenges or throat paints. For medication of the eyes, the preparation may be presented in liquid or semi-liquid form. Topical applications may be formulated in hydrophobic or hydrophilic bases as ointments, creams, lotions, paints, or powders. For rectal administration the compounds of formula (I) of the disclosure are administered in the form of suppositories admixed with conventional vehicles, such as, for example, cocoa butter, wax, spermaceti or polyethylenglycols and their derivatives. Compositions for injection may take such forms as suspensions, solutions, or emulsions in oily or aqueous vehicles, and may contain formulation agents such as suspending, stabilizing and/or dispersing agents. Alternatively, the active ingredient may be in powder form for reconstitution at the time of delivery with a suitable vehicle, such as sterile water. The amount of active principle to be administered depends on various factors such as the size and conditions of the subject to be treated, the route and frequency of administration, and the causative agent involved.

The compounds encompassed herein are generally effective at a dosage comprised between about 1 and 40 mg of active ingredient per Kg of body weight. Depending on the characteristics of the specific compound, the infection and the patients, the effective dose can be administered in a single administration per day or divided in 2 to 4 administrations per day. Particularly desirable compositions are those prepared in the form of dosage units containing from about 30 to about 500 mg per unit.

The compounds encompassed herein can also be employed in combination with other drugs, being that another antibacterial agent or an agent intended to treat a second symptom or the cause of a different condition. For example, the antibacterial agents that can be used in conjunction with the compounds of the present disclosure include but are not limited to penicillins, cephalosporins, aminoglycosides, glycopeptides, rifamycins, lipopeptides, aminoglycosides. Therefore, compositions of the compounds of the present disclosure with other approved drugs fall also within the scope of the present disclosure.

The novel compounds of formula (I) encompassed herein, including salts, formulation and compositions thereof, can be effectively employed as the active ingredients of the antimicrobial preparations used in human or animal medicine for the prevention and treatment of infectious diseases caused by gram positive aerobic and anaerobic bacteria, such as *Enterococcus* sp., *Streptococcus* sp., *Staphylococcus* sp., *Clostridium* sp., including strains resistant to commonly used antibiotics.

The compounds encompassed herein, i.e. particularly lantibiotics NAI-857, NAI-130, NAI-114 or NAI-438 as well as their derivatives, are advantageously used as antibacterial agents against gram positive aerobic and anaerobic bacteria, such as *Enterococcus* sp., *Streptococcus* sp., *Staphylococcus* sp., *Clostridium* sp. in infectious diseases.

The disclosure also encompasses the use of a compound or composition thereof for the manufacture of a medicament for use in a specific method of treatment or prophylaxis of the human or animal body.

According to one embodiment, compounds of formula (I) are for example added to animal feed. This is preferably accomplished by preparing an appropriate feed premix containing the active compound in an effective amount and incorporating the premix into the complete ration. Alternatively, an intermediate concentrate or feed supplement containing the active ingredient can be blended into the feed.

The way in which such feed premixes and complete rations can be prepared and administered are described in reference books such as "Applied Animal Nutrition", W.H. Freedman and CO., S. Francisco, U.S.A., 1969 or "Livestock Feeds and Feeding" 0 and B books, Corvallis, Ore., U.S.A., 1977.

STRAINS AND FERMENTATION

Figure 1:
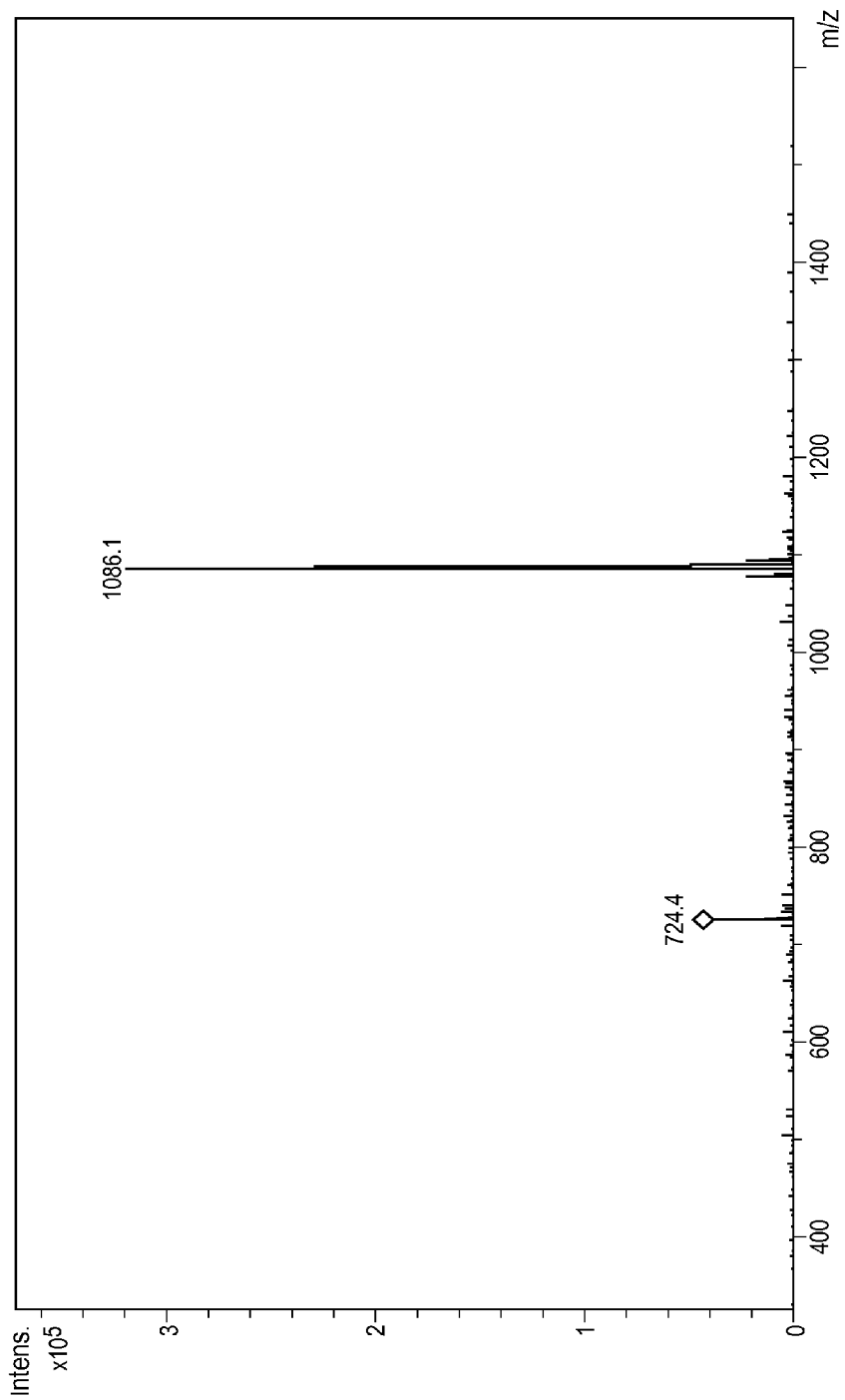
FIG. 1 and FIG. 2 represent mass spectra (full-scan low resolution spectrum) of antibiotic NAI-857 showing a doubly protonated ion at m/z 1086.

Encompassed herein is a process for the preparation of compounds of formula (I) comprising:
  cultivating at least one of an Actinomycetales sp. chosen among *Streptomyces* sp. DSM 24056, *Streptomyces* sp. DSM 24058, *Streptosporangium* sp. DSM 24060 and *Streptomyces* sp. DSM 24069 or a variant or mutant thereof maintaining the ability to produce lantibiotic of formula (I), under aerobic conditions, in an aqueous nutrient medium containing an assimilable source of carbon, nitrogen and inorganic salts;
  isolating the resulting lantibiotic of formula (I) from the whole culture broth, or from the separated mycelium or from the filtered fermentation broth;
  purifying the isolated lantibiotic of formula (I).

In an embodiment, the production of lantibiotic NAI-857 is achieved by cultivating a *Streptomyces* sp. strain capable of producing it, i.e. *Streptomyces* sp. DSM 24069 or a variant or mutant thereof maintaining the ability to produce lantibiotic NAI-857, isolating the resulting lantibiotic from the whole culture broth and/or from the separated mycelium and/or from the filtered fermentation broth, and purifying the isolated lantibiotic by chromatographic means.

In an embodiment, the production of lantibiotic NAI-130 is achieved by cultivating a *Streptomyces* sp. strain capable of producing it, i. e. *Streptomyces* sp. DSM 24058 or a variant or mutant thereof maintaining the ability to produce lantibiotic NAI-130, isolating the resulting lantibiotic from the whole culture broth and/or from the separated mycelium and/or from the filtered fermentation broth, and purifying the isolated lantibiotic by chromatographic means.

In an embodiment, the production of lantibiotic NAI-114 is achieved by cultivating a *Streptosporangium* sp. strain capable of producing it, i. e. *Streptosporangium* sp. DSM 24060 or a variant or mutant thereof maintaining the ability to produce lantibiotic NAI-114, isolating the resulting lantibiotic from the whole culture broth and/or from the separated mycelium and/or from the filtered fermentation broth, and purifying the isolated lantibiotic by chromatographic means.

In an embodiment, the production of lantibiotic NAI-438 is achieved by cultivating a *Streptomyces* sp. strain capable of producing it, i. e. *Streptomyces* sp. DSM 24056 or a variant or mutant thereof maintaining the ability to produce lantibiotic NAI-438, isolating the resulting lantibiotic from the whole culture broth and/or from the separated mycelium and/or from the filtered fermentation broth, and purifying the isolated lantibiotic by chromatographic means.

According to one preferred embodiment, the production of lantibiotic NAI-857 (or NAI-130, NAI-114, NAI-438) is carried out under aerobic conditions in an aqueous nutrient medium containing easy digestible or usable sources of carbon, nitrogen, and inorganic salts. Many of the nutrient media usually employed in fermentation field can be used, however preferred carbon sources are starch, dextrin, glucose, maltose, glycerol, and the like. Preferred nitrogen sources are soybean meal, peptone, meat extract, hydrolyzed casein, tryptone, corn steep liquor, cottonseed meal, yeast extract, and the like.

Soluble salts capable of yielding sodium, potassium, iron, zinc, cobalt, magnesium, calcium, ammonium, chloride, carbonate, sulphate, phosphate, nitrate, and the like ions can be incorporated in certain media.

In a preferred embodiment, the strain producing antibiotic NAT-857 (or NAI-130, NAI-114, NAI-438) is pre-cultured in a fermentation tube or in a shake flask, then the culture is used to inoculate jar reactors for fermentation for the production of substantial quantities of substances. The medium used for the pre-culture can be the same as that employed for larger fermentations, but other media can also be employed.

According to one preferred aspect, *Streptomyces* sp. DSM 24069 (or *Streptomyces* sp. DSM 24058, *Streptosporangium* sp. DSM 24060, *Streptomyces* sp. DSM 24056) strain is grown on S1 plates (detailed information are described in Experimental part—Example 1). On this medium strain *Streptomyces* sp. DSM 24069 forms grey colonies with light grey-white aerial mycelium. A light brown pigment is released in the medium with ageing of the cultures.

On S1 plates *Streptomyces* sp. DSM 24058 strain forms brown colonies with white aerial mycelium. A dark brown pigment is released in the medium.

On S1 plates *Streptosporangium* sp. DSM 24060 strain forms light orange to light pink colonies with patches of whitish aerial mycelium.

On S1 plates *Streptomyces* sp. DSM 24056 strain forms white-cream colonies with aerial mycelium of the same color.

The temperature for growing strain *Streptomyces* sp. DSM 24069 (or *Streptomyces* sp. DSM 24058, *Streptosporangium* sp. DSM 24060, *Streptomyces* sp. DSM 24056) producing antibiotic NAI-857 (or NAI-130, NAI-114, NAI-438) is 26-35° C., preferably 28-32° C. During the fermentation, antibiotic NAI-857 (or NAI-130, NAI-114, NAI-438) production can be monitored by bioassay on susceptible microorganisms and/or by HPLC analyses. Maximum production of antibiotic NAI-857 (or NAI-130, NAT-114, NAI-438) generally occurs after 72 hours and before 192 hours of fermentation.

Antibiotic NAI-857 (or NAI-130, NAI-114, NAT-438) is thus produced by cultivating *Streptomyces* sp. DSM 24069 (or *Streptomyces* sp. DSM 24058, *Streptosporangium* sp. DSM 24060, *Streptomyces* sp. DSM 24056) or a variant or mutant thereof capable of producing antibiotic NAI-857 (or NAI-130, NAI-114, NAI-438), and it is found in the culture broths and/or in the mycelium.

*Streptomyces* sp. DSM 24069 16S rRNA Gene SEQUENCE

The partial sequence of the 16 rRNA gene (16S rDNA), i.e 644 nucleotides, of strain *Streptomyces* sp. DSM 24069 is reported in SEQ ID No. 1. This sequence is compared with those deposited in public databases, and is found to be related to the 16S rRNA gene sequences of various *Streptomyces* strains.

As with other microorganisms, the characteristics of strain producing antibiotic NAI-857 are subject to variation. For example, artificial variants and mutants of the strain can be obtained by treatment with various known mutagens, such as U.V. rays, and chemicals such as nitrous acid, N-methyl-N'-nitro-N-nitrosoguanidine, and many others. All natural and artificial variants and mutants of strain *Streptomyces* sp. DSM 24069 are capable of producing antibiotic NAI-857.

```
(16S rRNA gene of strain Streptomyces sp. DSM 24069)
                                                          SEQ_ID No. 1
     1    ATGGCTCAGG ACGAACGCTG GCGGCGTGCT TAACACATGC AAGTCGAACG

51    ATGAACCACT TCGGTGGGGA TTAGTGGCGA ACGGGTGAGT AACACGTGGG

101    CAATCTGCCC TGCACTCTGG GACAAGCCCT GGAAACGGGG TCTAATACCG

151    GATACAACCA CTAGGGGCAT CCCTCGGTGG TGGAAAGCTC CGGCGGTGCA

201    GGATGAGCCC GCGGCCTATC AGCTTGTTGG TGAGGTAACG GCTCACCAAG

251    GCGACGACGG GTAGCCGGCC TGAGAGGGCG ACCGGCCACA CTGGGACTGA

301    GACACGGCCC AGACTCCTAC GGGAGGCAGC AGTGGGGAAT ATTGCACAAT

351    GGGCGAAAGC CTGATGCAGC GACGCCGCGT GAGGGATGAC GGCCTTCGGG

401    TTGTAAACCT CTTTCAGCAG GGAAGAAGCG AAAGTGACGG TACCTGCAGA
```

```
451  AGAAGCGCCG GCTAACTACG TGCCAGCAGC CGCGGTAATA CGTAGGGCGC

501  AAGCGTTGTC CGGAATTATT GGGCGTAAAG AGCTCGTAGG CGGCTTGTCG

551  CGTCGGTTGT GAAAGCCCGG GGCTTAACCC CGGGTCTGCA GTCGATACGG

601  GCAGGCTAGA GTCGGTAAGG GGAGATCGGA ATTCCTGGTG TAAC
```

*Streptomyces* sp. DSM 24058 16S rRNA Gene SEQUENCE

The partial sequence of the 16 rRNA gene (16S rDNA), i.e 1342 nucleotides, of strain *Streptomyces* sp. DSM 24058 is reported in SEQ ID No. 2. This sequence is compared with those deposited in public databases, and is found to be related to the 16S rRNA gene sequences of various *Streptomyces* strains.

As with other microorganisms, the characteristics of strain producing antibiotic NAI-130 are subject to variation. For example, artificial variants and mutants of the strain can be obtained by treatment with various known mutagens, such as U.V. rays, and chemicals such as nitrous acid, N-methyl-N-nitro-N-nitrosoguanidine, and many others. All natural and artificial variants and mutants of strain *Streptomyces* sp. DSM 24058 are capable of producing antibiotic NAI-130.

```
(16S rRNA gene of strain Streptomyces sp. DSM 24058)
                                                   SEQ_ID No. 2
   1  ATCATGGCTC AGGACGAACG CTGGCGGCGT GCTTAACACA TGCAAGTCGA

51  ACGATGAACC ACTTCGGTGG GGATTAGTGG CGAACGGGTG AGTAACACGT

101  GGGCAATCTG CCCTGCACTC TGGGACAAGC CCTGGAAACG GGTCTAATA

151  CCGGATACAA CCACTGACCG CATGGTCGGG TGGTGGAAAG CTCCGGCGGT

201  GCAGGATGAG CCCGCGGCCT ATCAGCTTGT TGGTGAGGTA ATGGCTCACC

251  AAGGCGACGA CGGGTAGCCG GCCTGAGAGG GCGACCGGCC ACACTGGGAC

301  TGAGACACGG CCCAGACTCC TACGGGAGGC AGCAGTGGGG AATATTGCAC

351  AATGGGCGCA AGCCTGATGC AGCGACGCCG CGTGAGGGAT GACGGCCTTC

401  GGGTTGTAAA CCTCTTTCAG CAGGGAAGAA GCGAAAGTGA CGGTACCTGC

451  AGAAGAAGCG CCGGCTAACT ACGTGCCAGC AGCCGCGGTA ATACGTAGGG

501  CGCAAGCGTT GTCCGGAATT ATTGGGCGTA AAGAGCTCGT AGGCGGCTTG

551  TCGCGTCGGT TGTGAAAGCC CGGGGCTTAA CCCCGGGTCT GCAGTCGATA

601  CGGGCAGGCT AGAGTTCGGT AGGGGAGATC GGAATTCCTG GTGTAGCGGT

651  GAAATGCGCA GATATCAGGA GGAACACCGG TGGCGAAGGC GGATCTCTGG

701  GCCGATACTG ACGCTGAGGA GCGAAAGCGT GGGGAGCGAA CAGGATTAGA

751  TACCCTGGTA GTCCACGCCG TAAACGGTGG GCACTAGGTG TGGGCGACAT

801  TCCACGTCGT CCGTGCCGCA GCTAACGCAT TAAGTGCCCC GCCTGGGGAG

851  TACGGCCGCA AGGCTAAAAC TCAAAGGAAT TGACGGGGGC CCGCACAAGC

901  GGCGGAGCAT GTGGCTTAAT TCGACGCAAC GCGAAGAACC TTACCAAGGC

951  TTGACATACA CCGGAAACGT CTGGAGACAG GCGCCCCCTT GTGGTCGGTG

1001  TACAGGTGGT GCATGGCTGT CGTCAGCTCG TGTCGTGAGA TGTTGGGTTA

1051  AGTCCCGCAA CGAGCGCAAC CCTTGTCCCG TGTTGCCAGC AGGCCCTTGT

1101  GGTGCTGGGG ACTCACGGGA GACCGCCGGG GTCAACTCGG AGGAAGGTGG

1151  GGACGACGTC AAGTCATCAT GCCCCTTATG TCTTGGGCTG CACACGTGCT

1201  ACAATGGCCG GTACAATGAG CTGCGATACC GCGAGGTGGA GCGAATCTCA

1251  AAAAGCCGGT CTCAGTTCGG ATTGGGGTCT GCAACTCGAC CCCATGAAGT

1301  CGGAGTCGCT AGTAATCGCA GATCAGCATT GCTGCGGTGA AT
```

Streptosporangium sp. DSM 24060 16S rRNA Gene SEQUENCE

The partial sequence of the 16 rRNA gene (16S rDNA), i.e 1425 nucleotides, of strain *Streptosporangium* sp. DSM 24060 is reported in SEQ ID No. 3. This sequence is compared with those deposited in public databases, and is found to be related to the 16S rRNA gene sequences of various *Streptosporangium* strains.

As with other microorganisms, the characteristics of strain producing antibiotic NAI-114 are subject to variation. For example, artificial variants and mutants of the strain can be obtained by treatment with various known mutagens, such as U.V. rays, and chemicals such as nitrous acid, N-methyl-N'-nitro-N-nitrosoguanidine, and many others. All natural and artificial variants and mutants of strain *Streptosporangium* sp. DSM 24060 are capable of producing antibiotic NAI-114.

(16S rRNA gene of strain *Streptosporangium* sp. DSM 24060)
SEQ_ID No. 3

```
   1   CGGCGTGCTT AACACATGCA AGTCGAGCGG AAAGGCCCTT CGGGGTACTC
  51   GAGCGGCGAA CGGGTGAGTA ACACGTGAGT AACCTGCCCC TGACTCTGGG
 101   ATAAGCCCGG GAAACTGGGT CTAATACCGG ATACGACCAC TTCCCGCATG
 151   GGATGGTGGT GGAAAGTTTT TCGGTCGGGG ATGGGCTCGC GGCCTATCAG
 201   CTTGTTGGTG GGGTAGTGGC CTACCAAGGC GACGACGGGT AGCCGGCCTG
 251   AGAGGGCGAC CGGCCACACT GGGACTGAGA CACGGCCCAG ACTCCTACGG
 301   GAGGCAGCAG TGGGGAATAT TGCGCAATGG GCGAAAGCCT GACGCAGCGA
 351   CGCCGCGTGG GGGATGACGG CCTTCGGGTT GTAAACCTCT TTCAGCAGGG
 401   ACGAAGTTGA CGTGTACCTG CAGAAGAAGC GCCGGCTAAC TACGTGCCAG
 451   CAGCCGCGGT AATACGTAGG GCGCAAGCGT TGTCCGGAAT TATTGGGCGT
 501   AAAGAGCTCG TAGGTGGCTT GTCGCGTCGG GTGTGAAAGC TTGGGGCTTA
 551   ACTCCAGGTC TGCATTCGAT ACGGGCTGGC TAGAGGTAGG TAGGGAGAA
 601   CGGAATTCCT GGTGTAGCGG TGAAATGCGC AGATATCAGG AGGAACACCG
 651   GTGGCGAAGG CGGTTCTCTG GGCCTTACCT GACGCTGAGG AGCGAAAGCG
 701   TGGGGAGCGA ACAGGATTAG ATACCCTGGT AGTCCACGCT GTAAACGTTG
 751   GGCGCTAGGT GTGGGACCT TCCACGGTTT CCGCGCCGTA GCTAACGCAT
 801   TAAGCGCCCC GCCTGGGGAG TACGGCCGCA AGGCTAAAAC TCAAAGGAAT
 851   TGACGGGGGC CCGCACAAGC GGCGGAGCAT GTTGCTTAAT TCGACGCAAC
 901   GCGAAGAACC TTACCAAGGC TTGACATCGC CCGGAAAGCT TCAGAGATGG
 951   AGCCCTCTTC GGACTGGGTG ACAGGTGGTG CATGGCTGTC GTCAGCTCGT
1001   GTCGTGAGAT GTTGGGTTAA GTCCCGCAAC GAGCGCAACC CTTGTTCCAT
1051   GTTGCCAGCA CGCCCCTTTG GGGGTGGTGG GGACTCATGG GAGACTGCCG
1101   GGGTCAACTC GGAGGAAGGT GGGGATGACG TCAAGTCATC ATGCCCCTTA
1151   TGTCTTGGGC TGCAAACATG CTACAATGGC CGGTACAGAG GGTTGCGATA
1201   CCGTGAGGTG GAGCGAATCC CTAAAAGCCG GTCTCAGTTC GGATTGGGGT
1251   CTGCAACTCG ACCCCATGAA GTCGGAGTCG CTAGTAATCG CAGATCAGCA
1301   ACGCTGCGGT GAATACGTTC CCGGGCCTTG TACACACCGC CCGTCACGTC
1351   ACGAAAGTCG GCAACACCCG AAGCCCGTGG CCCAACCAGC TTGCTGGGGG
1401   GAGCGGTCGA AGGTGGGGCT GGCGA
```

Streptomyces sp. DSM 24056 16S rRNA Gene SEQUENCE

The partial sequence of the 16 rRNA gene (16S rDNA), i.e 1448 nucleotides, of strain *Streptomyces* sp. DSM 24056 is reported in SEQ ID No.4. This sequence is compared with those deposited in public databases, and is found to be related to the 16S rRNA gene sequences of various *Streptomyces* strains.

As with other microorganisms, the characteristics of strain producing antibiotic NAI-438 are subject to variation. For example, artificial variants and mutants of the strain can be obtained by treatment with various known mutagens, such as U.V. rays, and chemicals such as nitrous acid, N-methyl-N'-nitro-N-nitrosoguanidine, and many others. All natural and artificial variants and mutants of strain *Streptomyces* sp. DSM 24056 are capable of producing antibiotic NAI-438.

```
(16S rRNA gene of strain Streptomyces sp. DSM 24056)
                                                       SEQ_ID No. 4
    1  GACGAACGCT GGCGGCGTGC TTAACACATG CAAGTCGAAC GATGAAGCCC
   51  TTTCGGGGGT GGATTAGTGG CGAACGGGTG AGTAACACGT GGGCAATCTG
  101  CCCTGCACTT CGGGACAAGC CCTGGAAACG GGGTCTAATA CCGGATACAA
  151  CTCCCTTGGG CATCCTTGGG GGTGAAAGC  TTCGGCGGTG CAGGATGAGC
  201  CCGCGGCCTA TCAGCTTGTT GGTGGGGTGA TGGCCTACCA AGGCGACGAC
  251  GGGTAGCCGG CCTGAGAGGG CGACCGGCCA CACTGGGACT GAGACACGGC
  301  CCAGACTCCT ACGGGAGGCA GCAGTGGGGA ATATTGCACA ATGGGCGAAA
  351  GCCTGATGCA GCGACGCCGC GTGAGGGATG ACGGCCTTCG GGTTGTAAAC
  401  CTCTTTCAGC AGGGAAGAAG CGAGAGTGAC GGTACCTGCA GAAGAAGCAC
  451  CGGCTAACTA CGTGCCAGCA GCCGCGGTAA TACGTAGGGT GCGAGCGTTG
  501  TCCGGAATTA TTGGGCGTAA AGAGCTCGTA GGCGGCCTGT CACGTCGGAT
  551  GTGAAAGCCC GGGGCTTAAC CCTGGGTCTG CATTCGATAC GGGCAGGCTA
  601  GAGTTCGGTA GGGGAGATCG GAATTCCTGG TGTAGCGGTG AAATGCGCAG
  651  ATATCAGGAG GAACACCGGT GGCGAAGGCG GATCTCTGGG CCGATACTGA
  701  CGCTGAGGAG CGAAAGCATG GGGAGCGAAC AGGATTAGAT ACCCTGGTAG
  751  TCCATGCCGT AAACGTTGGG CACTAGGTGT GGGCGACATT CCACGTTGTC
  801  CGTGCCGCAG CTAACGCATT AAGTGCCCCG CCTGGGGAGT ACGGCCGCAA
  851  GGCTAAAACT CAAAGGAATT GACGGGGGCC CGCACAAGCG GCGGAGCATG
  901  TGGCTTAATT CGACGCAACG CGAAGAACCT TACCAAGGCT TGACATACAC
  951  CAGAAAGCTG TGGAGACACA GCCCCCCTTG TGGTTGGTGT ACAGGTGGTG
 1001  CATGGCTGTC GTCAGCTCGT GTCGTGAGAT GTTGGGTTAA GTCCCGCAAC
 1051  GAGCGCAACC CTTATCCTGT GTTGCCAGCA ACTCTTCGGA GGTTGGGGAC
 1101  TCACGGAGA  CTGCCGGGGT CAACTCGGAG GAAGGTGGGG ACGACGTCAA
 1151  GTCATCATGC CCCTTATGTC TTGGGCTGCA CACGTGCTAC AATGGCCGGT
 1201  ACAATGAGTT GCGATGCCGT GAGGTGGAGC GAATCTCAAA AAGCCGGTCT
 1251  CAGTTCGGAT TGGGGTCTGC AACTCGACCC CATGAAGTCG GAGTCGCTAG
 1301  TAATCGCAGA TCAGCATTGC TGCGGTGAAT ACGTTCCCGG GCCTTGTACA
 1351  CACCGCCCGT CACGTCACGA AAGTCGGTAA CACCCGAAGC CGGTGGCCCA
 1401  ACCCCTCGTG GGAGGGAGCC GTCGAAGGTG GGACTGGCGA TTGGGACG
```

Extraction and Purification of Lantibiotics of Formula (I)

Preferred compounds NAI-857, NAI-130, NAI-438, NAI-114 are distributed both in the mycelium and in the filtered fraction of the fermentation broth. The harvested broth is processed to separate the mycelium from the supernatant of the fermentation broth and the mycelium is extracted with a water-miscible solvent to obtain a solution containing the lantibiotic, after removal of the spent mycelium. This mycelium extract is then processed separately or in pool with the supernatant according to the procedures reported hereafter for the supernatant fraction. When the water-miscible solvent would cause interferences with the operations for recovering the lantibiotic from the mycelium extract, the water-miscible solvent is removed by distillation or is diluted with water to a non-interfering concentration.

As used herein the term "water-miscible solvent" refers to solvents that, at the conditions of use, are miscible with water in a reasonably wide concentration range. Examples of water-miscible organic solvents that can be used in the extraction of the compounds of the disclosure are: lower alkanols, e.g. (C1-C3) alkanols such as methanol, ethanol, and propanol, phenyl (C1-C3) alkanols such as benzyl alcohol; lower ketones, e. g. (C1-C4) ketones such as acetone and ethyl methyl ketone; cyclic ethers such as dioxane and tetrahydrofuran; glycols and their products of partial etherification such as ethylene glycol, propylene glycol, and ethylene glycol monomethyl ether, lower amides such as dimethylformamide and diethylformamide; acetic acid dimethylsulfoxide and acetonitrile.

The recovery of the compound from the supernatant of the fermentation broth of the producing microorganism is conducted according to known per se techniques which include extraction with solvents, precipitation by adding non-solvents or by changing the pH of the solution, by partition chromatography, reverse phase partition chromatography, ion exchange chromatography, molecular exclusion chromatography and the like or a combination of two or more of said techniques. A procedure for recovering the compounds of the disclosure from the filtered fermentation broth includes extraction of a compound chosen among NAI-857, NAI-130, NAI-438 or NAI-114 with water-immiscible organic solvents, followed by precipitation from the concentrated extracts, possibly by adding a precipitating agent.

As used herein the term "water-immiscible solvent" refers to solvents that, at the conditions of use, are slightly miscible or practically immiscible with water in a reasonably wide concentration range, suitable for the intended use. Examples of water-immiscible organic solvents that can be used in the extraction of the compounds of the disclosure from the fermentation broth are: alkanols of at least four carbon atoms which may be linear, branched or cyclic such as n-butanol, 1-pentanol, 2-pentanol, 3-pentanol, 1-hexanol, 2-hexanol, 3-hexanol, 3,3-dimethyl-1-butanol, 4-methyl-1-pentanol, 3-methyl-1-pentanol, 2,2-dimethyl-3-pentanol, 2,4-dimethyl-3-pentanol, 4,4-dimethyl2-pentanol, 5-methyl-2-hexanol, 1-heptanol, 2-heptanol, 5methyl-1-hexanol, 2-ethyl-1-hexanol, 2-methyl-3-hexanol, 1octanol, 2-octanol, cyclopentanol, 2-cyclopentylethanol, 3-cyclopenthyl-1-propanol, cyclohexanol, cycloheptanol, cyclooctanol, 2,3-dimethyl-cyclohexanol,4-ethylcyclohexanol, cyclooctylmethanol, 6-methyl-5-hepten-2-01, 1-nonanol, 2nonanol, 1-decanol, 2-decanol, and 3-decanol; ketones of at least five carbon atoms such as methylisopropylketone, methyl isobutylketone, methyl-n-amylketone, methylisoamylketone and mixtures thereof.

As known in the art, product extraction from the filtered fermentation broth may be improved by adjusting the pH at an appropriate value, and/or by adding a proper organic salt forming an ion pair with the lantibiotic, which is soluble in the extraction solvent. As known in the art, phase separation may be improved by salting the aqueous phase.

When, following an extraction, an organic phase is recovered containing a substantial amount of water, it may be convenient to azeotropically distill water from it. Generally, this requires adding a solvent capable of forming minimum azeotropic mixtures with water, followed by the addition of a precipitating agent to precipitate the desired product, if necessary. Representative examples of organic solvents capable of forming minimum azeotropic mixtures with water are: n-butanol, benzene, toluene, butyl ether, carbon tetrachloride, chloroform, cyclohexane, 2,5-dimethylfuran, hexane, and mxylenei the preferred solvent being n-butanol. Examples of precipitating agents are petroleum ether, (C1-C4)alkyl ethers, such as ethyl ether, propyl ether, and butyl ether, and (C1-C4)alkyl ketones such as acetone.

According to a preferred procedure for recovering lantibiotic NAT-857, NAI-130, NAI-114 or NAI-438, the filtered fermentation broth can be contacted with an adsorption matrix followed by elution with a polar, water miscible solvent or a mixture thereof, concentration to an oily residue under reduced pressure, and precipitation with a precipitating agent of the type already mentioned above.

Examples of adsorption matrixes that can be conveniently used in the recovery of the compounds of the disclosure, are polystyrene or mixed polystyrene-divinylbenzene resins (e. g. M112 or 8112, Dow Chemical Co.; Amberlite® XAD2 or XAD4, Rohm & Haasi Diaion HP 20, Mitsubishi), acrylic resins (e.g. XAD7 or XAD8, Rohm & Haas), polyamides such as polycaprolactames, nylons and cross-linked polyvinylpyrrolidones (e.g. Polyamide-CC 6, Polyamide-8C 6, Polyamide-CC 6.6, Polyamide-CC 6AC and Polyamide-SC 6AC, Macherey-Nagel & Co., Germany; PA 400,' M. Woelm AG, Germany); and the polyvinylpirrolidone resin PVPCL, (Aldrich Chemie GmbH & Co., KG, Germany) and controlled pore cross-linked dextrans (e.g. Sephadex® LH-20, Pharmacia Fine Chemicals, AB). Preferably polystyrene resins are employed, particularly preferred being the Diaion HP 20 resin. In the case of polystyrene resins, polystyrene-divinylbenzene resins, polyamide resins or acrylic resins a preferred eluent is a water-miscible solvent or its aqueous mixtures. The aqueous mixtures can contain buffers at appropriate pH value.

The successive procedures for the isolation and purification of the lantibiotic may be carried out on the pooled extracts from the broth supernatant and from the mycelium. For example, when the portion of the lantibiotic product contained in the filtered fermentation broth or supernatant is recovered by absorption on an absorption resin and the portion of the lantibiotic product contained in the mycelium is extracted therefrom with a water-miscible solvent, followed by adsorption onto an absorption resin, the eluted fractions from each of the two sets of absorption resins are combined, optionally after concentration, and then further processed as a unitary crop. Alternatively, when the two sets of absorption resins utilized for the separate extraction stages are of the same type and have the same functional characteristics, they are pooled together and the mixture may be submitted to a unitary elution step, for instance, with a water-miscible solvent or a mixture thereof with water. In any case, whatever the procedure adopted for recovering the lantibiotics NAI-857, NAI-130, NAI-114 or NAI-438, the successive purification step is usually carried out on the mixture of the crude materials resulting from the combination of the separate extraction stages.

Purification of the crude lantibiotics NAI-857, NAI-130, NAI-114 or NAI-438, can be accomplished by any of the known per se techniques but is preferably conducted by means of chromatographic procedures.

Examples of these chromatographic procedures are those reported in relation to the recovery step and include also chromatography on stationary phases such as silica gel, alumina, activated magnesium silicate and the like or reverse phase chromatography on silanized silica gel having various functional derivatizations, and eluting with water miscible solvents or aqueous mixture of water-miscible solvents of the kind mentioned above.

For instance, preparative HPLC or medium or low pressure liquid chromatography may be employed, using RP-8 or RP-18 as stationary phase and a mixture of $HCOONH_4$ buffer (or TFA 0.1%):$CH_3CN$ (or MeOH) as eluting system. The active fractions recovered from the purification step are pooled together, concentrated under vacuum, precipitated by addition of a precipitating agent of the kind mentioned above and dried or lyophilized in single or iterative rounds. In the case the product contains residual amounts of ammonium formate or other buffering salts, these may be removed by absorption of the lantibiotics NAI-857, NAI-130, NAI-114 or NAI-438, on solid phase extraction column, for instance a reverse phase resin column such as SPE Superclean LCP18 Supelco (Belle fonte Pa., USA) followed by washing with distilled water and elution with an appropriate aqueous solvent mixture, e. g. methanol:water. The lantibiotic is then recovered by removing the elution solvents.

Accordingly, purified lantibiotics NAI-857, NAI-130, NAI-114 or NAI-438 dried preparations are obtained as a white-beige powder. As usual in this art, the production as well as the recovery and purification steps may be monitored by a variety of procedures including inhibitory assay against susceptible microorganisms, HPLC or HPLC coupled with mass spectrometry.

HPLC method 1: A preferred analytical HPLC technique is performed on a Shimadzu instrument (LC 2010A-HT liquid chromatograph, Shimadzu Corporation, Japan) equipped with a column LiChrosphere RP18, 5μ (125×4.6 mm) eluted at 1 ml/min flow rate and at 50° C. temperature.

Elution is with a multistep program: Time=0 (10% phase B); Time=20 min (50% Phase B); Time=21 min (80% of phase B); Time=25 min (80% of phase B); Time=26 min (10% of phase B); Time=35 min (10% of phase B). Phase A is trifluoroacetic acid 0.1% in water (v/v) and Phase B is acetonitrile. UV detector is at 230 nm and 270 nm. In these analytical HPLC conditions the lantibiotics show the following retention times: NAI-857 14.8 minutes, NAI-130 13.3 minutes, NAI-114 16.7 minutes, NAI-438 14.4 minutes.

HPLC method 2: A preferred analytical HPLC-MS technique is performed on a Agilent 1100 series liquid chromatograph equipped with a column Ascentis express Supelco RP18, 2.7μ, (50×4.6 mm) eluted at 1 ml/min flow rate and at 40° C. temperature. Elution is with a multistep program: Time=0 (5% phase B); Time=6 min (95% Phase B); Time=7 min (100% phase B); Time=7.2 min (5% phase B); Time=10 min (5% phase B). Phase A is trifluoroacetic acid 0.05% in water (v/v) and phase B is trifluoroacetic acid 0.05% in acetonitrile (v/v). UV detector is at 220 nm.

The effluent from the column is splitted in a ratio 50:50 and one part (500 μL/min) is diverted to photodiode array detector. The remaining 500 μL/min are diverted to the ESI interface of a Bruker Esquire3000 plus ion trap mass spectrometer.

The mass spectrometric analysis is performed under the following conditions: sample inlet conditions: sheat gas ($N_2$) 50 psi; dry gas 10 L/min; capillary heater 365° C.; sample inlet voltage settings: polarity:positive; capillary voltage –4000V; end plate offset –500V; Scan conditions: maximum ion time 200 ms; ion time 5 ms; full micro scan 3; segment: duration 10 min, scan events positive (100-2400 m/z). In these analytical HPLC conditions the lantibiotics show the following retention times: NAI-857 3.3 minutes, NAI-130 3.5 minutes, NAI-114 4.1 minutes, NAI-438 3.5 minutes.

Physico-Chemical Characteristics of Antibiotic of Formula (I) NAI-857

Figure 2:
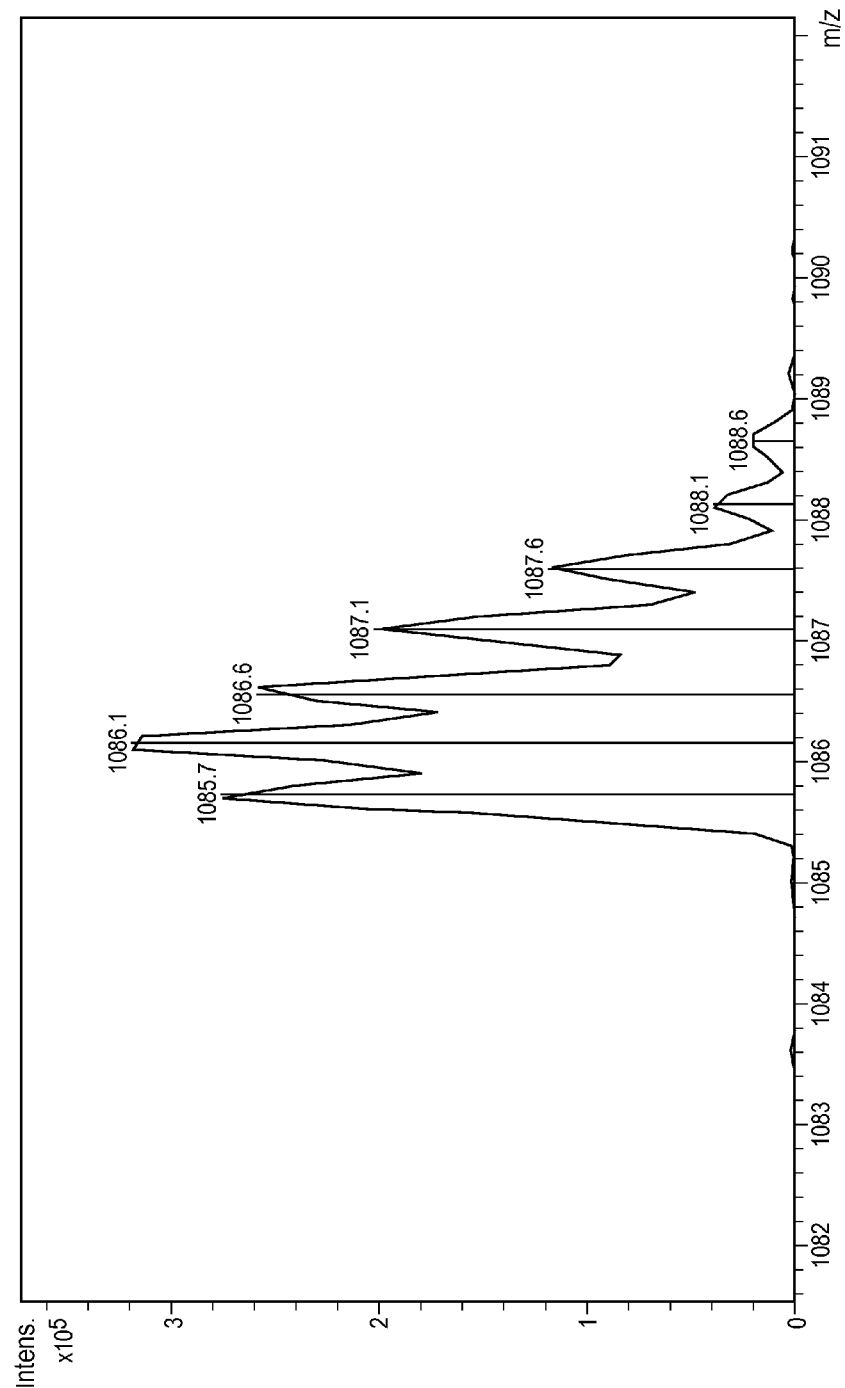

A) Mass spectrometry: in MS experiments on a Thermofinnigan LCQ deca instrument fitted with an electrospray source, using Thermofinnigan calibration mix, antibiotic NAI-857 gives a doubly protonated ion at 1086 m/z. MS/MS analysis of the double charged ion is performed with the observed main fragmentations: monocharged 1116, 1373, 1456, 1791 and double charged 1021 m/z. The electrospray conditions are: Spray Voltage: 4.7 kV; Capillary temperature: 220° C.; Capillary Voltage: 3 V; Infusion mode 10 μL/min. Spectra are recorded from a 0.2 mg/ml solution in methanol/water 80/20 (v/v) with trifluoroacetic acid 0.1% and are reported in FIG. 1 and FIG. 2 (full-scan low resolution spectrum).

Figure 3:
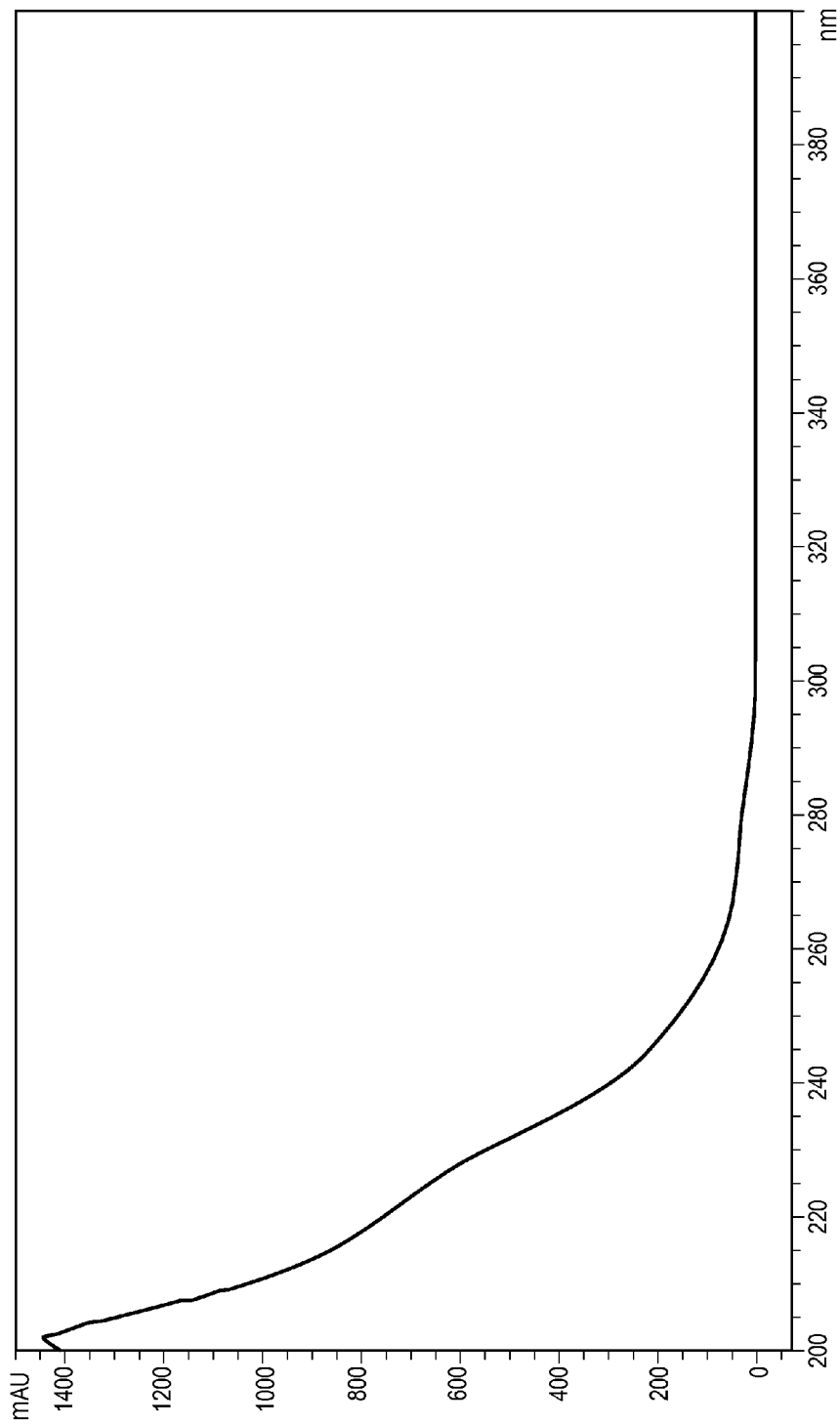
FIG. 3 represents the UV spectrum of antibiotic NAI-857 dissolved in Acetonitrile:TFA 0.1%=1:1

B) The U.V. spectrum of antibiotic NAI-857, performed in TFA 0.1%-acetonitrile (in ratio 50:50) with a Shimadzu Diode Array detector SPD-M10A VP (Shimadzu Corporation, Japan) during a HPLC analysis, exhibits two maxima at 225 and 280 nm. UV spectrum is reported in FIG. 3

C) $^1$H-NMR and 2D experiments are recorded in the mixtures $CD_3CN/D_2O$ (1/1) with and without the addition of 50 μL of $H_2O$ at 25° C. on a Bruker AMX 600 or 400 spectrometers. If necessary a water suppression sequence is applied.

Figure 4:
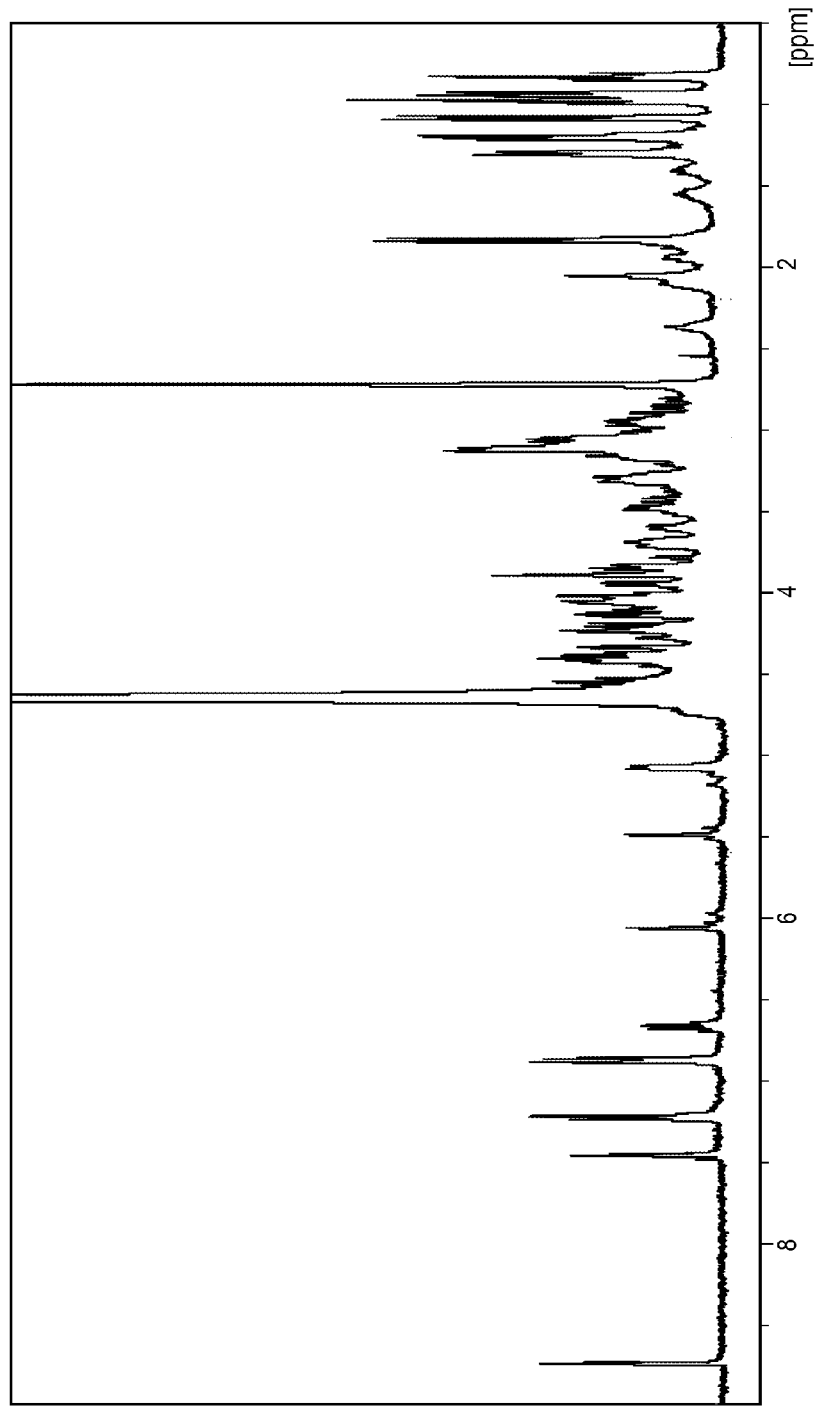
FIG. 4 represents the $^1$H-NMR spectrum of NAI-857 recorded in the mixture Acetonitrile-$d_3$:D20 at 25° C. on a Bruker AMX 400 spectrometer.

$^1$H NMR spectrum of antibiotic NAI-857 exhibits the following groups of signals [δ=ppm; multiplicity; (attribution)]: 0.90 t ($CH_3$), 1.00 d ($CH_3$), 1.04 t ($CH_3$), 1.15 d ($CH_3$), 1.27 d ($CH_3$), 1.37 d ($CH_3$), 1.89 d ($CH_3$), 1.25-1.47 m ($CH_2$), 1.35-1.62 m ($CH_2$), 1.91-1.98 m ($CH_2$), 1.87-2.42 m ($CH_2$), 2.9-3.76 (peptidic beta CH and $CH_2$), 3.83-5.14 (peptidic alpha CH and $CH_2$), 5.54-6.07 s ($CH_2$), 6.68 q (CH), 6.89-9.15 s, d and m (aromatic CH's and peptidic NH's). The $^1$H-NMR spectrum of NAI-857 is reported in FIG. 4.

Figure 5:
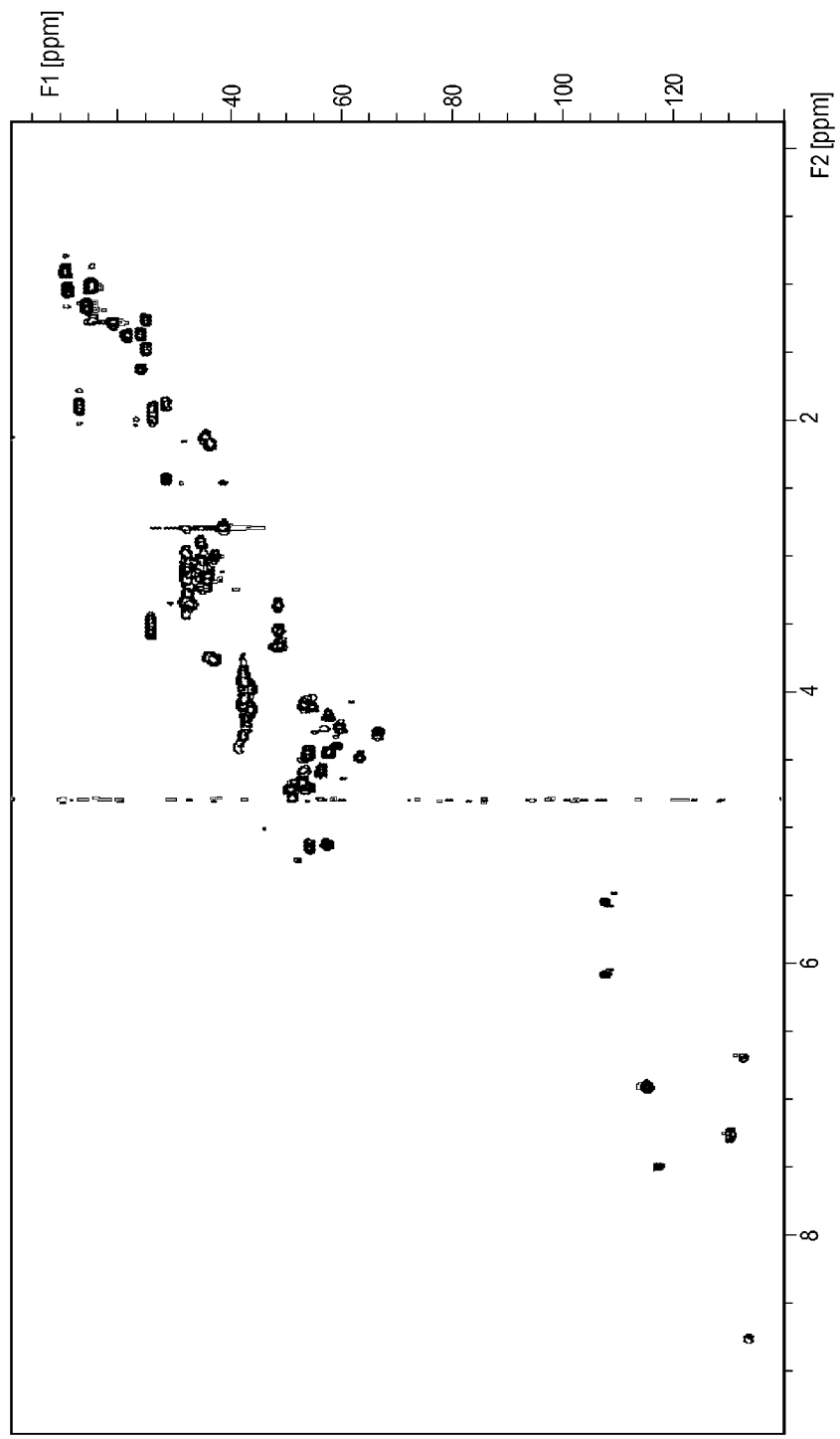
FIG. 5 and FIG. 6 represents the HSQC and HMBC NMR spectra of NAI-857 recorded in the mixture Acetonitrile-$d_3$:D20 at 25° C. on a Bruker AMX 600 spectrometer.
Figure 6:
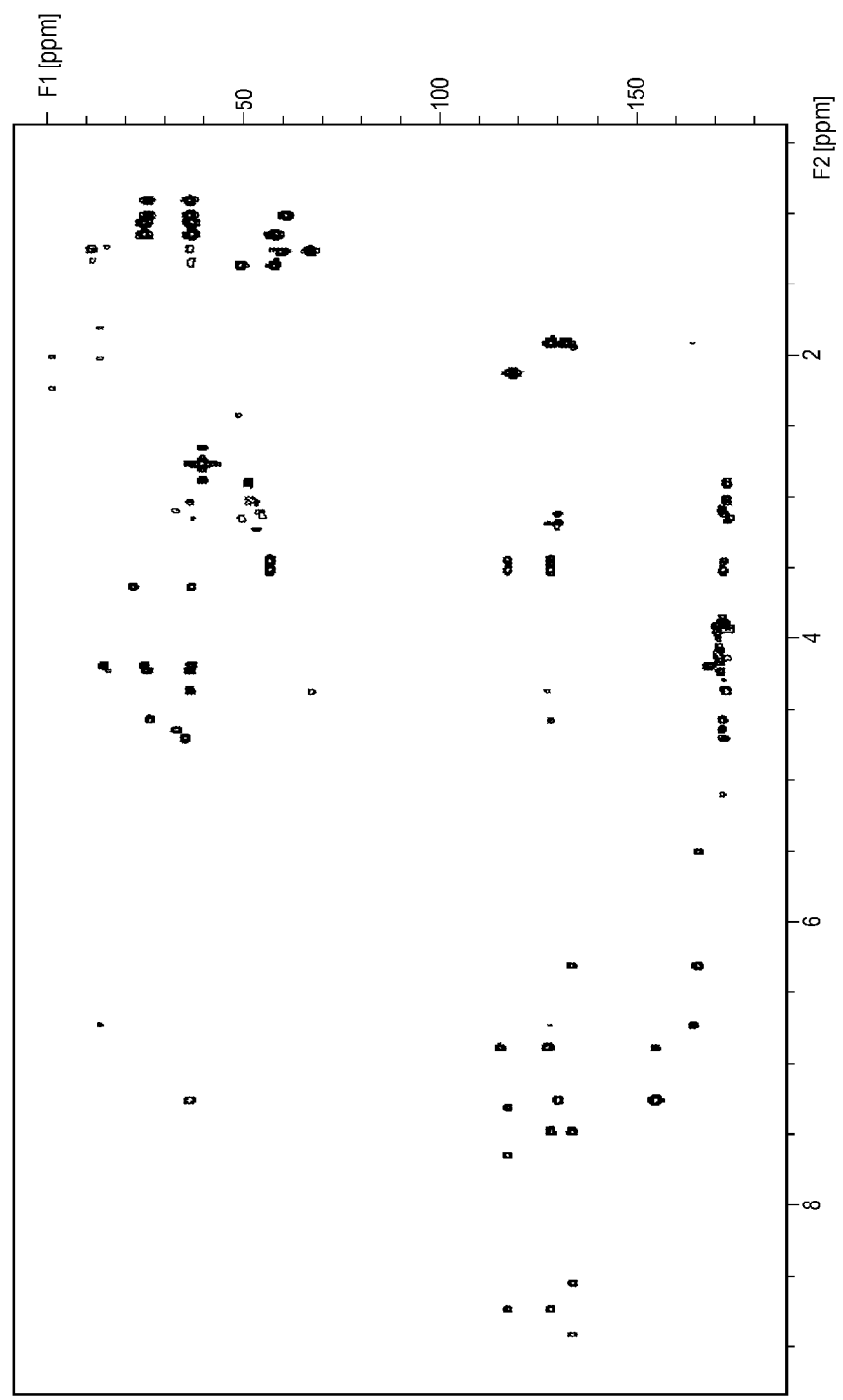

NAI-857 exhibits the following 13C groups of signals [δ=ppm; (attribution)]: 10.1-21.4 (aliphatic $CH_3$'s), 25.7-67.0 (aliphatic and peptidic signals), 108-157 (aromatic and double bonds CH's and quaternary carbons), 165-174 (peptidic carbonyls). HSQC and HMBC spectra of NAI-857 are reported in FIG. 5 and FIG. 6.

D) HPLC data: NAI-857 shows a retention time of 14.8 minutes when analysed with the HPLC method 1 as above described. NAI-857 shows a retention time of 3.3 minutes when analysed with HPLC method 2 as above described.

Physico-Chemical Characteristics of Antibiotic of Formula (I) NAI-130

Figure 7:
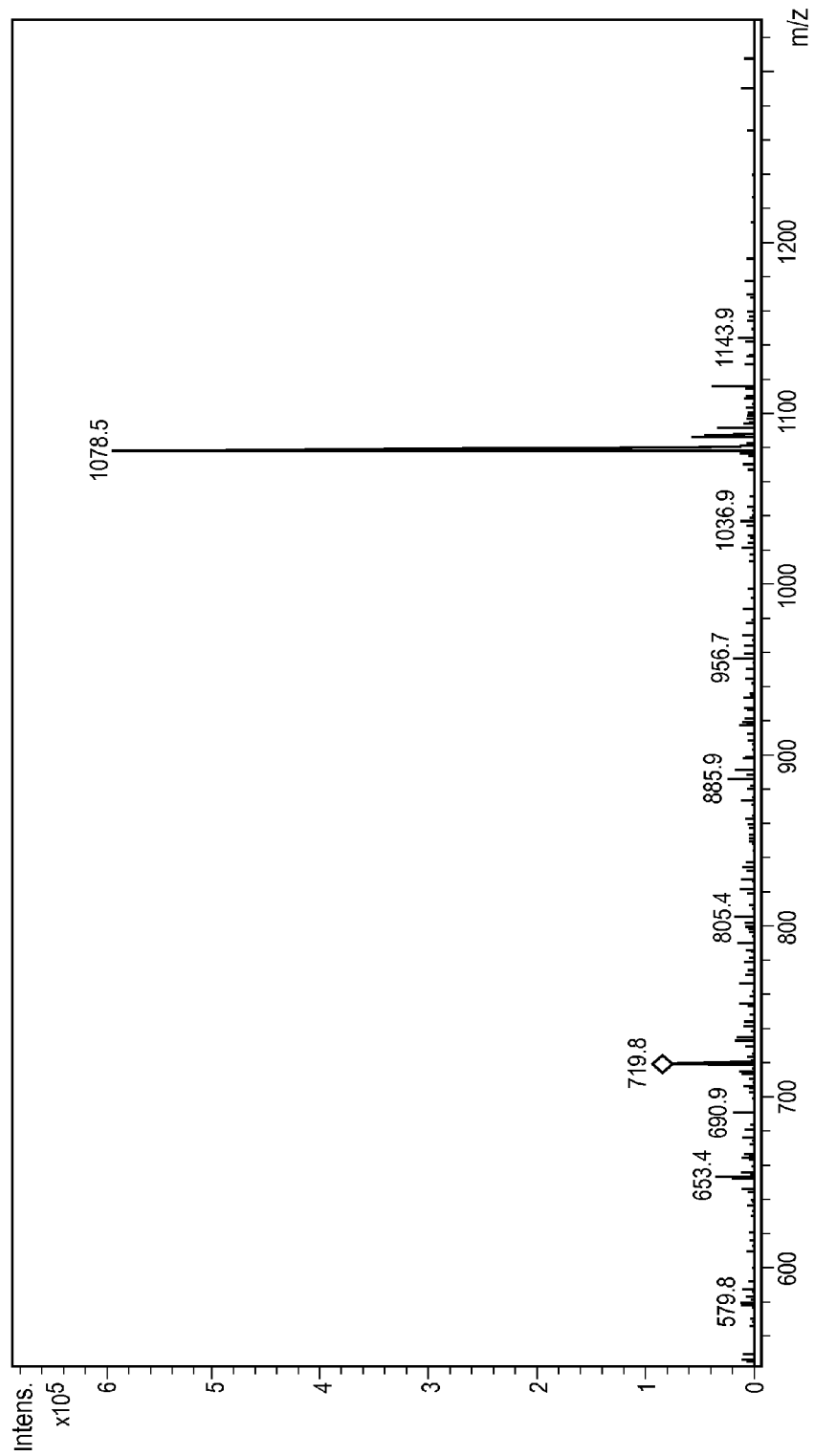
FIG. 7 and FIG. 8 represent mass spectra (full-scan low resolution spectrum) of antibiotic NAI-130 showing a doubly protonated ion at m/z 1078.5.
Figure 8:
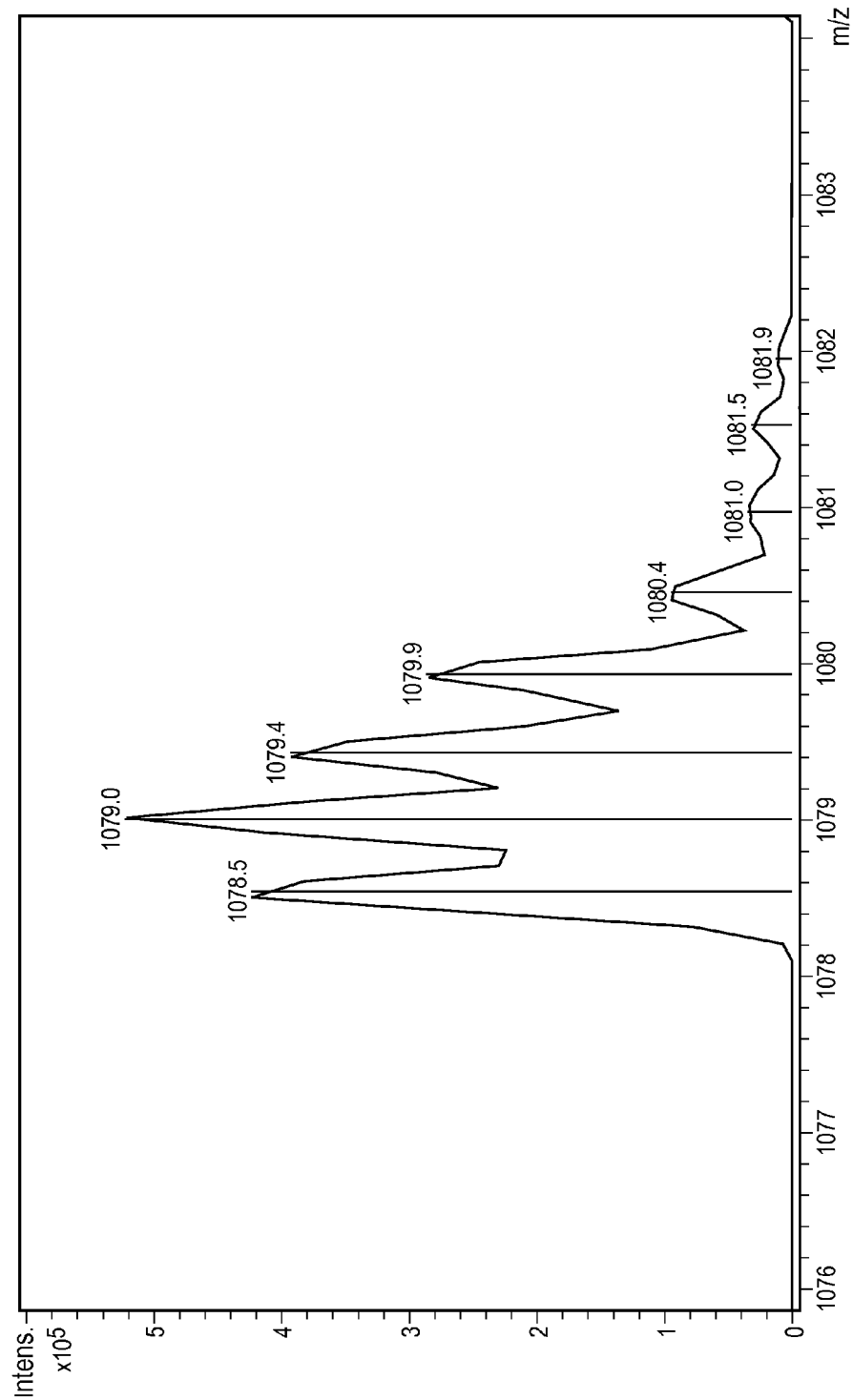

A) Mass spectrometry: in MS experiments on a Thermofinnigan LCQ deca instrument fitted with an electrospray source, using Thermofinnigan calibration mix, antibiotic NAI-130 gives a doubly protonated ion at 1079 m/z. MS/MS analysis of the double charged ion is performed with the observed main fragmentations: monocharged 1116, 1373, 1456, 1791 and double charged 1021 m/z. The electrospray conditions are: Spray Voltage: 4.7 kV; Capillary temperature: 220° C.; Capillary Voltage: 3 V; Infusion mode 10 μL/min. Spectra are recorded from a 0.2 mg/ml solution in methanol/water 80/20 (v/v) with trifluoroacetic acid 0.1% and are reported in FIG. 7 and FIG. 8 (full-scan low resolution spectrum).

Figure 9:
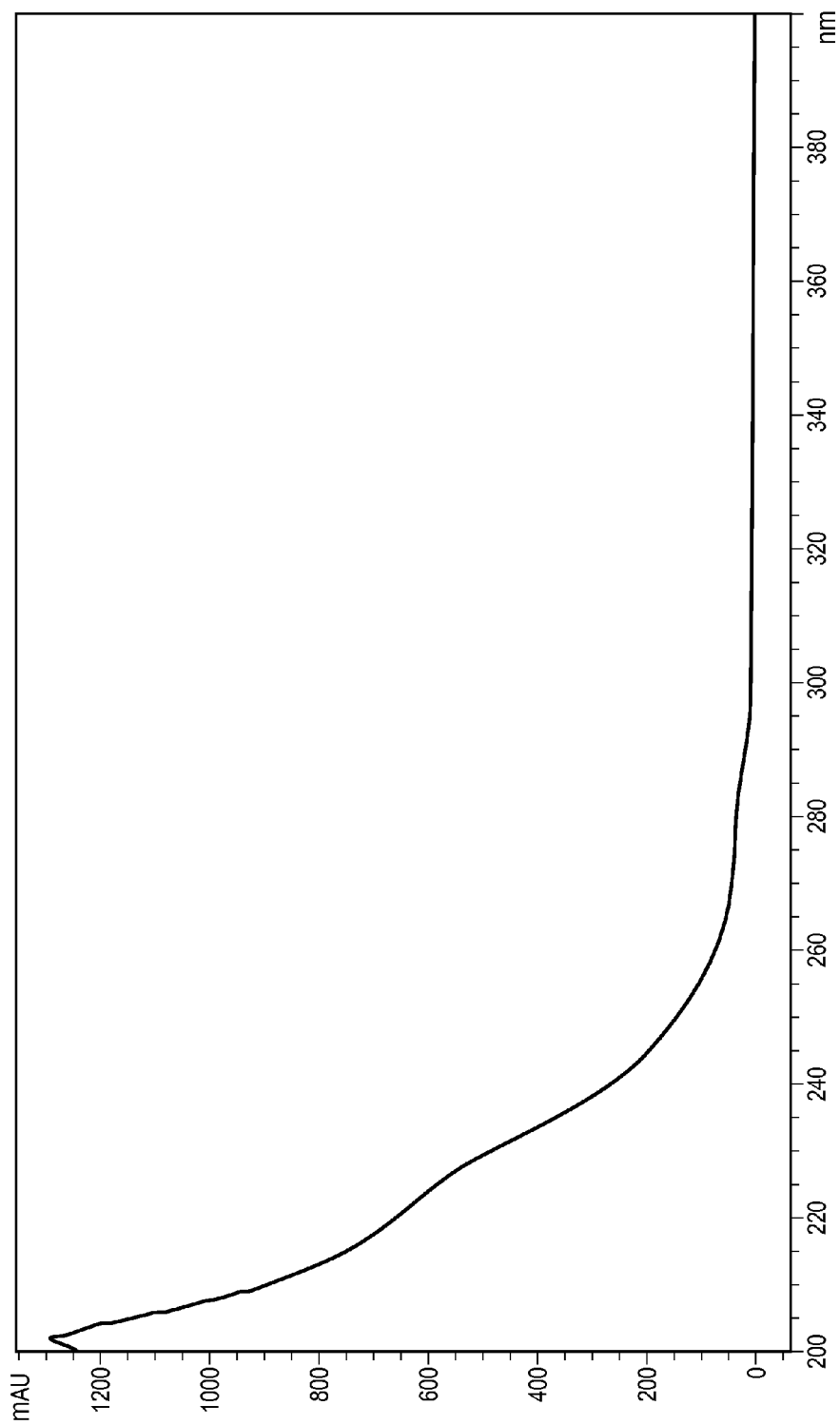
FIG. 9 represents the UV spectrum of antibiotic NAI-130 dissolved in Acetonitrile:TFA 0.1%=1:1

B) The U.V. spectrum of antibiotic NAI-130, performed in TFA 0.1%-acetonitrile (in ratio 50:50) with a Shimadzu Diode Array detector SPD-M10A VP (Shimadzu Corporation, Japan) during a HPLC analysis, exhibits two maxima at 225 and 280 nm. UV spectrum is reported in FIG. 9

C) $^1$H-NMR and 2D experiments are recorded in the mixtures $CD_3CN/D_2O$ (1/1) with and without the addition of 50 μL of $H_2O$ at 25° C. on a Bruker AMX 600 or 400 spectrometers. If necessary a water suppression sequence is applied.

Figure 10:
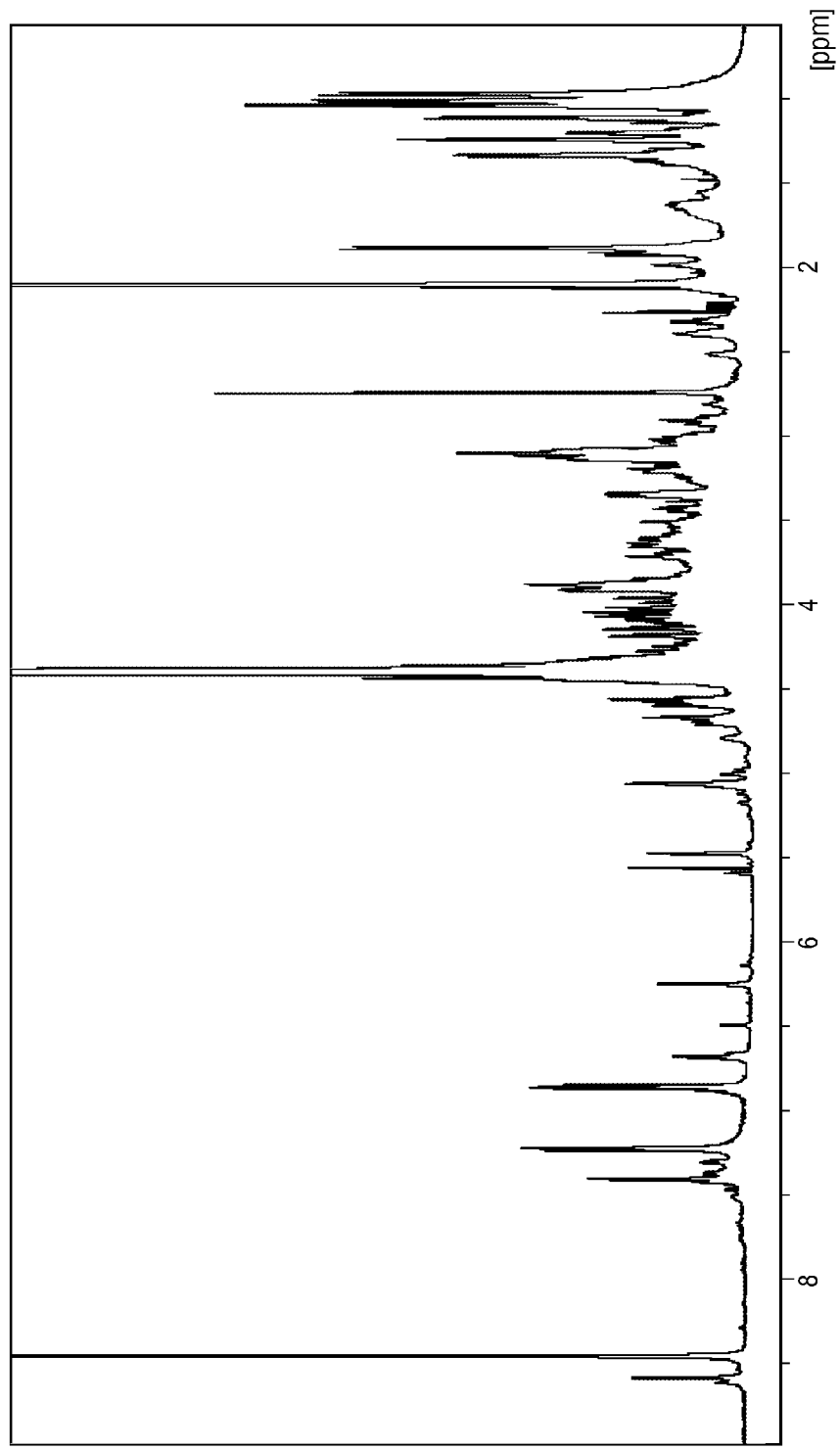
FIG. 10 represents the $^1$H-NMR spectrum of NAI-130 recorded in the mixture Acetonitrile-$d_3$:D20 at 25° C. on a Bruker AMX 600 spectrometer FIG. 11

$^1$H NMR spectrum of antibiotic NAI-130 exhibits the following groups of signals [δ=ppm; multiplicity; (attribution)]: 0.96 d ($CH_3$), 1.00 d ($CH_3$), 1.04 t ($CH_3$), 1.13 d ($CH_3$), 1.24 d ($CH_3$), 1.33 d ($CH_3$), 1.89 d ($CH_3$), 1.33-1.63 m ($CH_2$), 1.91-1.98 m ($CH_2$), 1.87-2.39 m ($CH_2$), 2.9-3.76 (peptidic beta CH and $CH_2$), 3.8-5.1 (peptidic alpha CH and $CH_2$), 5.47-6.26 s ($CH_2$), 6.68 q (CH), 6.89-9.21 s, d and m (aromatic CH's and peptidic NH's). The $^1$H-NMR spectrum of NAI-130 is reported in FIG. 10.

Figure 11:
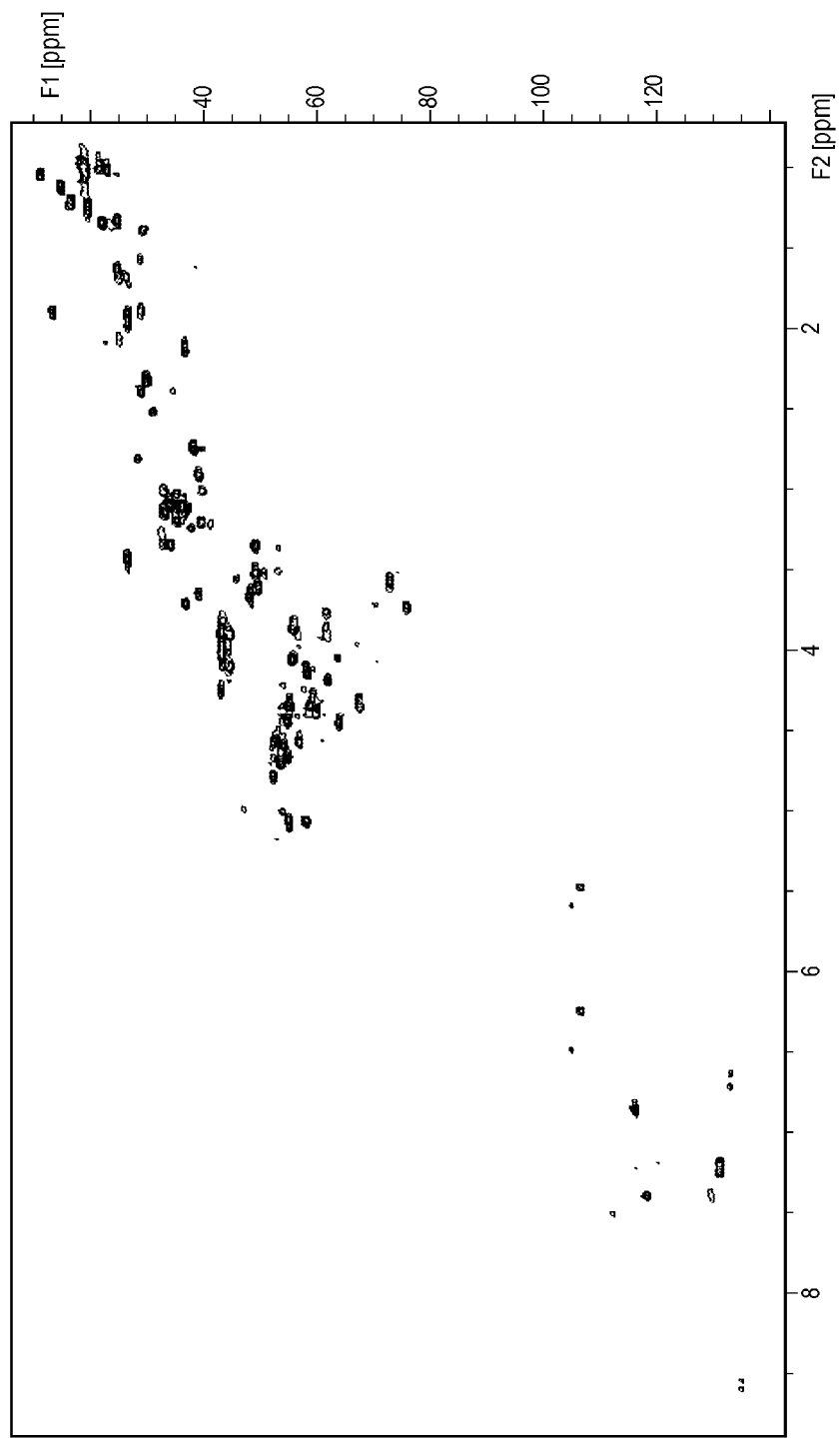
Figure 12:
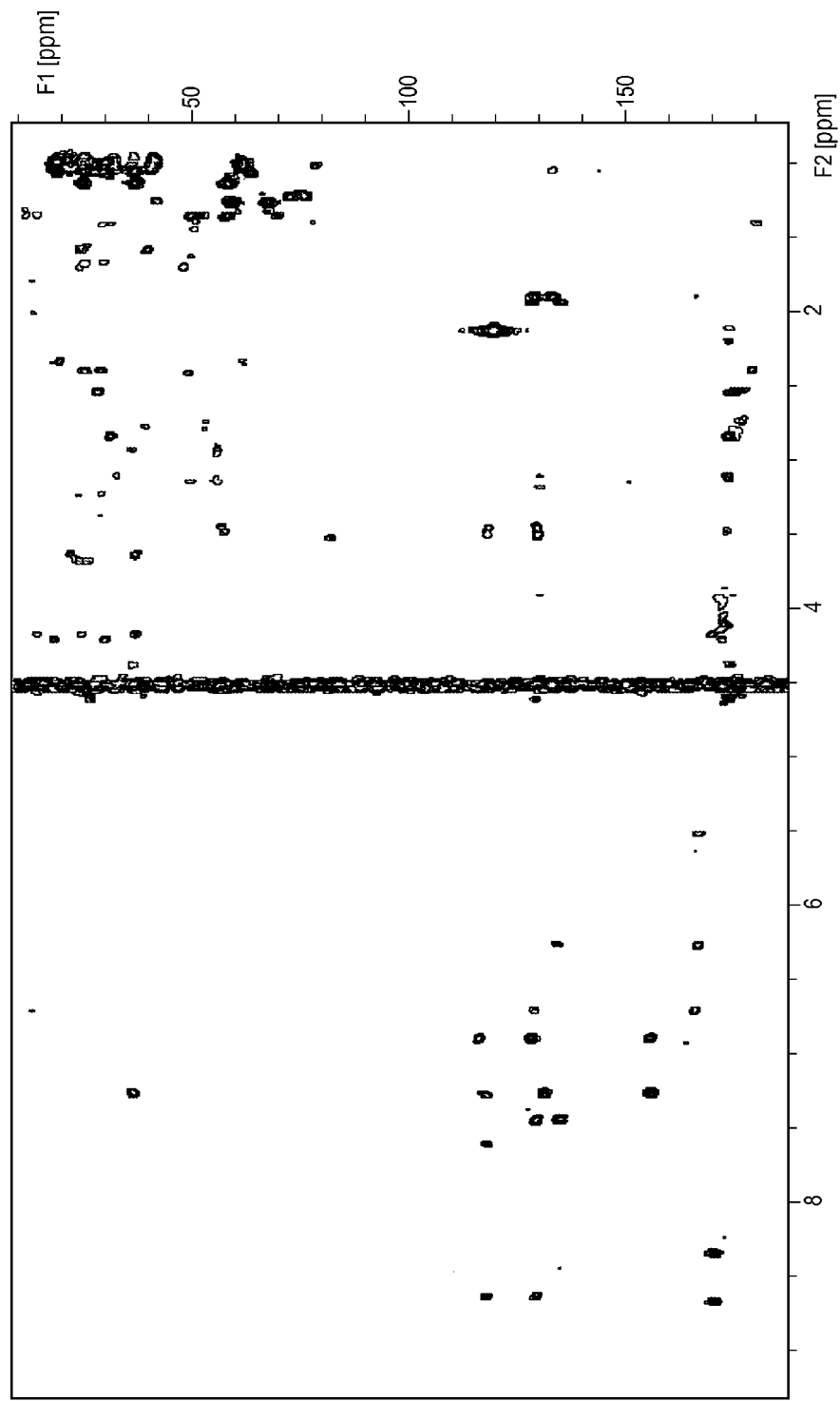
FIG. 12 represents the HSQC and HMBC NMR spectra of NAI-130 recorded in the mixture Acetonitrile-$d_3$:D20 at 25° C. on a Bruker AMX 600 spectrometer.

NAI-130 exhibits the following 13C groups of signals [δ=ppm; (attribution)]: 10.1-21.4 (aliphatic $CH_3$'s), 25.7-67.0 (aliphatic and peptidic signals), 106-157 (aromatic and double bonds CH's and quaternary carbons), 165-174 (peptidic carbonyls). HSQC and HMBC spectra of NAI-130 are reported in FIG. 11 and FIG. 12.

D) HPLC data: NAI-130 shows a retention time of 13.3 minutes when analysed with the HPLC method 1 as above described. NAI-130 shows a retention time of 3.5 minutes when analysed with HPLC method 2 as above described.

Physico-Chemical Characteristics of Antibiotic of Formula (I) NAI-114

Figure 13:
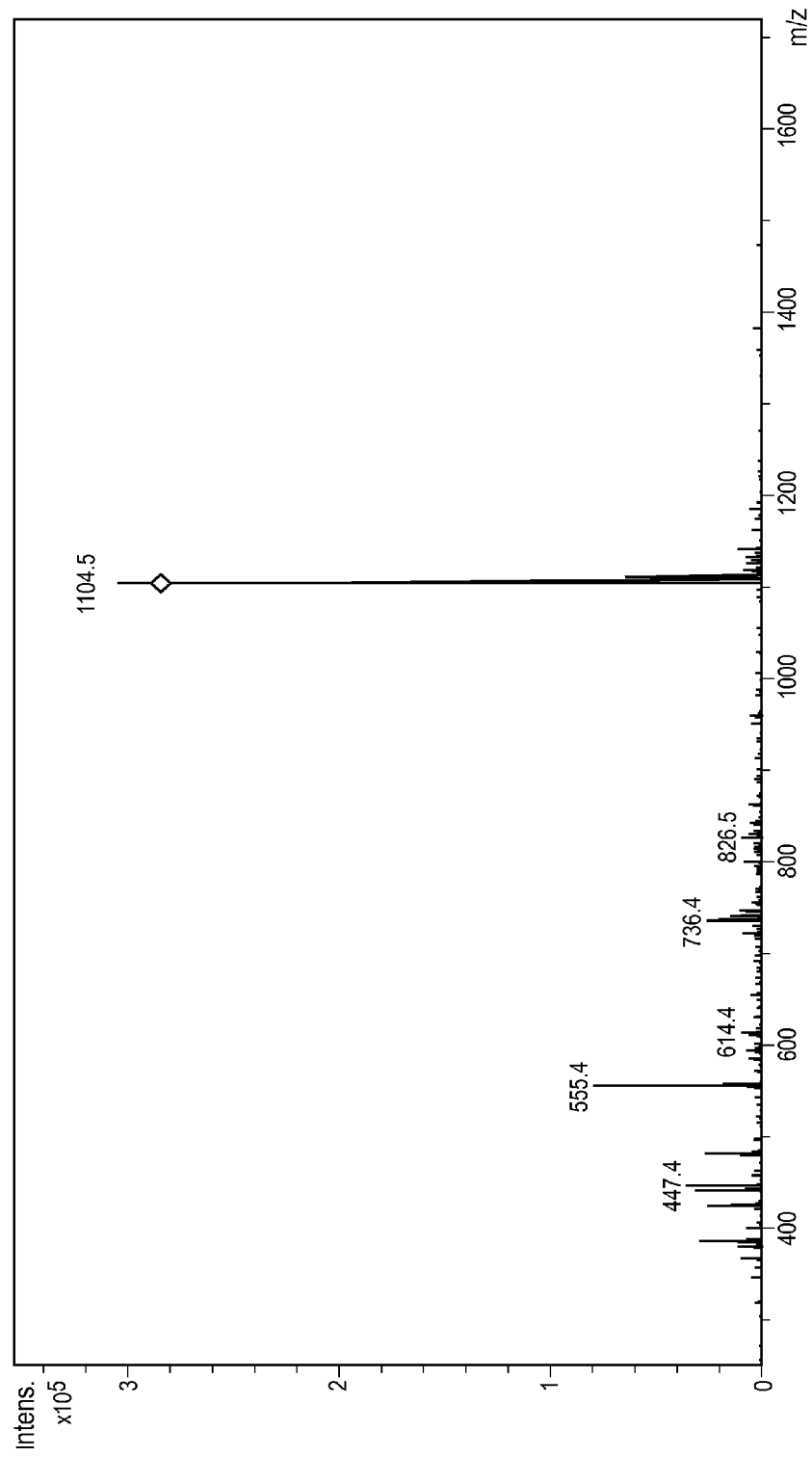
FIG. 13 and FIG. 14 represent mass spectra (full-scan low resolution spectrum) of antibiotic NAI-114 showing a doubly protonated ion at m/z 1104.
Figure 14:
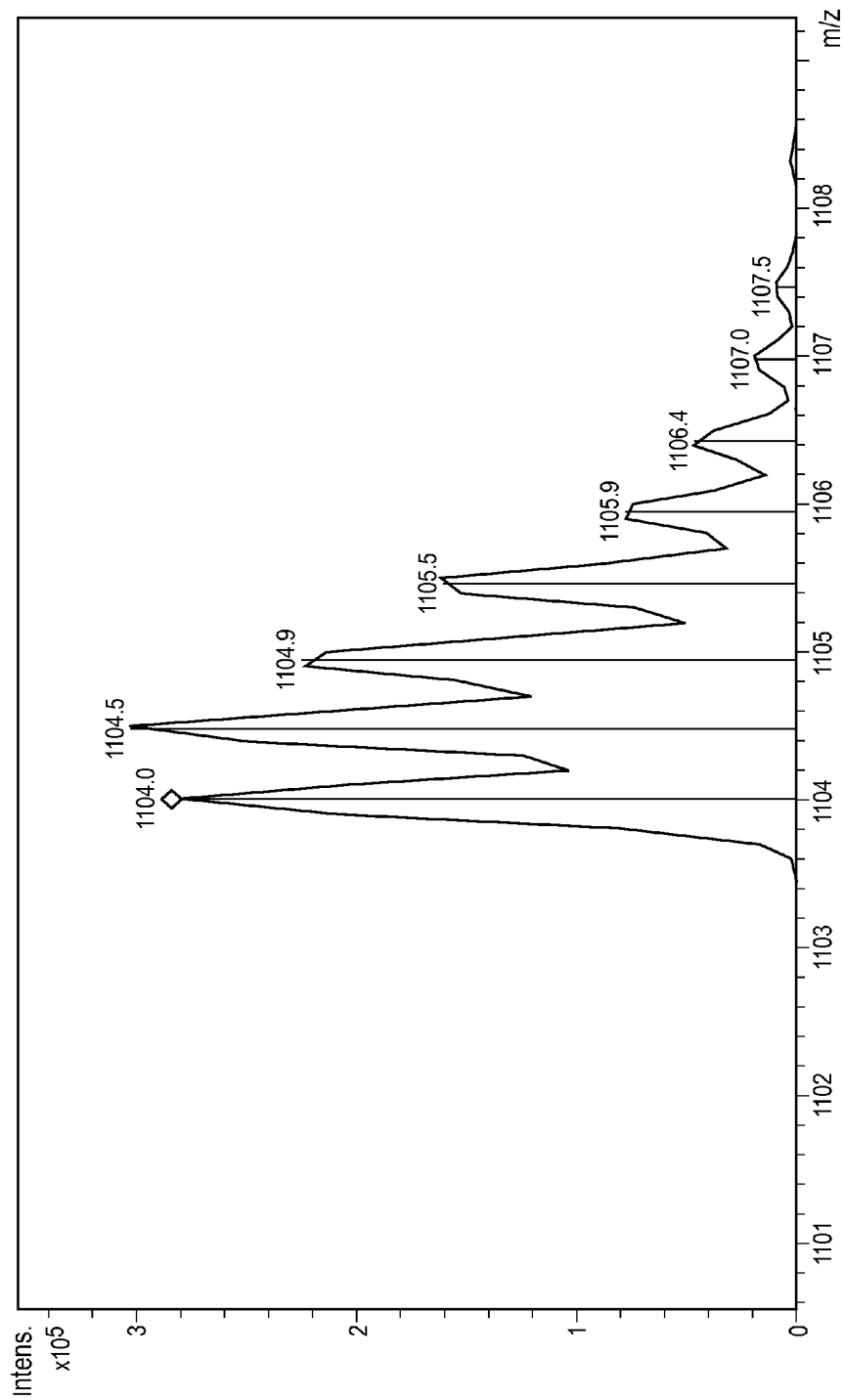

A) Mass spectrometry: in MS experiments on a Thermofinnigan LCQ deca instrument fitted with an electrospray source, using Thermofinnigan calibration mix, antibiotic NAI-114 gives a doubly protonated ion at 1104 m/z. MS/MS analysis of the double charged ion is performed with the observed main fragmentations: monocharged 1130, 1387, 1470, 1828 and double charged 1039 m/z. The electrospray conditions are: Spray Voltage: 4.7 kV; Capillary temperature: 220° C.; Capillary Voltage: 3 V; Infusion mode 10 μL/min. Spectra are recorded from a 0.2 mg/ml solution in methanol/water 80/20 (v/v) with trifluoroacetic acid 0.1% and are reported in FIG. 13 and FIG. 14 (full-scan low resolution spectrum).

Figure 15:
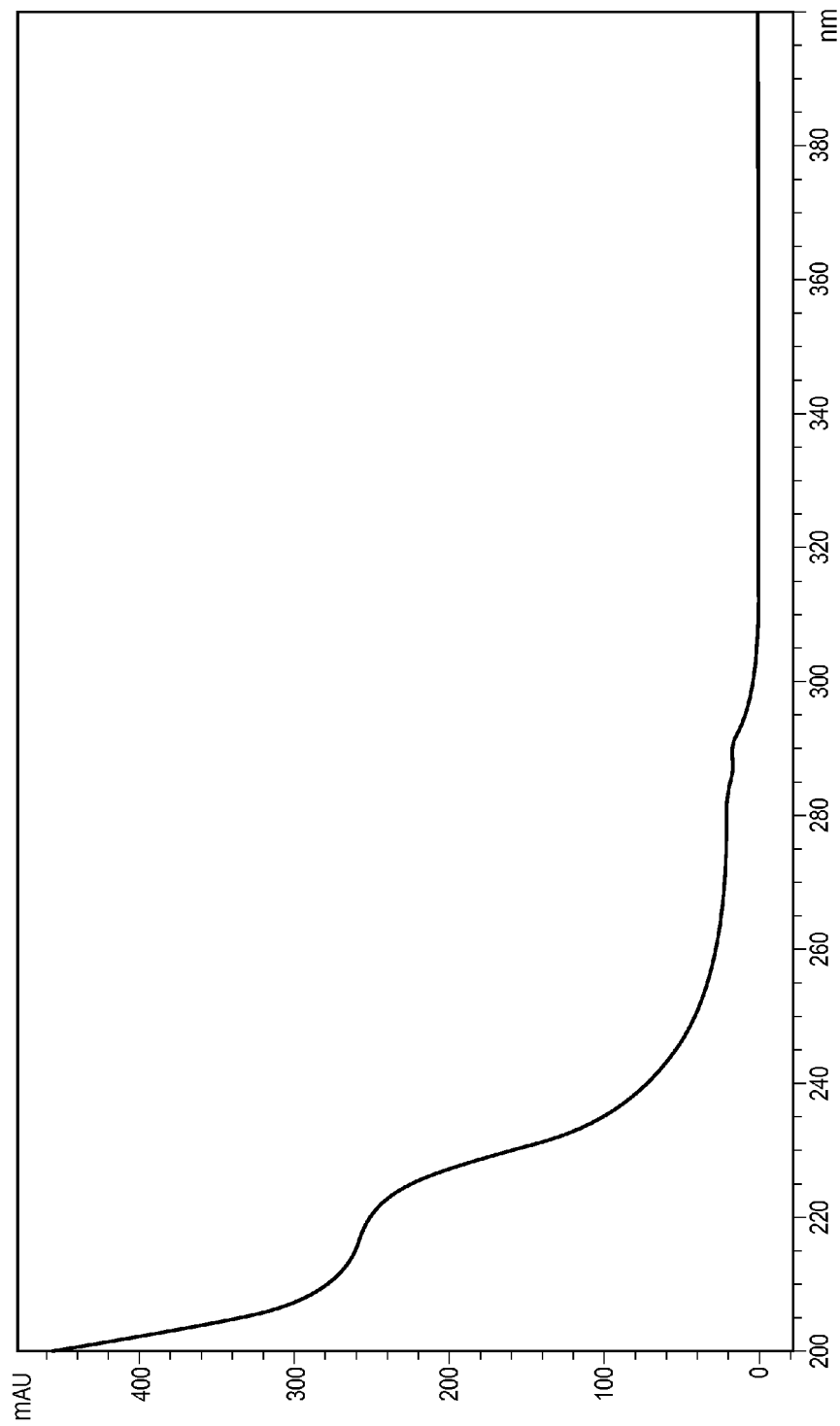
FIG. 15 represents the UV spectrum of antibiotic NAI-114 dissolved in Acetonitrile:TFA 0.1%=1:1

B) The U.V. spectrum of antibiotic NAI-114, performed in TFA 0.1%-acetonitrile (in ratio 50:50) with a Shimadzu Diode Array detector SPD-M10A VP (Shimadzu Corporation, Japan) during a HPLC analysis, exhibits two maxima at 225 and 280 nm. UV spectrum is reported in FIG. 15

C) $^1$H-NMR and 2D experiments are recorded in the mixtures $CD_3CN/D_2O$ (1/1) with and without the addition of 50 μL of $H_2O$ at 25° C. on a Bruker AMX 600 or 400 spectrometers. If necessary a water suppression sequence is applied.

Figure 16:
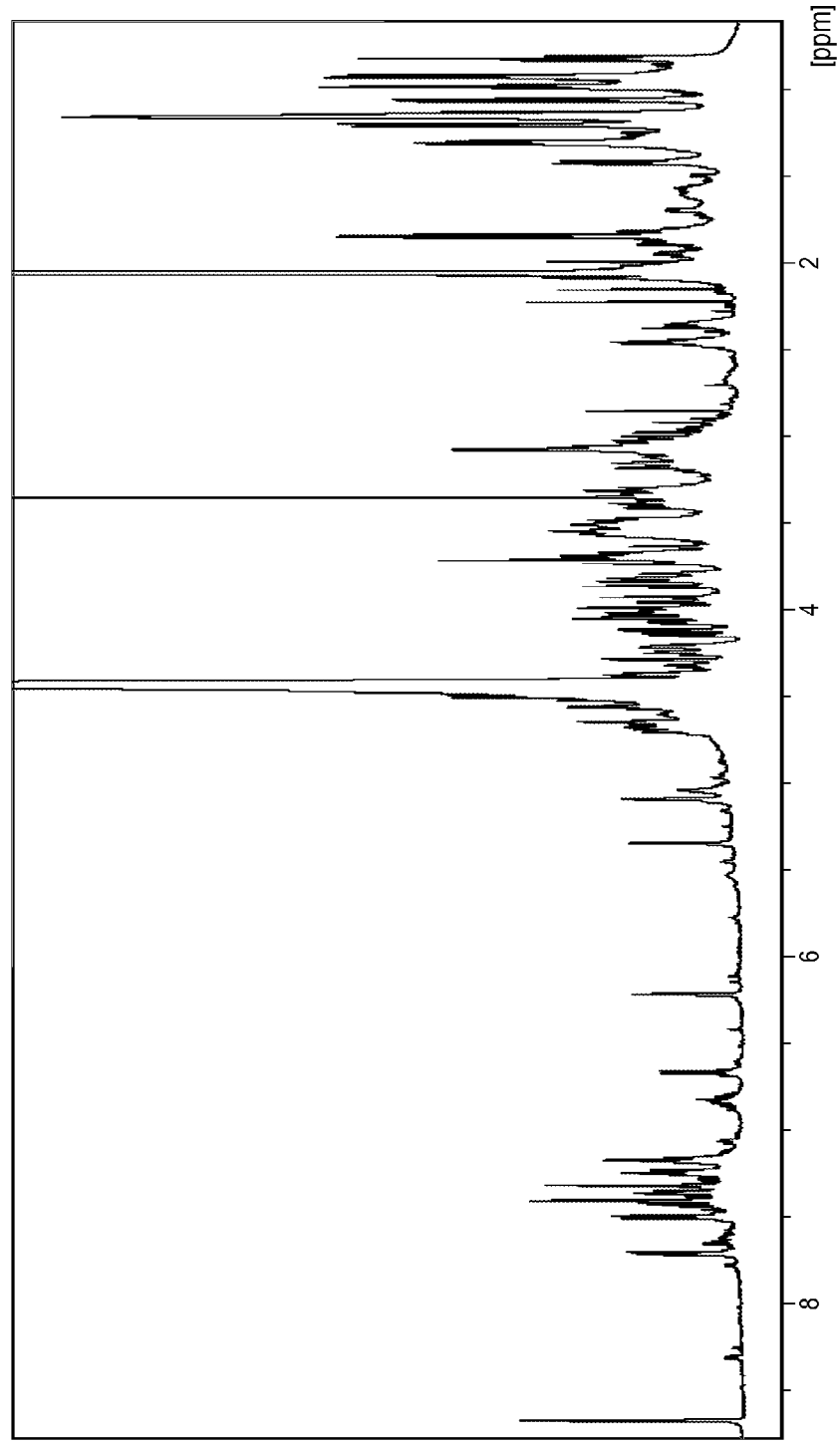
FIG. 16 represents the $^1$H-NMR spectrum of NAI-114 recorded in the mixture Acetonitrile-$d_3$:D20 at 25° C. on a Bruker AMX 600 spectrometer FIG. 17

$^1$H NMR spectrum of antibiotic NAI-114 exhibits the following groups of signals [δ=ppm; multiplicity; (attribution)]: 0.83 t ($CH_3$), 0.93 d ($CH_3$), 0.99 t (CH3), 1.07 d (CH3), 1.21 d ($CH_3$), 1.31 d ($CH_3$), 1.85 d ($CH_3$), 1.8-5.3 (peptidic CH and $CH_2$), 5.34-6.22 s ($CH_2$), 6.66 q (CH), 7.31-10.09 s, d and m (aromatic CH's and peptidic NH's). The $^1$H-NMR spectrum of NAI-114 is reported in FIG. 16.

Figure 17:
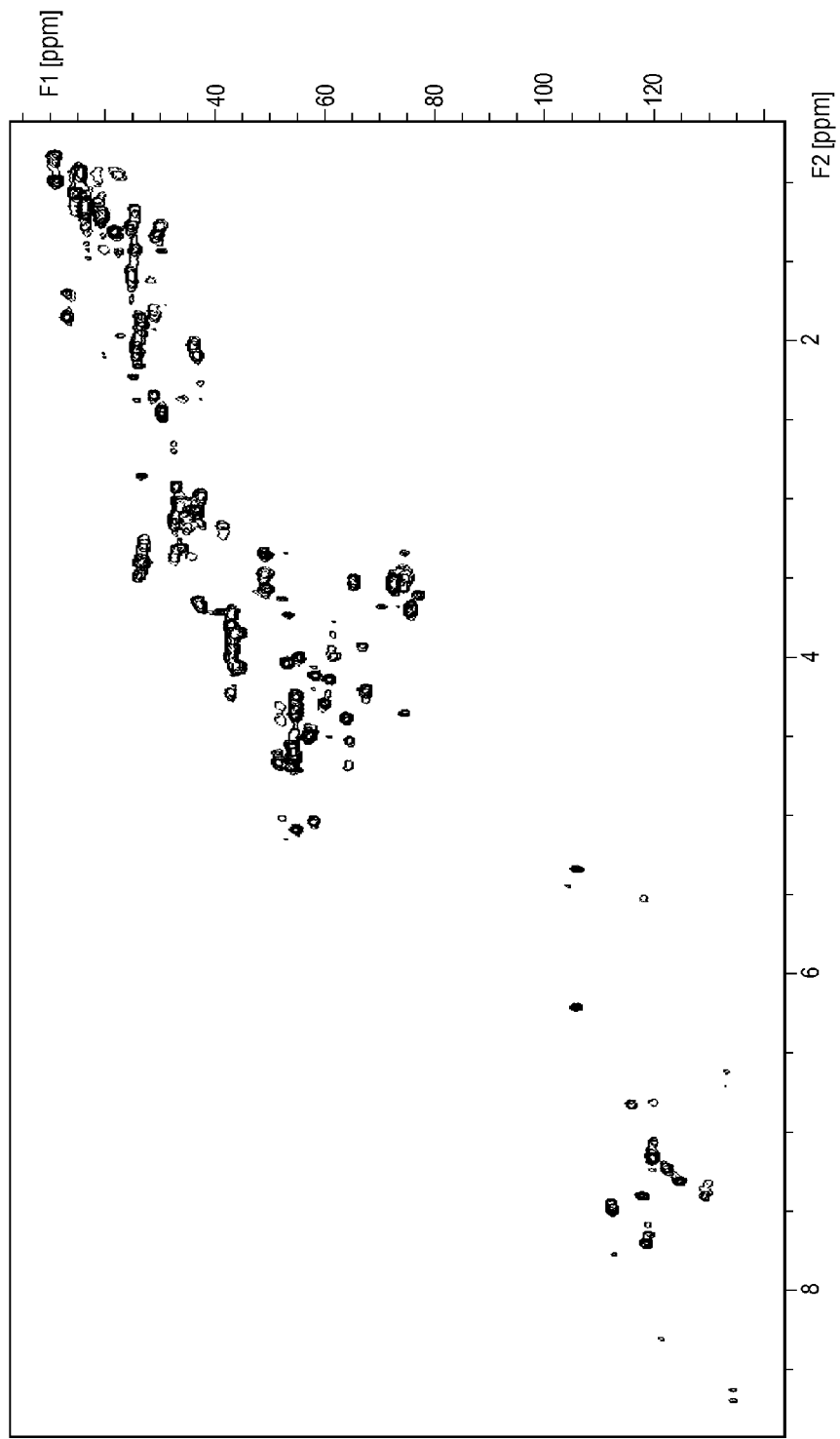
Figure 18:
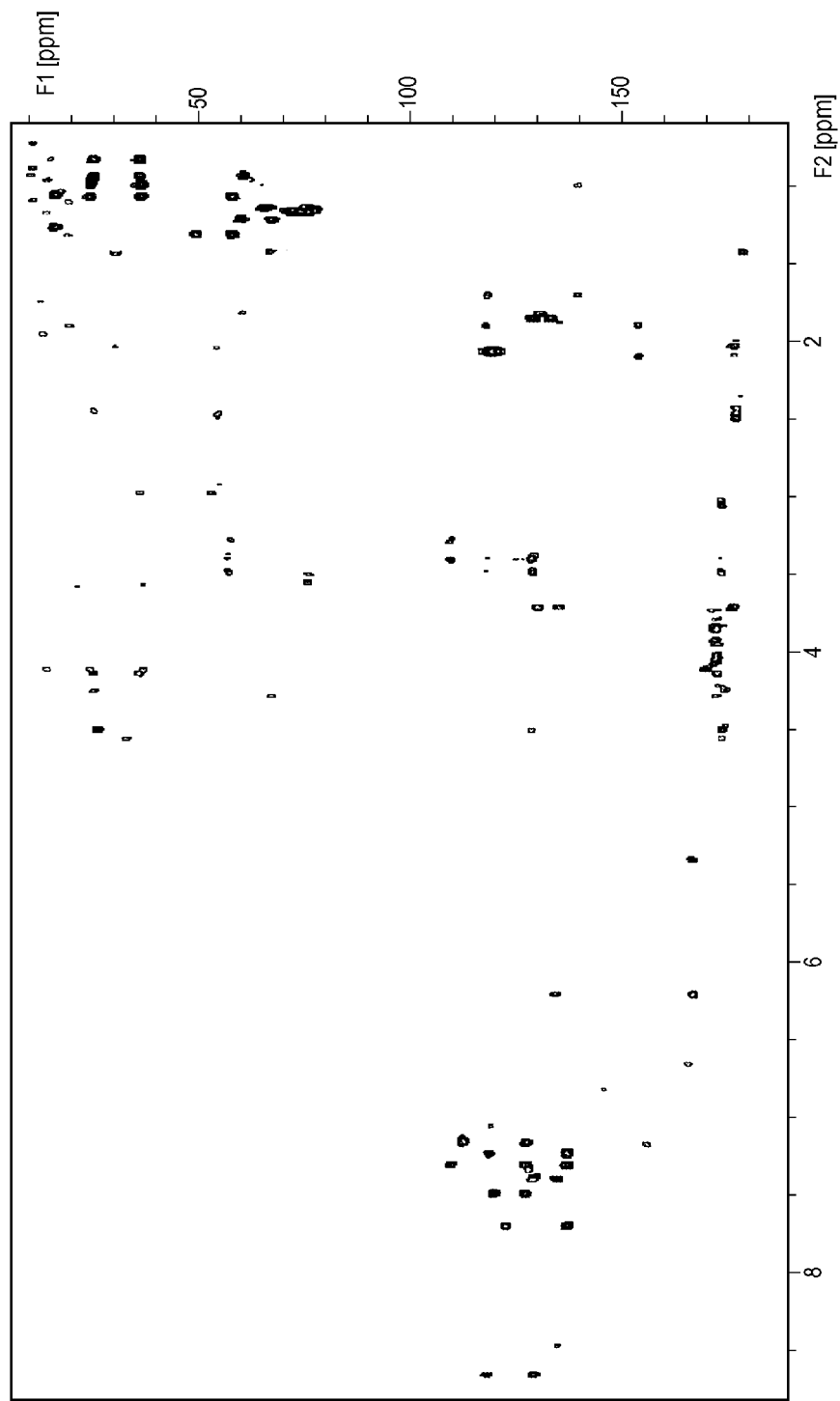
FIG. 18 represents the HSQC and HMBC NMR spectra of NAI-114 recorded in the mixture Acetonitrile-$d_3$:D20 at 25° C. on a Bruker AMX 600 spectrometer.

NAI-114 exhibits the following 13C groups of signals [δ=ppm; (attribution)]: 10.6-21.6 (aliphatic $CH_3$'s), 24.7-67.1 (aliphatic and peptidic signals), 105-134 (aromatic and double bonds CH's and quaternary carbons), 165-174 (peptidic carbonyls). HSQC and HMBC spectra of NAI-114 are reported in FIG. 17 and FIG. 18

D) HPLC data: NAI-114 shows a retention time of 16.7 minutes when analysed with the HPLC method 1 as above described. NM-114 shows a retention time of 4.1 minutes when analysed with HPLC method 2 as above described.

Physico-Chemical Characteristics of Antibiotic of Formula (I) NAI-438

Figure 19:
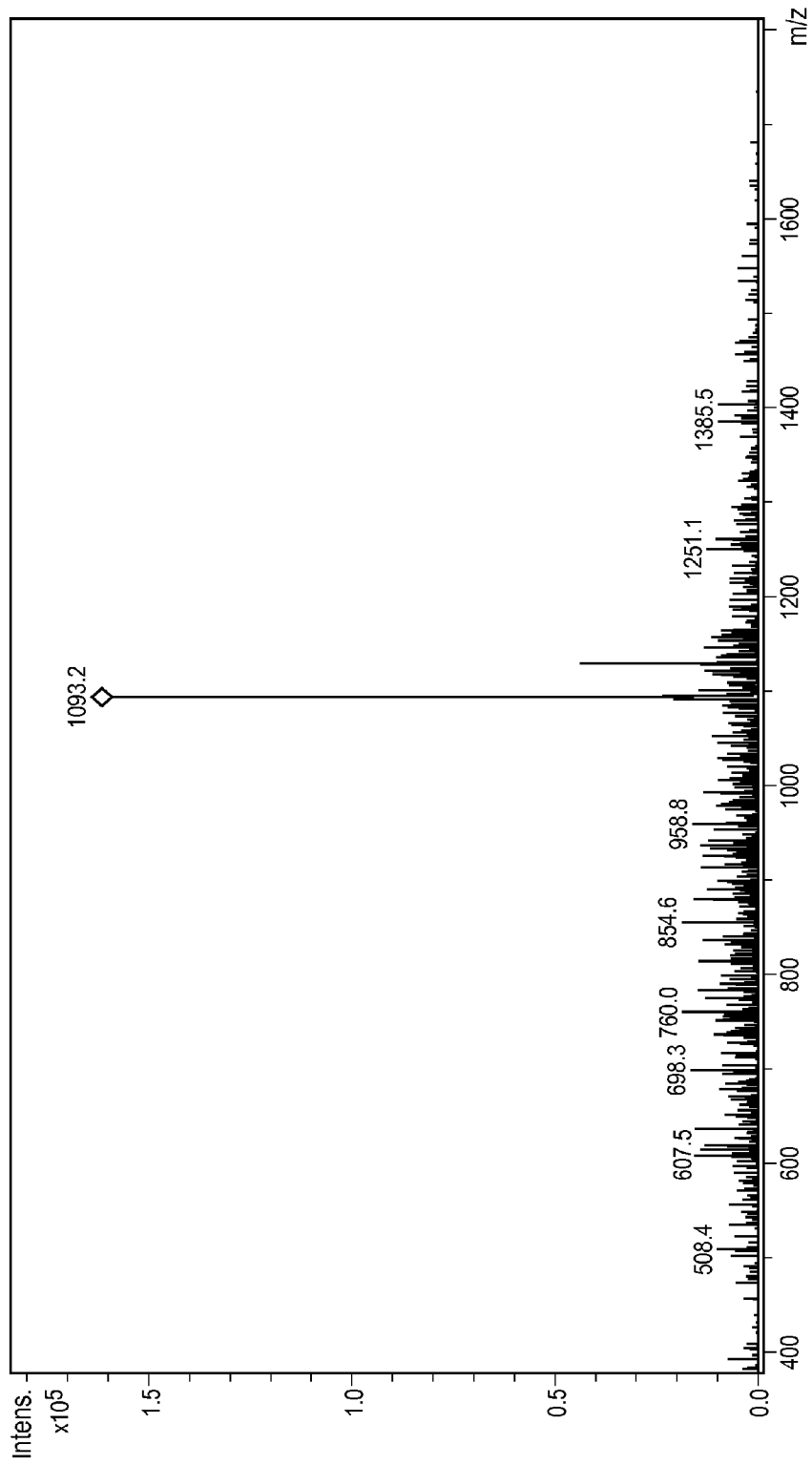
FIG. 19 and FIG. 20 represent mass spectra (full-scan low resolution spectrum) of antibiotic NAI-438 showing a doubly protonated ion at m/z 1093.
Figure 20:
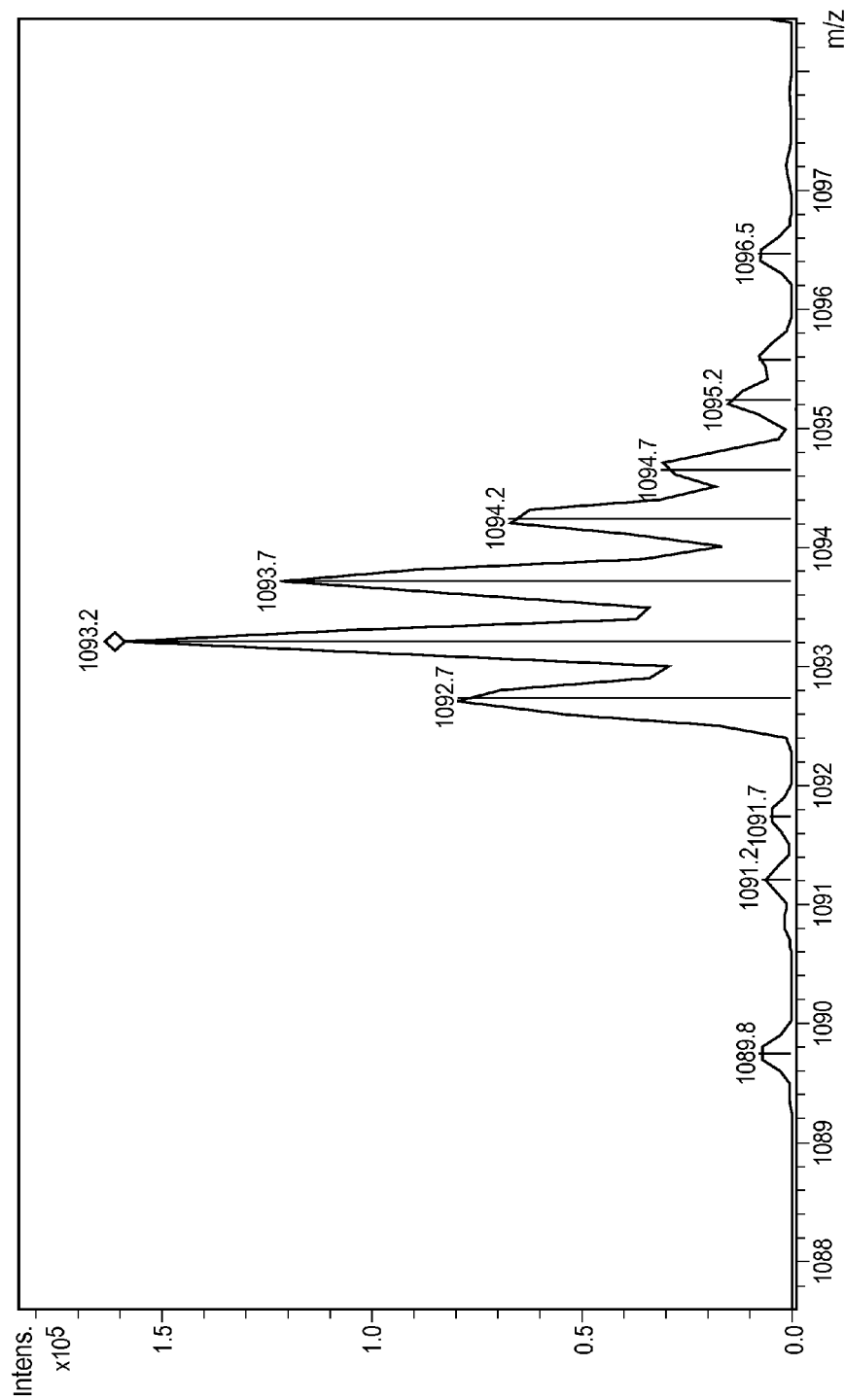

A) Mass spectrometry: in MS experiments on a Thermofinnigan LCQ deca instrument fitted with an electrospray source, using Thermofinnigan calibration mix, antibiotic NAI-438 gives a doubly protonated ion at 1093 m/z. MS/MS analysis of the double charged ion is performed with the observed main fragmentations: monocharged 1130, 1387, 1470, 1806 and double charged 1036 m/z. The electrospray conditions are: Spray Voltage: 4.7 kV; Capillary temperature: 220° C.; Capillary Voltage: 3 V; Infusion mode 10 μL/min. Spectra are recorded from a 0.2 mg/ml solution in methanol/water 80/20 (v/v) with trifluoroacetic acid 0.1% and are reported in FIG. 19 and FIG. 20 (full-scan low resolution spectrum).

Figure 21:
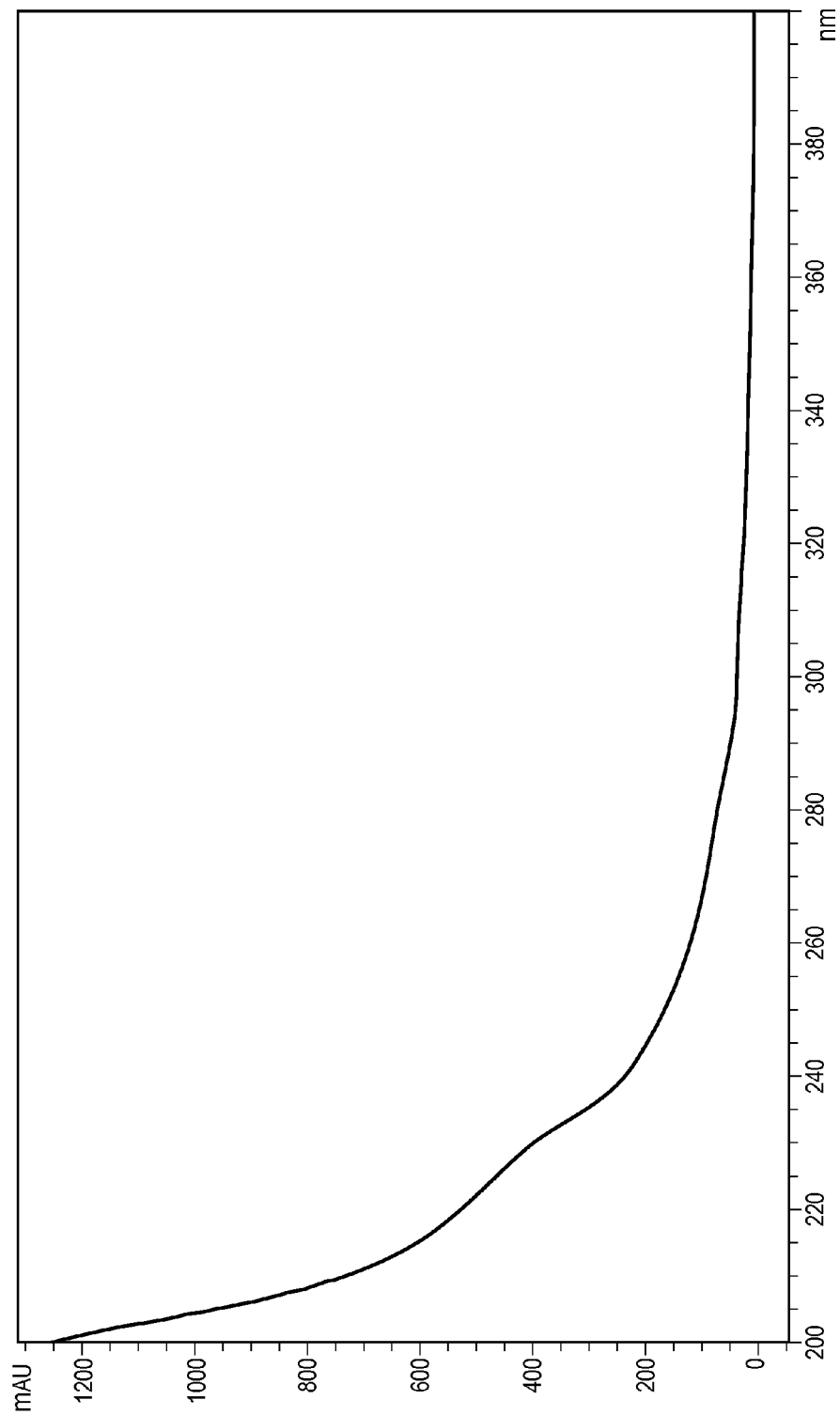
FIG. 21 represents the UV spectrum of antibiotic NAI-438 dissolved in Acetonitrile:TFA 0.1%=1:1
Figure 22:
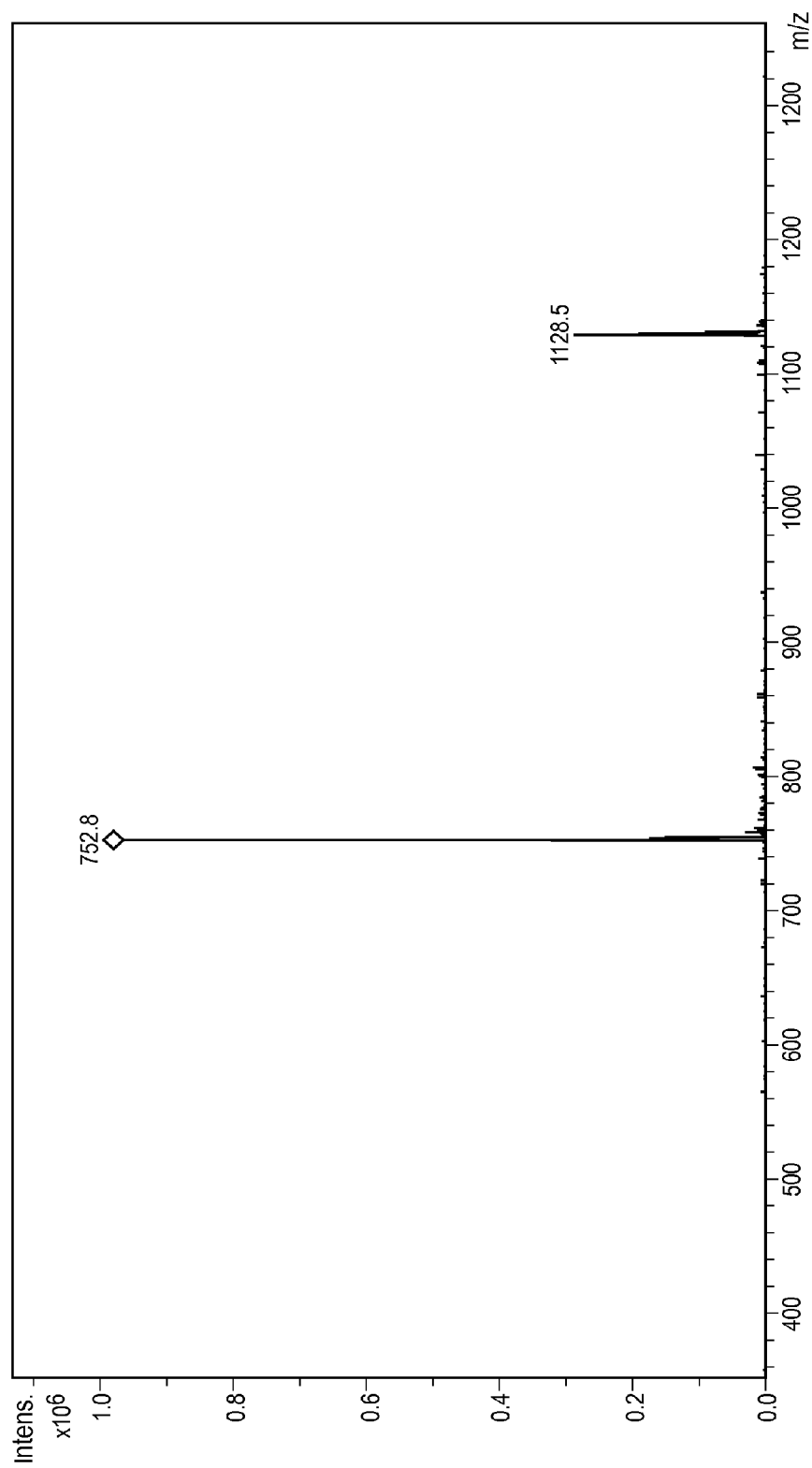
FIG. 22 and FIG. 23 represent mass spectra (full-scan low resolution spectrum) of NAI-857 diamide with ethylenediamine showing a doubly protonated ion at m/z 1128.
Figure 23:
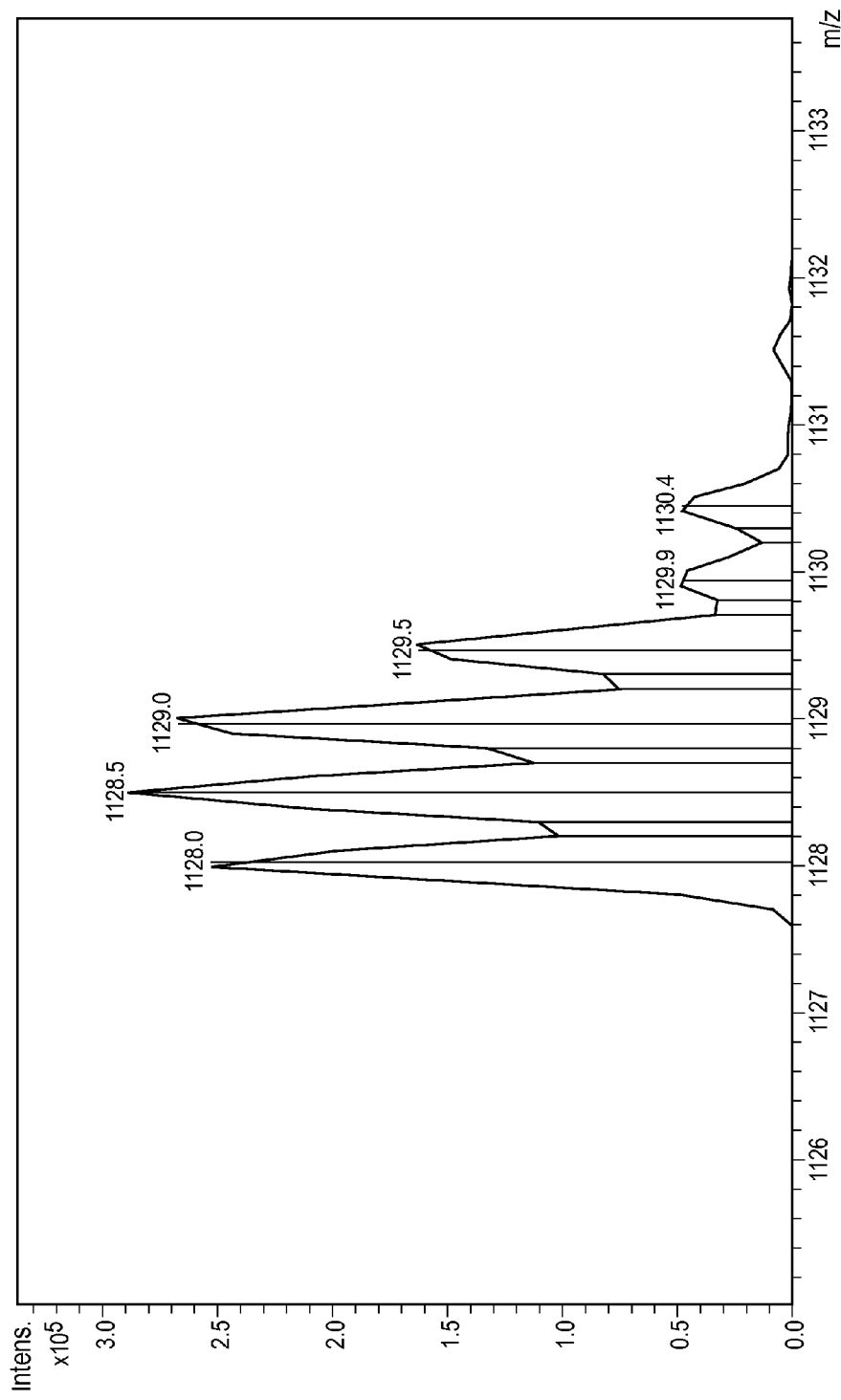
Figure 24:
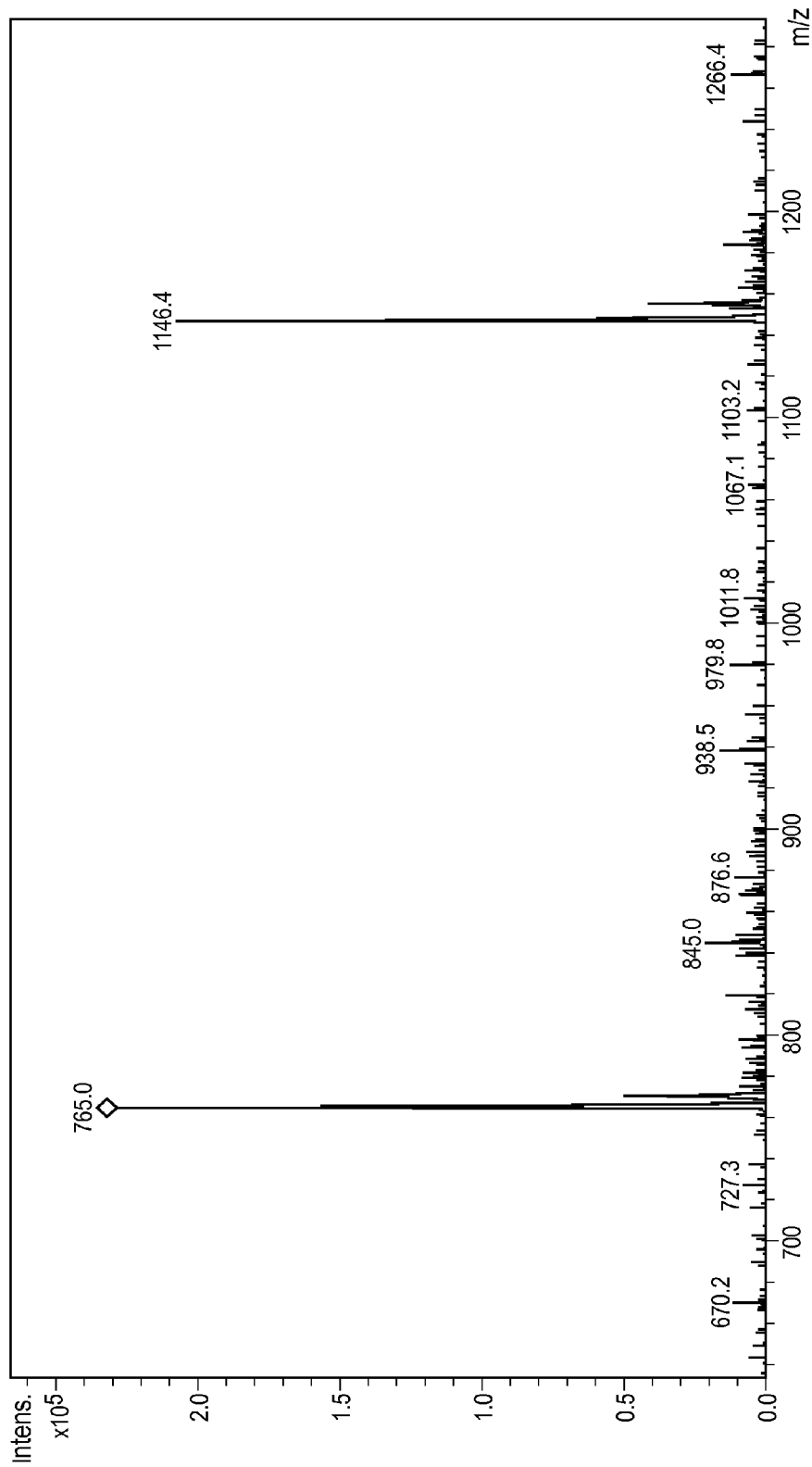
FIG. 24 and FIG. 25 represent mass spectra (full-scan low resolution spectrum) of NAI-114 diamide with ethylenediamine showing a doubly protonated ion at m/z 1146.
Figure 25:
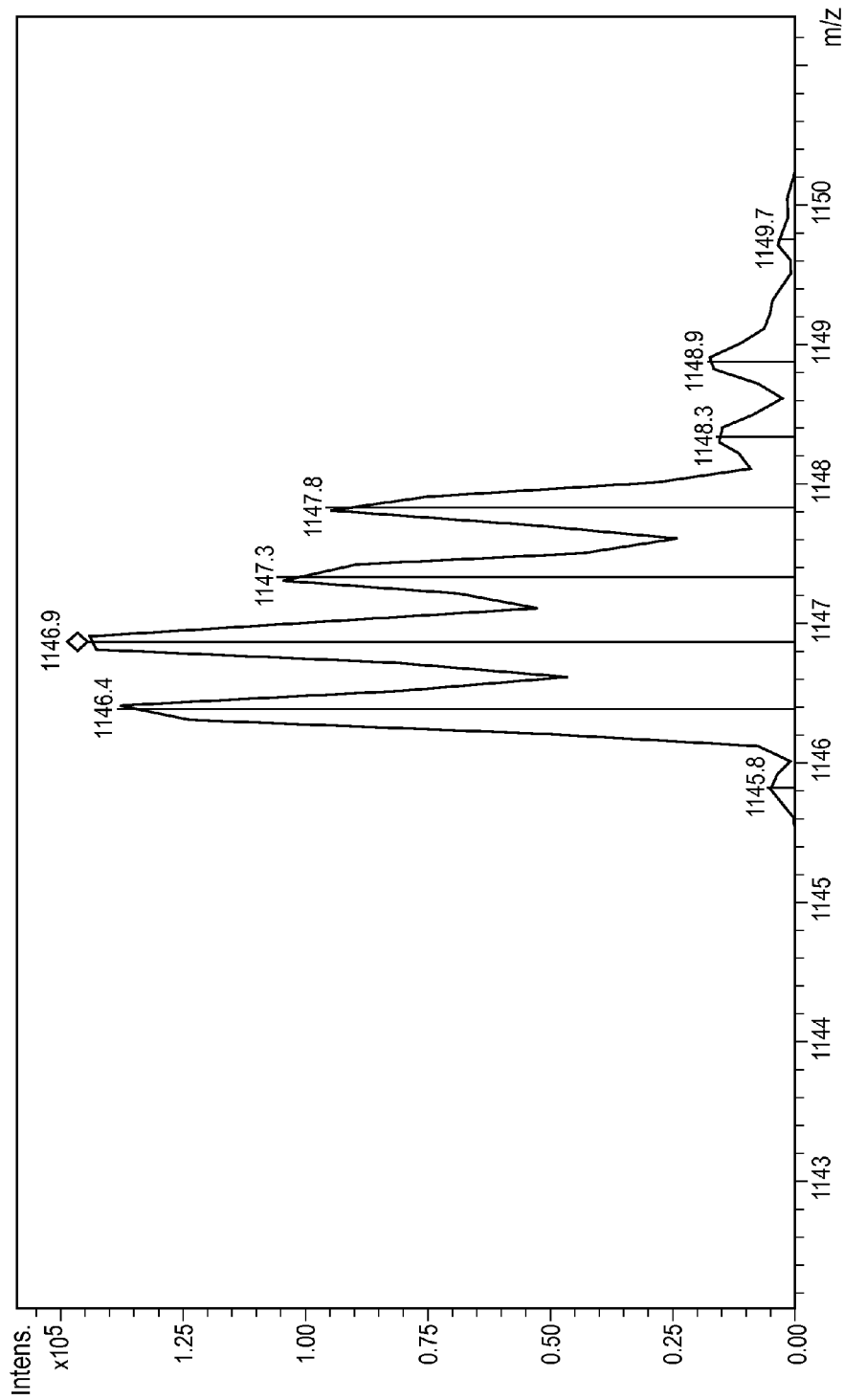

B) The U.V. spectrum of antibiotic NAI-438, performed in TFA 0.1%-acetonitrile (in ratio 50:50) with a Shimadzu Diode Array detector SPD-M10A VP (Shimadzu Corporation, Japan) during a HPLC analysis, exhibits two maxima at 225 and 280 nm. UV spectrum is reported in FIG. 21

D) HPLC data: NAI-438 shows a retention time of 14.4 minutes when analysed with the HPLC method 1 as above described. NAI-438 shows a retention time of 3.5 minutes when analysed with HPLC method 2 as above described.

Determination of "Acid Resistant" Aminoacids in Antibiotic NAI-857

Acid labile amino acids are not detectable with this approach. The hydrolysate of NAI-857 was studied by HPLC-MS analysis, after suitable derivatization, in comparison with a mixture of standard amino acids similarly derivatized. Antibiotic NAI-857 was submitted to complete acidic hydrolysis (HCl 6N, 160° C., 5 minutes, microwaves). The hydrolyzed sample was treated with 4-[4-isothiocyanate-phenyl]-azo-N,N-dimethyl aniline and triethylamine in water:acetonitrile 1:1. The reaction mixture was stirred 2 hours at 60° C. and extracted with petroleum ether:methylene chloride 8:2. The organic phase was evaporated to dryness, redissolved in water:acetonitrile 1:1 (1 mL) and analyzed by HPLC-MS.

The qualitative HPLC analysis was carried out on a liquid chromatography system with simultaneous DAD and MS detection. The HPLC method had the following conditions: Column: Ascentis express Supelco RP18, 2.7μ (50×4.6 mm) Column temperature: 40° C. Flow: 1 mL/min. Phase A: Trifluoroacetic acid 0.05% in water (v/v) Phase B: Trifluoroacetic acid 0.05% in acetonitrile (v/v)
Elution Program

| | Time (min.) | | | | |
|---|---|---|---|---|---|
| | 0 | 6 | 7 | 7.2 | 10 |
| % B | 5 | 95 | 100 | 5 | 5 |

MS conditions were the following: Spectrometer: Bruker Esquire3000 plus equipped with standard electrospray source: capillary temperature: 365° C.; capillary voltage: −4 kV; end plate offset: −500V; sheat gas ($N_2$): 50 psi.

In the LC/MS chromatograms obtained on the hydrolysate of antibiotic NAI-857, the following amino acids are identified along with other unidentified peaks: lanthionine, methyllanthionine, glycine, proline, phenylalanine, tyrosine and leucine or isoleucine.

Identification of N-Terminal Aminoacid in NAI-857:

5 mg of NAI-857 were dissolved in 200 μL of DMF, triethylamine (5 μL) and phenylisothiocyanate (5 μL) were added and the reaction was stirred at 60° C. for 1 h. After that time HPLC-MS showed the reaction complete. The solution was extracted with hexane:dichloromethane 8:2 (3λ300 μL), evaporated to dryness, dissolved in trifluoroacetic acid and reacted at 60° C. for 1 h. HPLC-MS analysis shows that reaction is complete, with the double charged peak of m/z 1029 amu corresponding to the loss of the N-terminal Leu (or Ile) amino acid residue. (NMR analysis highlights the presence of two isoleucine residues while leucine was not detected)

N-Terminal Aminoacid Identification of NAI-130:

5 mg of NAI-130 were dissolved in 200 μL of DMF. Triethylamine (5 μL) and phenylisothiocyanate (5 μL) were added and the reaction was stirred at 60° C. for 1 h. After that time HPLC-MS showed the reaction complete. The solution was extracted with hexane: dichloromethane 8:2 (3λ300 μL), evaporated to dryness, dissolved in trifluoroacetic acid (500 μL) and reacted at 60° C. for 1 h. The reaction solution was directly analysed by HPLC-MS and the double charged peak of m/z 1029 amu corresponding to the truncated peptide was detected corresponding to a loss of the N-terminal Val aminoacid.

The following examples are provided for illustrative purposes only and should in no way be considered as limiting the protection scope of the disclosure encompassed herein.

EXAMPLES

Example 1: Fermentation Method of STREPTOMYCES sp. DSM 24069

Streptomyces sp. DSM 24069 is maintained on S1 plates for 2-3 weeks at 28° C. S1 is composed of (g/L): oatmeal 60, agar 18, $FeSO_4 \times 7$ $H_2O$ 0.001, $MnCl_2 \times 4$ $H_2O$ 0.001, $ZnSO_4 \times 7$ $H_2O$ 0.001 and prepared by boiling oatmeal in 1 L distilled water for 20 min, filtering it through cheesecloth, adding the remaining components, adjusting volume to 1 L with distilled water and pH to 7.2 before sterilization at 121° C. for 20 min. The microbial content of one plate is scraped and inoculated into 500 mL Erlenmeyer flasks containing 100 ml of seed medium which is composed of (g/l): dextrose monohydrate 20, yeast extract 2, soybean meal 8, NaCl 1 and calcium carbonate 4. Medium is prepared in distilled water and pH adjusted to 7.3 prior to sterilization at 121° C. for 20 min. The inoculated flasks are grown at 28° C., on a rotatory shaker operating at 200 rpm. After 2-3 days, 5% of this culture is inoculated into a series of flasks containing the same medium. After 72 hours of incubation, 500 mL are transferred into 19.5 L bioreactor containing 10 L of the production medium composed of (g/L) corn steep liquor 30, maize dextrin 20, yeast extract 5, glucose monohydrate 10, calcium carbonate 2, NaCl 1. The medium is prepared in deionized water and the pH adjusted to 7 before sterilization at 121° C. for 25 min, while glucose is sterilized separately and added after cooling. The fermentation is carried out at 30° C., with 400 rpm stirring and 0.5 vvm aeration. During the fermentation pH is maintained <7.2 by addition of sulphuric acid when required. The fermenter is harvested after 98 hours of fermentation. The production of the antibiotic NAI-857 is monitored by HPLC as previously described, after extracting the whole culture broth with twice the volume of methanol and stirring for one hour.

Example 2: Fermentation Method of Streptomyces sp. DSM 24058

Streptomyces sp. DSM 24058 is maintained on S1 plates (composed and prepared as described in Example 1) for 2-3 weeks at 28° C. The microbial content of one plate is scraped and inoculated into 500 mL Erlenmeyer flasks containing 100 ml of seed medium which is composed and prepared as described in Example 1. The inoculated flasks are grown at 28° C., on a rotatory shaker operating at 200 rpm. After 3-4 days, 5% of this culture is inoculated into a series of flasks containing the same medium. After 48 hours of incubation, 300 mL are transferred into 19.5 L bioreactor containing 6 L of the production medium composed and prepared as described in Example 1. The fermentation is carried out at 30° C., with 500 rpm stirring and 0.6 vvm aeration. During the fermentation pH is maintained <7.2 by addition of sulphuric acid when required. The fermenter is harvested after 98 hours of fermentation. The production of the antibiotic NAI-130 is monitored by HPLC as previously described, after extracting the whole culture broth with twice the volume of methanol and stirring for one hour.

Example 3: Fermentation Method of Streptosporangium sp. DSM 24060

Streptosporangium sp. DSM 24060 is maintained on S1 plates (composed and prepared as described in Example 1) for 2-3 weeks at 28° C. The microbial content of one plate is scraped and inoculated into 50 mL Erlenmeyer flasks containing 15 mL of seed medium (composed and prepared as described in Example 1). The inoculated flasks are grown at 28° C., on a rotatory shaker operating at 200 rpm. After 3-4 days, 5% of this culture is inoculated into 500 mL Erlenmeyer flasks containing 100 mL of the same medium. After 72 hours of incubation, 120 mL are transferred into 3 L bioreactor containing 2 L of the production medium composed of (g/L): maize dextrin 20, glucose 10, yeast extract 2, casein hydrolysed 4, meat extract 4 and calcium carbonate 3. The medium is prepared in deionized water and the pH adjusted to 7.2 before sterilization at 121° C. for 25 min, while glucose is sterilized separately and added after cooling. The fermentation is carried out at 30° C., with 600 rpm stirring and 0.5 vvm aeration. During the fermentation pH is maintained <7.2 by addition of sulphuric acid when required. The fermenter is harvested after 96 hours of fermentation. The production of the antibiotic NAI-114 is monitored by HPLC as previously described, after extracting the whole culture broth with twice the volume of methanol and stirring for one hour.

Example 4: Fermentation Method of Streptomyces sp. DSM 24056

Streptomyces sp. DSM 24056 is maintained on S1 plates (composed and prepared as described in Example 1) for 2-3 weeks at 28° C. The microbial content of one plate is scraped and inoculated into 50 mL Erlenmeyer flasks containing 15 mL of seed medium (composed and prepared as described in Example 1). The inoculated flasks are grown at 28° C., on a rotatory shaker operating at 200 rpm. After 2-3 days, 5% of this culture is inoculated into 500 mL Erlenmeyer flasks containing 100 mL of the same medium. After 48 hours of incubation, 100 mL are transferred into 3 L bioreactor containing 2 L of the production medium composed of (g/L): glycerol 30, soybean meal 15, NaCl2, calcium carbonate 5. The medium was prepared in deionized water and the pH adjusted to 7.2 before sterilization at 121° C. for 25 min. The fermentation is carried out at 30° C., with 600 rpm stirring and 0.5 vvm aeration. During the fermentation pH is maintained <7.2 by addition of sulphuric acid when required. The fermenter is harvested after 120 hours of fermentation. The production of the antibiotic NAI-438 is monitored by HPLC as previously described, after extracting the whole culture broth with twice the volume of methanol and stirring for one hour.

Example 5: Alternative Fermentation Method of STREPTOMYCES sp. DSM 24069

Streptomyces sp. DSM 24069 is maintained on BTT-agar plates for 2-3 weeks at 28° C. BTT-agar is composed of (g/L): glucose 10, yeast extract 1, meat extract 1, casitone 1, agar 18. Medium is prepared in distilled water and pH adjusted to 7.3 before sterilization at 121° C. for 20 min. The microbial content of one plate is scraped and inoculated into 50 mL Erlenmeyer flasks containing 15 mL of seed medium (composed and prepared as described in Example 1). The inoculated flasks are grown at 28° C., on a rotatory shaker operating at 200 rpm. After 2-3 days, 5% of this culture is inoculated into 500 mL Erlenmeyer flasks containing 100 mL of the same medium. After 72 hours of incubation, 100 mL are transferred into 3 L bioreactor containing 2 L of the production medium composed and prepared as described in Example 4. The fermentation is carried out at 30° C., with 400 rpm stirring and 0.5 vvm aeration. During the fermentation pH is maintained <7.2 by addition of sulphuric acid when required. The fermenter is harvested after 120 hours of fermentation. The production of the antibiotic NAI-857 is monitored by HPLC as previously described, after extracting the whole culture broth with twice the volume of methanol and stirring for one hour.

Example 6: Alternative Fermentation Method of STREPTOMYCES sp. DSM 24058

Streptomyces sp. DSM 24058 is maintained on BTT-agar plates (composed and prepared as described in Example 5) for 2-3 weeks at 28° C. The microbial content of one plate is scraped and inoculated into 50 mL Erlenmeyer flasks containing 15 mL of seed medium composed of (g/L): dextrose monohydrate 10, maize dextrin 24, yeast extract 5, soya peptone 5. Medium is prepared in distilled water and pH adjusted to 7.2 before sterilization at 121° C. for 20 min. After 3-4 days, 5% of this culture is inoculated into 500 mL Erlenmeyer flasks containing 100 mL of the same medium. After 48 hours of incubation, 120 mL are transferred into 3 L bioreactor containing 2 L of the production medium composed and prepared as described in Example 3. The fermentation is carried out at 30° C., with 500 rpm stirring and 0.6 vvm aeration. During the fermentation pH is maintained <7.2 by addition of sulphuric acid when required. The fermenter is harvested after 120 hours of fermentation. The production of the antibiotic NAI-130 is monitored by HPLC as previously described, after extracting the whole culture broth with twice the volume of methanol and stirring for one hour.

Example 7: Recovery and Purification of Antibiotic NAI-857 (Compound of Formula (I) Wherein X is Ile, Y is Tyr, n is 1, $R_1$ and $R_2$ are OH)

The fermentation broth (10 L) described in the Example 1 is added of 2.5 L of methanol and the pH lowered to 4.5 by addition of AcOH (80 mL). The mixture is shaken for 1 hour at room temperature and filtered with filter paper. Antibiotic NAT-857 is found mainly in the cleared broth The filtered broth is concentrated to 3.6 L and then 300 mL of Diaion HP-20 polystyrenic resin were added; the mixture is stirred 3 h at room temperature and then the resin is recovered, washed with 1.2 L methanol:water 35:75 (v/v) and then eluted with 3 L methanol:water 9:1 (v/v) stirring overnight at room temperature. The eluted fraction containing antibiotic NAI-857 is concentrated to small volume on a rotary evaporator and maintained at 4° C. overnight. The formed precipitate is collected by filtration obtaining 3.4 g of crude antibiotic NAT-857. The solid is suspended in acetone (20 mL), stirred for 30 minutes at room temperature and filtered thus obtaining 1.8 g of NAT-857 as a beige powder.

Antibiotic NAT-857 (100 mg) was further purified by medium pressure chromatography on reverse phase C18 RediSep Column, 86 g, (Teledyne ISCO, Nebraska, USA) by using a CombiFlash Medium Pressure Chromatography System (Teledyne ISCO, Nebraska, USA) with a detection wavelength (230 nm). Phase A is 50 mM ammonium formate buffer (pH 6.6) and phase B is acetonitrile. The resin is previously conditioned with a mixture of phase A:phase B 9:1 (v/v) and is then eluted at 60 mL/min with linear gradient from 10% to 90% of phase B in 17 min. The fractions containing antibiotic NAT-857 are pooled, concentrated under vacuum and lyophilized from water, yielding 45 mg of purified antibiotic NAI-857.

Example 8: Recovery and Purification of Antibiotic NAI-130 (Compound of Formula (I) Wherein X is Val, Y is Tyr n is 1, $R_1$ and $R_2$ are OH)

The fermentation broth (2.2 L) described in the Example 2 was added with 550 mL of methanol and the pH lowered to 3.8 by addition of AcOH. The mixture was shaken for at room temperature overnight and filtered on Buchner. The filtered solution was evaporated to reduced volume (IL) and added with 50 mL of Diaion HP-20 polystyrenic resin. The suspension was then stirred 3 h at room temperature. Diaion HP-20 polystyrenic was recovered by filtration, washed with methanol:water 30:70 (v/v, 4×20 mL) and eluted batchwise with methanol:water 9:1 (v/v, 200 mL). The eluted fractions containing antibiotic NAI-130 were concentrated to small volume on a rotary evaporator. The concentrated solution was maintained at 4° C. overnight. The formed precipitated was collected by filtration obtaining 300 mg of crude antibiotic. The solid was purified by medium-pressure liquid chromatography on reverse phase C18 RediSep Column, (Teledyne ISCO, Nebraska, USA) by using a CombiFlash Medium Pressure Chromatography System (Teledyne ISCO, Nebraska, USA) with a detection wavelength (230 nm). Phase A is 50 mM ammonium formate buffer (pH 6.6) and phase B is acetonitrile. The resin is previously conditioned with a mixture of phase A:phase B 9:1 (v/v) and is then eluted at 60 mL/min with linear gradient from 10% to 90% of phase B in 17 min. Fractions containing NAI-130 were evaporated at reduced pressure to small volume and liophylazed obtaining 120 mg of NAI-130.

Example 9: Recovery of Antibiotic NAI-114 (Compound of Formula (I) Wherein X is Ile, Y is Trp n is 2, $R_1$ and $R_2$ are OH)

To the fermentation broth (2 L) described in the Example 3 methanol (2 L) was added and the mixture was shaken for 1 h at room temperature and filtered on a Buchner funnel to remove the mycelium. The filtered solution was concentrated to 1 L and then added with 120 mL of Diaion HP-20 polystyrenic resin. The suspension was stirred for 1.5 h at room temperature and the resin was recovered by filtration on a Buchner funnel. The resin was then washed with 1 L of a solution of methanol:water 30:70 for 1 h at room temperature. The resin was filtered on a Buchner funnel, poured into IL of a solution of methanol:water 9:1 and stirred for an 1 h at room temperature. The filtered solution was evaporated in vacuum to give the crude product NAI-114 which was further purified by medium-pressure liquid chromatography. Instruments: Isco Combiflash. Phase A. TFA 0.1% Phase B: MeCN. Gradient: 0-20 minutes (linear 10-50% of acetonitrile). The fractions containing NAI-114 were evaporated at reduced pressure to small volume and lyophilized to obtain 60 mg of NAI-114.

Example 10: Recovery and Purification of Antibiotic NAI-438 (Compound of Formula (I) Wherein X is Ile, Y is Tyr n is 2, $R_1$ and $R_2$ are OH)

To part of the fermentation broth (0.2 L) described in the Example 4 were added 50 mL of methanol, the mixture was and the mixture is shaken for 1 hour at room temperature followed by filtration on a Buchner funnel to remove the mycelium. The filtered solution was concentrated to 100 mL and then added to 20 mL of Diaion HP-20 polystyrenic resin. The suspension was stirred for 2 h at room temperature and the resin was recovered by filtration on a Buchner funnel. The resin was then washed with 100 mL of a solution of methanol:water 30:70 for 1 h at room temperature. The resin was then filtered on a Buchner funnel, poured into 100 mL of a solution of methanol:water 9:1 and stirred for an additional 1 h at room temperature. The filtered solution was evaporated in vacuum to give the crude product NAI-438 which was further purified by medium-pressure liquid chromatography. Instruments: Isco Combiflash. Phase A. TFA 0.1% Phase B: MeCN. Gradient: 0-20 minutes (linear 10-50% of acetonitrile), The fractions containing NAI-438 were evaporated at reduced pressure to small volume and lyophilized to obtain 4 mg of NAI-438.

Example 11: Synthesis of NAI-857 Diamide with Ethylendiamine (Compound of Formula (I) Wherein X is Ile, Y is Tyr, n is 1, $R_1$ or $R_2$ is —$NHCH_2CH_2NH_2$)

To a stirred solution of 30 mg of NAI-857, prepared as described under Example 7, in 1.2 mL of DMF, 4 µL of ethylendiamine and 8 mg of PyBOP are added and the reaction is kept under stirring at room temperature for 20 minutes; after that time HPLC-MS analysis shows one major double charged peak of m/z 1128 amu corresponding to the diamide derivative. The reaction mixture solution is then adsorbed on 4.3 g reverse-phase C18 RediSep Column, (Teledyne ISCO, Nebraska, USA) and purified by using a CombiFlash Medium Pressure Chromatography System (Teledyne ISCO, Nebraska, USA) with a detection wavelength (230 nm). The resin is previously conditioned with a mixture of phase A:phase B 9.5:0.5 (v/v) and is then eluted at 18 mL/min with linear gradient from 5% to 90% of phase B in 18 min. Phase A is TFA 0.1% and phase B is acetonitrile. The fractions containing the diamide derivative are pooled, concentrated under vacuum and lyophilized from water, yielding 10 mg of purified NAI-857-diamide derivative. MS analysis shows a doubly protonated ion at m/z 1128.

Example 12: Synthesis of NAI-114 Diamide with Ethylendiamine (Compound of Formula (I) Wherein X is Ile, Y is Trp, n is 2, $R_1$ or $R_2$ is —$NHCH_2CH_2NH_2$)

To a stirred solution of 10 mg of NAI-114, prepared as described under Example 9, in 0.5 mL of DMF, 1 µL of ethylendiamine and 8.8 mg of PyBOP are added and the reaction is kept under stirring at room temperature for 1 hour; after that time HPLC-MS analysis shows one major double charged peak of m/z 1146 amu corresponding to the diamide derivative. The reaction mixture solution is then adsorbed on 4.3 g reverse-phase C18 RediSep Column, (Teledyne ISCO, Nebraska, USA) and purified by using a CombiFlash Medium Pressure Chromatography System (Teledyne ISCO, Nebraska, USA) with a detection wavelength (214 nm). The resin is previously conditioned with a mixture of phase A:phase B 9.5:0.5 (v/v) and is then eluted at 18 mL/min with linear gradient from 5% to 90% of phase B in 18 min. Phase A is TFA 0.1% and phase B is acetonitrile. The fractions containing the diamide derivative are pooled, concentrated under vacuum and lyophilized from water, yielding 2 mg of purified NAI-114-diamide derivative. MS analysis shows a doubly protonated ion at m/z 1146.

Example 13: In Vitro Antibacterial Activity of NAI-857, NAI-130, NAI-114, NAI-438 and their Diamides with Ethylendiamine (NAI-857 Derivative, NAI-130 Derivative, NAI-114 Derivative, NAI-438 Derivative)

Minimal inhibitory concentrations (MICs) for aerobic bacteria are determined by broth microdilution methodology, according to Clinical and Laboratory Standards Institute guidelines (CLSI documents M100-S16 and M27-A, NCCLS, Wayne, Pa.) using inocula of $1\text{-}5 \times 10^5$ CFU/mL for Gram positive and negative bacteria and $1 \times 10^4$ CFU/mL for *Candida albicans*.

Test results are scored after 20-24 hours of incubation at 35° C. for all tested strains, with the exception of *C. albicans*, which is incubated for 48 hours.

*Staphylococcus aureus*, enterococci, *Escherichia coli* and *Moraxella catharralis* strains are grown in Cation Adjusted Mueller Hinton (CAMHB) broth, streptococci isolates in Todd Hewitt broth and *Candida albicans* in RPMI-1640. All media are from Difco Laboratories, Detroit, Mich., USA. The effect of 30% bovine serum is determined under the same experimental conditions. MICs for anaerobic bacteria are determined by the broth dilution method in *Brucella* broth (BB) supplemented with hemin (5 µg/mL), vitamin K1 (1 µg/mL), lysed horse blood (5%) and Oxyase (1:25 v/v) (CLSI documents M11-A6, NCCLS, Wayne, Pa.).

Inocula are prepared by suspending few colonies from a 48-hours agar plate in BB to an $OD_{625}$=0.8, which is then diluted 1:10 to achieve a final suspension of about $10^5$ CFU/mL. Plates are incubated at 37° C. under anaerobic atmosphere (80% $NO_2$, 10% $CO_2$ and 10% $H_2$, GasPak EZ anaerobe container system, Becton Dickinson, Italy) for 48 hours.

All strains used are clinical isolates or strains from American Type Culture Collection (ATCC). The results of the tests are reported in Table 2.

Compounds NAI-857 (prepared as described under Example 7), NAI-130 (prepared as described under Example 8), NAI-114 (prepared as described under Example 9), NAI-857 diamide with ethylendiamine (prepared as described under Example 1), NAI-114 diamide with ethylendiamine (prepared as described under Example 12), and vancomycin (VA) are dissolved in DMSO to obtain a 10 mg/mL stock solution, and subsequently diluted in the test media to obtain working solutions. Microplates are always pre-coated with 0.02% bovine serum albumine to prevent non-specific adhesion of compounds.

TABLE II

Antimicrobial activity of lantibiotics NAI-857, NAI-130, NAI-114, NAI-857 diamide with ethylendiamine and NAI-114 diamide with ethylendiamine against aerobic bacteria.

| Microorganism | code | NAI-114 | NAI-130 | NAI-857 | NAI-114 diamide | NAI-857 diamide | VA |
|---|---|---|---|---|---|---|---|
| *Staphylococcus aureus* Met-S ATCC6538P | 100 | 8 | 64 | 16 | 1 | 0.5 | 0.25 |
| *S. aureus* ATCC 25923 | | 32 | >128 | na | 2 | na | 1 |
| *S. aureus* ATCC19636 | 819 | 64 | >128 | 64 | 2 | ≤0.125 | 0.5 |
| +serum 30% | | 128 | >128 | 128 | 4 | 4 | 1 |
| *Staphylococcus aureus* Met-R | 1400 | 32 | >128 | 128 | 2 | 0.5 | 0.5 |
| *Streptococcus pneumoniae* | 44 | 16 | >128 | 64 | 1 | 2 | 0.5 |
| *S. pyogenes* | 49 | 1 | 16 | 1 | <0.5 | 0.50 | 0.25 |
| *Enterococcus faecium* VanS | 568 | 256 | >128 | >128 | 8 | 16 | 2 |
| +serum 30% | | >512 | >128 | >128 | 32 | 64 | 2 |
| *E. faecium* VanA | 569 | 512 | >128 | >128 | 8 | 16 | >128 |
| *E. faecalis* VanS | 559 | 256 | 128 | 128 | 32 | 32 | 1 |
| +serum 30% | | >512 | >128 | >128 | 64 | 64 | 2 |
| *E. faecalis* VanA | 560 | 256 | 128 | >128 | 32 | 64 | 2 |
| *Escherichia coli* ATCC QC | 25922 | >512 | >128 | >128 | >512 | >128 | >128 |
| *Candida albicans* | 145 | >512 | >128 | >128 | >512 | >128 | >128 |

VA = vancomycin,
code = internal code for clinical isolates

What is claimed is:

1. A method for the treatment of bacterial infections, said method comprising administering a compound of formula (I) (SEQ ID No. 5)

FORMULA (I)

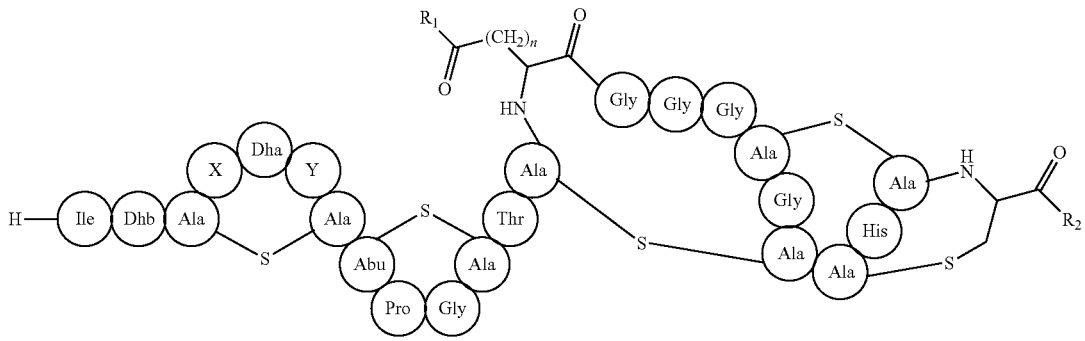

wherein X represents an aliphatic amino acid chosen among Ala, Leu, or Ile; Y represents an aromatic amino chosen among Phe, Tyr, Trp, or His; n is 1 or 2, and $R_1$ and $R_2$ independently represent OH or $NR_3R_4$ wherein $R_3$ and $R_4$ independently represent:

- hydrogen or
- an alkyl of 1 to 20 carbon atoms or
- an alkenyl of 2 to 20 carbon atoms or
- an alkynyl of 2 to 20 carbon atoms or
- a cycloalkyl of 3 to 8 carbon atom optionally substituted by one or two substituents independently selected from the group consisting of halo, cyano, (C1-C4)alkyl optionally substituted by 1 to 3 halogen atoms, (C1-C4)alkoxy optionally substituted by 1 to 3 halogen atoms, phenyl, phenyl-(C1-C4)alkyl, phenoxy, and phenoxy-(C1-C4)alkyl wherein each of phenyl, phenyl portion of the phenyl (C1-C4), alkoxy, phenoxy, phenoxy portion of the phenoxy-(C1-C4)alkyl group is optionally substituted by 1 to 3 halogen atoms, and (C1-C4)alkoxy optionally substituted by 1 to 3 halogen atoms or
- a phenyl radical optionally substituted by one or two substituents independently selected from the group consisting of halo, cyano, (C1-C4)alkyl optionally substituted by 1 to 3 halogen atoms, (C1-C4)alkoxy optionally substituted by 1 to 3 halogen atoms, phenyl, phenyl-(C1-C4)alkyl, phenoxy, and phenoxy-(C1-C4) alkyl wherein each of phenyl, phenyl portion of the phenyl (C1-C4), alkoxy, phenoxy, phenoxy portion of the phenoxy-(C1-C4)alkyl group is optionally substituted by 1 to 3 halogen atoms, and (C1-C4)alkoxy optionally substituted by 1 to 3 halogen atoms or
- a benzyl radical optionally substituted on the phenyl ring by one or two substituents independently selected from the group consisting of halo, cyano, (C1-C4)alkyl optionally substituted by 1 to 3 halogen atoms, (C1-C4)alkoxy optionally substituted by 1 to 3 halogen atoms, phenyl, phenyl-(C1-C4)alkyl, phenoxy, and phenoxy-(C1-C4)alkyl wherein each of phenyl, phenyl portion of the phenyl (C1-C4), alkoxy, phenoxy, phenoxy portion of the phenoxy-(C1-C4)alkyl group is optionally substituted by one or two substituents selected from the group consisting of halo, cyano, (C1-C4)alkyl optionally substituted by 1 to 3 halogen atoms, and (C1-C4)alkoxy optionally substituted by 1 to 3 halogen atoms or
- a naphthyl radical optionally substituted by one or two substituents selected from the group consisting of halo, (C1-C4) alkyl optionally substituted by 1 to 3 halogen atoms, and (C1-C4)alkoxy optionally substituted by 1 to 3 halogen atoms or
- a group of formula

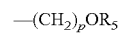
—(CH$_2$)$_p$OR$_5$ in which p represents an integer from 2 to 8 and $R_5$ represents
- hydrogen or
- (C$_1$-C$_4$) alkyl or
- a cycloalkyl of 3 to 8 carbon atom optionally substituted by one or two substituents independently selected from the group consisting of halo, cyano, (C1-C4)alkyl optionally substituted by 1 to 3 halogen atoms, (C1-C4)alkoxy optionally substituted by 1 to 3 halogen atoms, phenyl, phenyl-(C1-C4)alkyl, phenoxy, and phenoxy-(C1-C4)alkyl wherein each of phenyl, phenyl portion of the phenyl (C1-C4), alkoxy, phenoxy, phenoxy portion of the phenoxy-(C1-C4)alkyl group is optionally substituted by one or two substituents selected from the group consisting of halo, cyano, (C1-C4)alkyl optionally substituted by 1 to 3 halogen atoms, and (C1-C4)alkoxy optionally substituted by 1 to 3 halogen atoms or
a phenyl radical optionally substituted by one or two substituents independently selected from the group consisting of halo, cyano, (C1-C4)alkyl optionally substituted by 1 to 3 halogen atoms, (C1-C4)alkoxy optionally substituted by 1 to 3 halogen atoms, phenyl, phenyl-(C1-C4)alkyl, phenoxy, and phenoxy-(C1-C4)alkyl wherein each of phenyl, phenyl portion of the phenyl (C1-C4), alkoxy, phenoxy, phenoxy portion of the phenoxy-(C1-C4)alkyl group is optionally substituted by one or two substituents selected from the group consisting of halo, cyano, (C1-C4)alkyl optionally substituted by 1 to 3 halogen atoms, and (C1-C4)alkoxy optionally substituted by 1 to 3 halogen atoms or
a group of formula —(CH$_2$)$_q$NR$_6$R$_7$ in which q represents an integer from 2 to 8 and R$_6$ and R$_7$ independently represent
hydrogen or
(C$_1$-C$_4$) alkyl or
a cycloalkyl of 3 to 8 carbon atom optionally substituted by one or two substituents independently selected from the group consisting of halo, cyano, (C1-C4)alkyl optionally substituted by 1 to 3 halogen atoms, (C1-C4)alkoxy optionally substituted by 1 to 3 halogen atoms, phenyl, phenyl-(C1-C4)alkyl, phenoxy, and phenoxy-(C1-C4)alkyl wherein each of phenyl, phenyl portion of the phenyl (C1-C4), alkoxy, phenoxy, phenoxy portion of the phenoxy-(C1-C4)alkyl group is optionally substituted by one or two substituents selected from the group consisting of halo, cyano, (C1-C4)alkyl optionally substituted by 1 to 3 halogen atoms, and (C1-C4)alkoxy optionally substituted by 1 to 3 halogen atoms or
a phenyl radical optionally substituted by one or two substituents independently selected from the group consisting of halo, cyano, (C1-C4)alkyl optionally substituted by 1 to 3 halogen atoms, (C1-C4)alkoxy optionally substituted by 1 to 3 halogen atoms, phenyl, phenyl-(C1-C4)alkyl, phenoxy, and phenoxy-(C1-C4)alkyl wherein each of phenyl, phenyl portion of the phenyl (C1-C4), alkoxy, phenoxy, phenoxy portion of the phenoxy-(C1-C4)alkyl group is optionally substituted by 1 to 3 halogen atoms, and (C1-C4)alkoxy optionally substituted by 1 to 3 halogen atoms or
a benzyl radical optionally substituted on the phenyl ring by one or two substituents independently selected from the group consisting of halo, cyano, (C1-C4)alkyl optionally substituted by 1 to 3 halogen atoms, (C1-C4)alkoxy optionally substituted by 1 to 3 halogen atoms, phenyl, phenyl-(C1-C4)alkyl, phenoxy, and phenoxy-(C1-C4)alkyl wherein each of phenyl, phenyl portion of the phenyl (C1-C4), alkoxy, phenoxy, phenoxy portion of the phenoxy-(C1-C4)alkyl group is optionally substituted by one or two substituents selected from the group consisting of halo, cyano, (C1-C4)alkyl optionally substituted by 1 to 3 halogen atoms, and (C1-C4)alkoxy optionally substituted by 1 to 3 halogen atoms; and
R$_6$ and R$_7$ taken together represent a —(CH$_2$)$_3$—, —(CH$_2$)$_4$—, —(CH$_2$)$_2$—O—(CH$_2$)$_2$, —(CH$_2$)$_2$—S—(CH$_2$)$_2$ or R$_6$ and R$_7$ taken together with the adjacent nitrogen atom represent: a piperazine moiety which may be substituted in position 4 with a substituent selected from the group consisting of (C$_1$-C$_4$) alkyl, (C$_3$-C$_8$) cycloalkyl, pyridyl, benzyl, and substituted benzyl wherein the phenyl moiety bears 1 or 2 substituents selected from the group consisting of chloro, bromo, nitro, (C$_1$-C$_4$) alkyl, and (C$_1$-C$_4$) alkoxy.

2. The method according to claim 1, wherein R$_1$ and R$_2$ are OH.

3. The method according to claim 1, wherein R$_1$ and R$_2$ are NR$_3$R$_4$, and wherein R$_3$ and R$_4$ independently represent:
an alkyl of 1 to 12 carbon atoms or
an alkenyl of 3 to 10 carbon atoms or
a cycloalkyl of 5 to 6 carbon atom optionally substituted by one or two substituents independently selected from the group consisting of (C1-C4)alkyl, (C1-C4)alkoxy, phenyl, phenyl-(C1-C4)alkyl, phenoxy, and phenoxy-(C1-C4)alkyl wherein each of phenyl, phenyl portion of the phenyl (C1-C4), alkoxy, phenoxy, phenoxy portion of the phenoxy-(C1-C4)alkyl group is optionally substituted by one or two substituents selected from the group consisting of halo, (C1-C4)alkyl, and (C1-C4) alkoxy or
a phenyl radical optionally substituted by one or two substituents independently selected from the group consisting of halo, (C1-C4)alkyl, (C1-C4)alkoxy, phenyl, phenyl-(C1-C4)alkyl, phenoxy, and phenoxy-(C1-C4)alkyl or
a benzyl radical optionally substituted on the phenyl ring by one or two substituents independently selected from the group consisting of halo, cyano, (C1-C4)alkyl, (C1-C4)alkoxy, phenyl, phenyl-(C1-C4)alkyl, phenoxy, and phenoxy-(C1-C4)alkyl or
a naphthyl radical optionally substituted by one or two substituents selected from the group consisting of halo, (C1-C4)alkyl, and (C1-C4)alkoxy or
a group of formula —(CH$_2$)$_p$OR$_5$ in which p represents an integer from 2 to 5 and R$_5$ represent
hydrogen or
(C$_1$-C$_4$) alkyl or
a cycloalkyl of 5 to 6 carbon atom optionally substituted by one or two substituents independently selected from the group consisting of halo, cyano, (C1-C4)alkyl, (C1-C4)alkoxy, phenyl, phenyl-(C1-C4)alkyl, phenoxy, and phenoxy-(C1-C4)alkyl or
a phenyl radical optionally substituted by one or two substituents independently selected from the group consisting of halo, cyano, (C1-C4)alkyl, (C1-C4) alkoxy, phenyl, phenyl-(C1-C4)alkyl, phenoxy, and phenoxy-(C1-C4)alkyl; or
a group of formula —(CH$_2$)$_q$NR$_6$R$_7$ in which q represents an integer from 2 to 8 and R$_4$ and R$_5$ independently represent
hydrogen or
(C$_1$-C$_4$) alkyl or
a cycloalkyl of 3 to 6 carbon atom optionally substituted by one or two substituents independently selected from the group consisting of halo, cyano, (C1-C4)alkyl, lower alkoxy of 1 to 4 carbon, phenyl, phenyl-(C1-C4)alkyl, phenoxy, and phenoxy-(C1-C4)alkyl wherein each of phenyl, phenyl portion of the phenyl (C1-C4), alkoxy, phenoxy, phenoxy portion of the phenoxy-(C1-C4)alkyl group is optionally substituted by one or two substituents selected from the group consisting of halo, cyano, lower alkyl of 1 to 4 carbon, and (C1-C4)alkoxy or a phenyl radical optionally substituted by one or two substituents independently selected from the group consisting of halo, (C1-C4)alkyl, (C1-C4)alkoxy, phenyl, phenyl-(C1-C4)alkyl, phenoxy, and phenoxy-(C1-C4)alkyl or a benzyl radical optionally substituted on the phenyl ring by one or two substituents independently selected from the group consisting of halo, cyano, (C1-C4)alkyl, (C1-C4)alkoxy, phenyl, phenyl-(C1-C4)alkyl, phenoxy, phenoxy-(C1-C4)alkyl; and $R_6$ and $R_7$ taken together represent a $-(CH_2)_3$, $-(CH_2)_4-$, $-(CH_2)_2-O-(CH_2)_2$, $-(CH_2)_2-S-(CH_2)_2$ or $R_6$ and $R_7$ taken together with the adjacent nitrogen atom represent: a piperazine moiety which may be substituted in position 4 with a substituent selected from the group consisting of $(C_1-C_4)$ alkyl, $(C_3-C_8)$ cycloalkyl, pyridyl, benzyl, and substituted benzyl wherein the phenyl moiety bears 1 or 2 substituents selected from the group consisting to chloro, bromo, nitro, $(C_1-C_4)$ alkyl, and $(C_1-C_4)$ alkoxy.

4. The method according to claim 2, wherein X is Ile, Y is Tyr, n is 1, and $R_1$ and $R_2$ are OH (NAI-857).

5. The method according to claim 2, wherein X is Ile, Y is Trp, n is 2, and $R_1$ and $R_2$ are OH (NAI-114).

6. The method according to claim 2, wherein X is Ile, Y is Tyr, n is 2, and $R_1$ and $R_2$ are OH (NAI-438).

7. The method according to claim 3 wherein $-NR_3R_4$ has the following formula:

—NH—(CH$_2$)$_2$—NH$_2$;  —NH(CH$_2$)$_3$NH$_2$

—NH—(CH$_2$)$_4$—NH$_2$;  —NH(CH$_2$)$_3$NHCH$_3$

—NH—(CH$_2$)$_3$—N(CH$_3$)$_2$;  —NH—(CH$_2$)$_3$N(C$_2$H$_5$)$_2$

—NH—(CH$_2$)$_3$N(C$_3$H$_7$)$_2$;  —NH—(CH$_2$)$_3$N(C$_4$H$_9$)$_2$

—NH—(CH$_2$)$_5$N(CH$_3$)$_2$;  —NH(CH$_2$)$_6$N(CH$_3$)$_2$

—NH(CH$_2$)$_6$NHCH$_3$;  —N[(CH$_2$)$_2$NH$_2$]$_2$

—N[(CH$_2$)$_3$NH$_2$]$_2$;  —N[(CH$_2$)$_2$N(CH$_3$)$_2$]$_2$

—N[(CH$_2$)$_3$N(CH$_3$)$_2$]$_2$;  —N[(CH$_2$)$_4$NH$_2$]$_2$

[Chemical structures showing various amine substituents including piperidinyl-, pyrrolidinyl-, thiomorpholinyl-, piperidinyl-butyl-, morpholinyl-, piperidinyl-, piperazinyl-butyl, cyclopentyl-piperazinyl-, pyridyl-piperazinyl-, benzyl-piperazinyl-, N-methyl-piperazinyl-, N-ethyl-piperazinyl-, piperazinyl-NH, N-propyl-piperazinyl-, 4-nitrobenzyl-piperazinyl-, 4-chlorobenzyl-piperazinyl-, 4-methoxybenzyl-piperazinyl-]

8. The method according to claim 3, wherein said $NR_3R_4$ is selected among:

TABLE 1

| | $-NR_3R_4$ |
|---|---|
| 22. | —NH—cyclohexyl |

TABLE 1-continued

| | —NR₃R₄ |
|---|---|
| 23. |  |
| 24. | 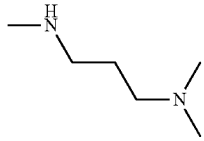 |
| 25. | 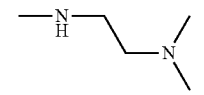 |
| 26. | 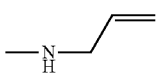 |
| 27. | 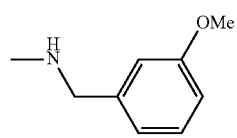 |
| 28. | 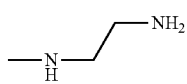 |
| 29. | 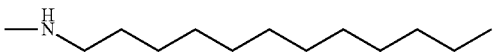 |
| 30. | 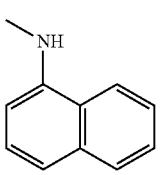 |
| 31. | 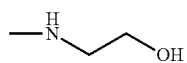 |
| 32. | 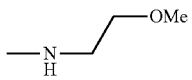 |
| 33. | 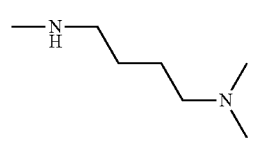 |
| 34. | 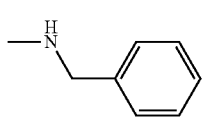 |
| 35. | 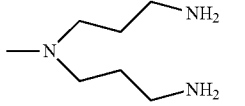 |
| 36. | 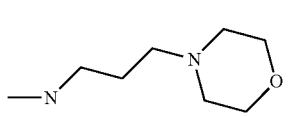 |

TABLE 1-continued

| | —NR₃R₄ |
|---|---|
| 37. | 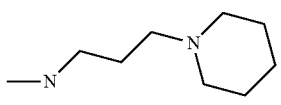 |
| 38. | 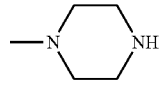 |
| 39. | 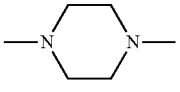 |
| 40. | 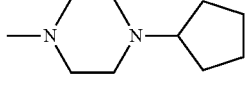 |
| 41. | 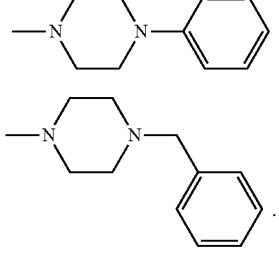 |
| 42. | 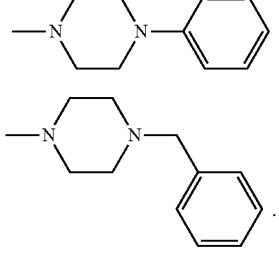 |

9. The method according to claim 1 wherein X is Ile, Y is Tyr, n is 1, and $R_1$ and $R_2$ are $NR_3R_4$ wherein $R_3$ (or $R_4$) is H, and $R_4$ (or $R_3$) is $(CH_2)qNR_6R_7$ with q=2, and $R_6$ and $R_7$ are H.

10. The method according to claim 1 wherein X is Ile, Y is Trp, n is 2, and $R_1$ and $R_2$ are $NR_3R_4$ wherein $R_3$ (or $R_4$) is H, and $R_4$ (or $R_3$) is $(CH_2)qNR_6R_7$ with q=2, and $R_6$ and $R_7$ are H.

11. A process for the preparation of compounds of formula (I) (SEQ ID No. 5) according to claim 1, said process comprising:
cultivating *Actinoplanes* sp. selected from the group consisting of *Streptomyces* sp. DSM 24056, *Streptomyces* sp. DSM 24058, *Streptosporangium* sp. DSM 24060, and *Streptomyces* sp. DSM 24069 under aerobic conditions, in an aqueous nutrient medium containing an assimilable source of carbon, nitrogen, and inorganic salts;
isolating resultant antibiotic of formula (I) (SEQ ID No. 5) from whole culture broth, or from separated mycelium or from filtered fermentation broth; and
purifying the isolated antibiotic of formula (I) (SEQ ID No. 5).

12. The process according to claim 11, wherein the strain *Actinoplanes* sp. selected from the group consisting of *Streptomyces* sp. DSM 24056, *Streptomyces* sp. DSM 24058, *Streptosporangium* sp. DSM 24060, and *Streptomyces* sp. DSM 24069 is pre-cultured.

13. The process according to claim 11, wherein the isolation of the antibiotic of formula (I) (SEQ ID No. 5) is carried out by filtering the fermentation broth and recovering the antibiotic from the filtered fermentation broth according to at least a technique selected from the group consisting of: extraction with a water-immiscible solvent, precipitation by adding a non-solvent or by changing the pH of the solution, absorption chromatography, partition chromatography, reverse phase partition chromatography, ion exchange chromatography, molecular exclusion chromatography, and a combination of two or more of said techniques.

14. The process according to claim 11, wherein the isolation of the antibiotic of formula (I) (SEQ ID No. 5) is carried out by separating the mycelium from the supernatant of the fermentation broth and extraction of the mycelium with a water-miscible solvent whereby, after the removal of the spent mycelium, obtaining a water-miscible solution containing the crude antibiotic, which is processed either separately or in pool with the filtered fermentation broth to recover the antibiotic selected from the group consisting of NAI-857, NAI-130, NAI-112, and NAI-438 by means of at least a technique selected from the group consisting of: extraction with a solvent, precipitation by adding a non-solvent or by changing the pH of the solution, absorption chromatography, partition chromatography, reverse phase partition chromatography, ion exchange chromatography and molecular exclusion chromatography, and a combination of two or more of said techniques.

15. The process according to claim 11, wherein X is Ile, Y is Tyr, n is 1, and $R_1$ and $R_2$ are OH (NAI-857).

16. The process according to claim 11, wherein X is Ile, Y is Trp, n is 2, and $R_1$ and $R_2$ are OH (NAI-114).

17. The process according to claim 11, wherein X is Ile, Y is Tyr, n is 2, and $R_1$ and $R_2$ are OH (NAI-438).

18. The process according to claim 11, further comprising a condensation reaction between at least a starting compound of formula (I) (SEQ ID No. 5) selected from the group consisting of NAI-857, NAI-114, and NAI-438, and at least a selected amine of general formula $HNR_3R_4$ in the presence of a condensing agent.

19. The process according to claim 18 wherein said $NR_3R_4$ are chosen among:

—NH—(CH$_2$)$_2$—NH$_2$;  —NH(CH$_2$)$_3$NH$_2$

—NH—(CH$_2$)$_4$—NH$_2$;  —NH(CH$_2$)$_3$NHCH$_3$

—NH—(CH$_2$)$_3$—N(CH$_3$)$_2$;  —NH—(CH$_2$)$_3$N(C$_2$H$_5$)$_2$

—NH—(CH$_2$)$_3$N(C$_3$H$_7$)$_2$;  —NH—(CH$_2$)$_3$N(C$_4$H$_9$)$_2$

—NH—(CH$_2$)$_5$N(CH$_3$)$_2$;  —NH(CH$_2$)$_6$N(CH$_3$)$_2$

—NH(CH$_2$)$_6$NHCH$_3$;  —N[(CH$_2$)$_2$NH$_2$]$_2$

—N[(CH$_2$)$_3$NH$_2$]$_2$;  —N[(CH$_2$)$_2$N(CH$_3$)$_2$]$_2$

—N[(CH$_2$)$_3$N(CH$_3$)$_2$]$_2$;  —N[(CH$_2$)$_4$NH$_2$]$_2$

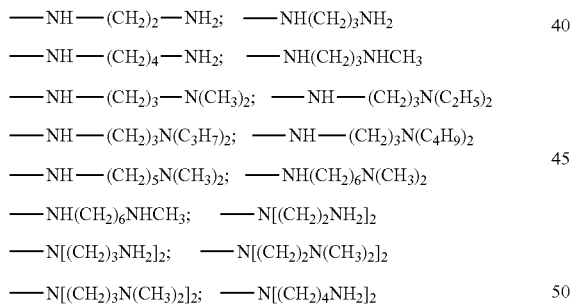

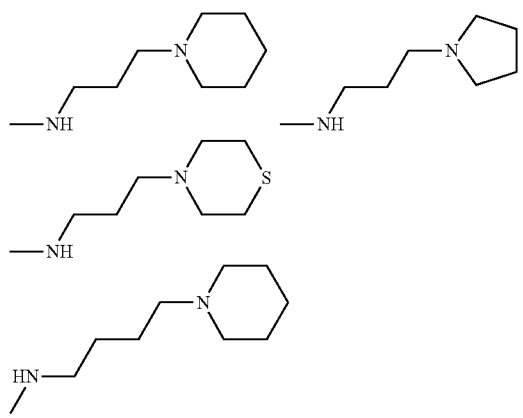

20. The process according to claim 18 wherein said $NR_3R_4$ are chosen among:

TABLE 1

| —$NR_3R_4$ |
|---|
| 1. 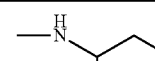 |
| 2.  |

TABLE 1-continued

| | —NR₃R₄ |
|---|---|
| 3. | 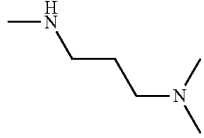 |
| 4. | 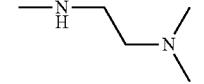 |
| 5. | 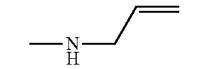 |
| 6. | 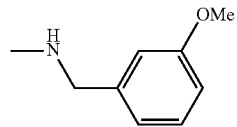 |
| 7. | 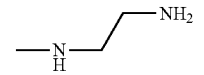 |
| 8. | 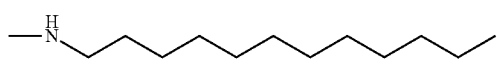 |
| 9. | 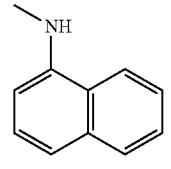 |
| 10. | 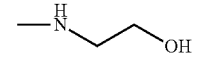 |
| 11. | 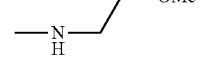 |
| 12. | 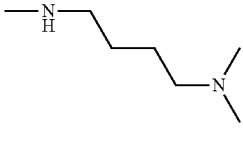 |
| 13. | 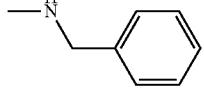 |
| 14. | 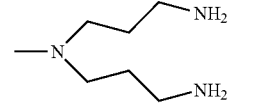 |
| 15. | 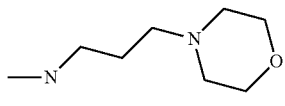 |
| 16. | 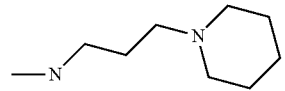 |

TABLE 1-continued

| | —NR₃R₄ |
|---|---|
| 17. | 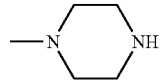 |
| 18. |  |
| 19. | 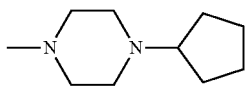 |
| 20. | 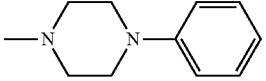 |
| 21. | 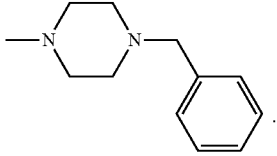 |

21. The process according to claim 18, wherein said condensation reaction is carried out in the presence of at least a condensing agent and at least a solvent selected from the group consisting of: organic amides, ethers of glycols and polyols, phosphoramide derivatives, sulfoxides dimethylformamide, dimethoxyethane, hexamethyl phosphoroamide, dimethylsulphoxide, dioxane, N-methylpyrrolidone, and mixtures thereof.

22. The process according to claim 18, wherein said condensation reaction is carried out at a temperature ranging from 0° C. to 50° C.

23. A compound of formula (I) (SEQ ID No. 5)

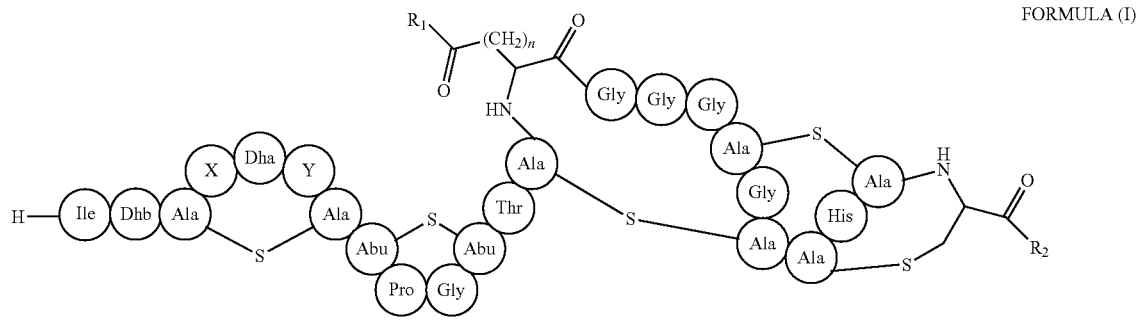

wherein X represents an aliphatic amino acid chosen among Ala, Leu, or Ile; Y represents an aromatic amino chosen among Phe, Tyr, Trp, or His; n is 1 or 2, and $R_1$ and $R_2$ independently represent OH or $NR_3R_4$ wherein $R_3$ and $R_4$ independently represent:
- hydrogen or
- an alkyl of 1 to 20 carbon atoms or
- an alkenyl of 2 to 20 carbon atoms or
- an alkynyl of 2 to 20 carbon atoms or
- a cycloalkyl of 3 to 8 carbon atom optionally substituted by one or two substituents independently selected from the group consisting of halo, cyano, (C1-C4)alkyl optionally substituted by 1 to 3 halogen atoms, (C1-C4)alkoxy optionally substituted by 1 to 3 halogen atoms, phenyl, phenyl-(C1-C4)alkyl, phenoxy, and phenoxy-(C1-C4)alkyl wherein each of phenyl, phenyl portion of the phenyl (C1-C4), alkoxy, phenoxy, phenoxy portion of the phenoxy-(C1-C4)alkyl group is optionally substituted by 1 to 3 halogen atoms, and (C1-C4)alkoxy optionally substituted by 1 to 3 halogen atoms or
- a phenyl radical optionally substituted by one or two substituents independently selected from the group consisting of halo, cyano, (C1-C4)alkyl optionally substituted by 1 to 3 halogen atoms, (C1-C4)alkoxy optionally substituted by 1 to 3 halogen atoms, phenyl, phenyl-(C1-C4)alkyl, phenoxy, and phenoxy-(C1-C4) alkyl wherein each of phenyl, phenyl portion of the phenyl (C1-C4), alkoxy, phenoxy, phenoxy portion of the phenoxy-(C1-C4)alkyl group is optionally substituted by 1 to 3 halogen atoms, and (C1-C4)alkoxy optionally substituted by 1 to 3 halogen atoms or
- a benzyl radical optionally substituted on the phenyl ring by one or two substituents independently selected from the group consisting of halo, cyano, (C1-C4)alkyl optionally substituted by 1 to 3 halogen atoms, (C1-C4)alkoxy optionally substituted by 1 to 3 halogen atoms, phenyl, phenyl-(C1-C4)alkyl, phenoxy, and phenoxy-(C1-C4)alkyl wherein each of phenyl, phenyl portion of the phenyl (C1-C4), alkoxy, phenoxy, phenoxy portion of the phenoxy-(C1-C4)alkyl group is optionally substituted by one or two substituents selected from the group consisting of halo, cyano, (C1-C4)alkyl optionally substituted by 1 to 3 halogen atoms, and (C1-C4)alkoxy optionally substituted by 1 to 3 halogen atoms or
- a naphthyl radical optionally substituted by one or two substituents selected from the group consisting of halo, (C1-C4) alkyl optionally substituted by 1 to 3 halogen atoms, and (C1-C4)alkoxy optionally substituted by 1 to 3 halogen atoms or
- a group of formula $$-(CH_2)_pOR_5$$

in which p represents an integer from 2 to 8 and $R_5$ represents
- hydrogen or
- $(C_1-C_4)$ alkyl or
- a cycloalkyl of 3 to 8 carbon atom optionally substituted by one or two substituents independently selected from the group consisting of halo, cyano, (C1-C4)alkyl optionally substituted by 1 to 3 halogen atoms, (C1-C4)alkoxy optionally substituted by 1 to 3 halogen atoms, phenyl, phenyl-(C1-C4)alkyl, phenoxy, and phenoxy-(C1-C4)alkyl wherein each of phenyl, phenyl portion of the phenyl (C1-C4), alkoxy, phenoxy, phenoxy portion of the phenoxy-(C1-C4)alkyl group is optionally substituted by one or two substituents selected from the group consisting of halo, cyano, (C1-C4)alkyl optionally substituted by 1 to 3 halogen atoms, and (C1-C4)alkoxy optionally substituted by 1 to 3 halogen atoms or
- a phenyl radical optionally substituted by one or two substituents independently selected from the group consisting of halo, cyano, (C1-C4)alkyl optionally substituted by 1 to 3 halogen atoms, (C1-C4)alkoxy optionally substituted by 1 to 3 halogen atoms, phenyl, phenyl-(C1-C4)alkyl, phenoxy, and phenoxy-(C1-C4)alkyl wherein each of phenyl, phenyl portion of the phenyl (C1-C4), alkoxy, phenoxy, phenoxy portion of the phenoxy-(C1-C4)alkyl group is optionally substituted by one or two substituents selected from the group consisting of halo, cyano, (C1-C4)alkyl optionally substituted by 1 to 3 halogen atoms, and (C1-C4)alkoxy optionally substituted by 1 to 3 halogen atoms or
- a group of formula $$-(CH_2)_qNR_6R_7$$

in which q represents an integer from 2 to 8 and $R_6$ and $R_7$ independently represent
- hydrogen or
- $(C_1-C_4)$ alkyl or
- a cycloalkyl of 3 to 8 carbon atom optionally substituted by one or two substituents independently selected from the group consisting of halo, cyano, (C1-C4)alkyl optionally substituted by 1 to 3 halogen atoms, (C1-C4)alkoxy optionally substituted by 1 to 3 halogen atoms, phenyl, phenyl-(C1-C4)alkyl, phenoxy, and phenoxy-(C1-C4)alkyl wherein each of phenyl, phenyl portion of the phenyl (C1-C4), alkoxy, phenoxy, phenoxy portion of the phenoxy-(C1-C4)alkyl group is optionally substituted by one or two substituents selected from the group consisting of halo, cyano, (C1-C4)alkyl optionally substituted by 1 to 3 halogen atoms, and (C1-C4)alkoxy optionally substituted by 1 to 3 halogen atoms or a phenyl radical optionally substituted by one or two substituents independently selected from the group consisting of halo, cyano, (C1-C4)alkyl optionally substituted by 1 to 3 halogen atoms, (C1-C4)alkoxy optionally substituted by 1 to 3 halogen atoms, phenyl, phenyl-(C1-C4)alkyl, phenoxy, and phenoxy-(C1-C4)alkyl wherein each of phenyl, phenyl portion of the phenyl (C1-C4), alkoxy, phenoxy, phenoxy portion of the phenoxy-(C1-C4)alkyl group is optionally substituted by 1 to 3 halogen atoms, and (C1-C4)alkoxy optionally substituted by 1 to 3 halogen atoms or a benzyl radical optionally substituted on the phenyl ring by one or two substituents independently selected from the group consisting of halo, cyano, (C1-C4)alkyl optionally substituted by 1 to 3 halogen atoms, (C1-C4)alkoxy optionally substituted by 1 to 3 halogen atoms, phenyl, phenyl-(C1-C4)alkyl, phenoxy, and phenoxy-(C1-C4)alkyl wherein each of phenyl, phenyl portion of the phenyl (C1-C4), alkoxy, phenoxy, phenoxy portion of the phenoxy-(C1-C4)alkyl group is optionally substituted by one or two substituents selected from the group consisting of halo, cyano, (C1-C4)alkyl optionally substituted by 1 to 3 halogen atoms, and (C1-C4)alkoxy optionally substituted by 1 to 3 halogen atoms; and $R_6$ and $R_7$ taken together represent a $-(CH_2)_3-$, $-(CH_2)_4-$, $-(CH_2)_2-O-(CH_2)_2-$, $-(CH_2)_2-S-(CH_2)_2-$ or $R_6$ and $R_7$ taken together with the adjacent nitrogen atom represent: a piperazine moiety which may be substituted in position 4 with a substituent selected from the group consisting of ($C_1$-$C_4$ alkyl, ($C_3$-$C_8$) cycloalkyl, pyridyl, benzyl, and substituted benzyl wherein the phenyl moiety bears 1 or 2 substituents selected from the group consisting of chloro, bromo, nitro, ($C_1$-$C_4$) alkyl, and ($C_1$-$C_4$) alkoxy;

provided that at least one of R1 and R2 is not OH.

24. The compound according to claim 23, wherein X is Ile.

25. The compound according to claim 23, wherein X is Ile, Y is Tyr, n is 1, and R1 and R2 are NR3R4 wherein R3 (or R4) is H, and R4 (or R3) is (CH2)qNR6R7 with q=2, and R6 and R7 are H.

26. The compound according to claim 23, wherein X is Ile, Y is Trp, n is 2, and R1 and R2 are NR3R4 wherein R3 (or R4) is H, and R4 (or R3) is (CH2)qNR6R7 with q=2, and R6 and R7 are H.

27. A pharmaceutical composition comprising a compound of formula (I) (SEQ ID No. 5) according to claim 23 or its pharmaceutically acceptable salt.

28. The pharmaceutical composition according to claim 18 further comprising a pharmaceutically acceptable carrier.

29. The pharmaceutical composition according to claim 18 characterized in that it is orally, topically, or parenterally administrable.

30. The pharmaceutical composition according to claim 18 characterized in that it is in the forms of capsules, tablets, liquid solutions or suspensions aqueous, oily solutions or suspensions, hydrophobic or hydrophilic bases as ointments, creams, lotions, paints, or powders.

31. A method for the treatment of bacterial infections comprising administering a compound of formula (I) (SEQ ID No. 5) according to claim 23 or its pharmaceutically acceptable salt.

32. The method according to claim 1, wherein said bacterial infections are caused by enterococci, streptococci, or staphylococci.

33. The method according to claim 1, wherein said bacterial infections are caused by *Clostridium difficile, Staphylococcus* spp., *Streptococcus* spp., or *Enterococcus* spp.

34. The method according to claim 1, wherein the dosage range is comprised between 1 and 40 mg of active ingredient per Kg of body weight.

* * * * *

UNITED STATES PATENT AND TRADEMARK OFFICE
CERTIFICATE OF CORRECTION

PATENT NO. : 9,975,930 B2
APPLICATION NO. : 14/648696
DATED : May 22, 2018
INVENTOR(S) : Sonia I. Maffioli et al.

It is certified that error appears in the above-identified patent and that said Letters Patent is hereby corrected as shown below:

On the Title Page

Item (72):
The address of the inventor Paolo Monciardini which appears as - Cislago (IL) - should be changed to read -- Cislago (IT) --
and
The address of the inventor Carlo Mazzetti which appears as - Milan (IL) - should be changed to read -- Milan (IT) --

Signed and Sealed this
Sixteenth Day of October, 2018

Andrei Iancu
*Director of the United States Patent and Trademark Office*